US010925954B2

(12) United States Patent
Follmann et al.

(10) Patent No.: US 10,925,954 B2
(45) Date of Patent: Feb. 23, 2021

(54) VACCINES AGAINST *CHLAMYDIA* SP

(71) Applicant: Statens Serum Institut, Copenhagen S (DK)

(72) Inventors: Frank Follmann, Soborg (DK); Ida Rosenkrands, Vaerlose (DK); Anja Olsen, Soborg (DK); Peter Andersen, Bronshoj (DK)

(73) Assignee: Statens Serum Institut, Copenhagen (DK)

( * ) Notice: Subject to any disclaimer, the term of this patent is extended or adjusted under 35 U.S.C. 154(b) by 0 days.

(21) Appl. No.: 15/956,731

(22) Filed: Apr. 18, 2018

(65) Prior Publication Data

US 2019/0099478 A1 Apr. 4, 2019

Related U.S. Application Data

(63) Continuation of application No. 14/216,403, filed on Mar. 17, 2014, now abandoned.

(60) Provisional application No. 61/802,907, filed on Mar. 18, 2013.

(30) Foreign Application Priority Data

Mar. 18, 2013 (DK) .......................... PA 2013 00155
Dec. 11, 2013 (DK) .......................... PA 2013 00684

(51) Int. Cl.
*A61K 39/118* (2006.01)
*C07K 14/295* (2006.01)
*A61K 39/00* (2006.01)

(52) U.S. Cl.
CPC .......... *A61K 39/118* (2013.01); *C07K 14/295* (2013.01); *A61K 2039/6031* (2013.01); *C07K 2319/40* (2013.01)

(58) Field of Classification Search
CPC .......... A61K 2039/6031; A61K 39/118; C07K 14/295; C07K 2319/40
See application file for complete search history.

(56) References Cited

U.S. PATENT DOCUMENTS

| 5,869,608 | A | 2/1999 | Caldwell et al. |
| 6,384,206 | B1 | 5/2002 | Caldwell et al. |
| 6,680,182 | B1 | 1/2004 | Khan et al. |
| 2009/0214570 | A1 | 8/2009 | Mrsny et al. |
| 2009/0304722 | A1 | 12/2009 | Theisen et al. |

FOREIGN PATENT DOCUMENTS

| WO | WO 94/06827 A1 | 3/1994 |
| WO | WO 2011/147975 A1 | 12/2011 |
| WO | WO 2012/172042 A1 | 12/2012 |

OTHER PUBLICATIONS

Anttila, et al., Serotypes of Chlamydia trachomatis and risk for development of cervical squamous cell carcinoma, JAMA, Jan. 3, 2001, 285(1): 47-51.
Baehr, et al, Mapping antigenic domains expressed by Chlamydia trachomatis major outer membrane protein genes, Proc Natl Acad Sci USA., Jun. 1988, 85(11): 4000-4004.
Bandea, et al., Chlamydia trachomatis serovars among strains isolated from members of rural indigenous communities and urban populations in Australia, J Clin Microbiol., Jan. 2008, 46(1): 355-356.
Batteiger, et al., Protective immunity to Chlamydia trachomatis genital infection: evidence from human studies, J Infect Dis., Jun. 15, 2010, 201 Suppl 2: S178-S189.
Bavoil, et al., Role of disulfide bonding in outer membrane structure and permeability in Chlamydia trachomatis, Infect Immun., May 1984, 44(2): 479-485.
Brunham, et al., Immunology of Chlamydia infection: implications for a Chlamydia trachomatis vaccine, Nat Rev Immunol., Feb. 2005, 5(2): 149-161.
Caldwell, et al., Neutralization of Chlamydia trachomatis infectivity with antibodies to the major outer membrane protein, Infect Immun., Nov. 1982, 38(2): 745-754.
Caldwell, et al., Purification and partial characterization of the major outer membrane protein of Chlamydia trachomatis, Infect Immun., Mar. 1981, 31(3): 1161-1176.
Carmichael, et al., Induction of protection against vaginal shedding and infertility by a recombinant Chlamydia vaccine, Vaccine, Jul. 18, 2011, 29(32): 5276-5283—author manuscript format submitted (available in PMC Jul. 18, 2012—18 pp.).
Cheng, et al., Characterization of the humoral response induced by a peptide corresponding to variable domain IV of the major outer membrane protein of Chlamydia trachomatis serovar E, Infect Immun., Aug. 1992, 60(8):3428-3432.
Coler, et al., Identification and characterization of novel recombinant vaccine antigens for immunization against genital Chlamydia trachomatis, FEMS Immunol Med Microbiol., Mar. 2009, 55(2): 258-270—author manuscript format submitted (available in PMC Mar. 1, 2010—19 pp.).

(Continued)

*Primary Examiner* — James H Alstrum-Acevedo
*Assistant Examiner* — Erinne R Dabkowski
(74) *Attorney, Agent, or Firm* — Duminiak Law, LLC; Robert J. Duminiak

(57) ABSTRACT

The present invention describes an efficient vaccine against a *Chlamydia trachomatis* (Ct). The vaccine is based on recombinant fusion molecules that are capable of generating a high titered neutralizing antibody response that is protective against various Ct serovars. Our invention furthermore describe the combination of these antibody promoting fragments with Ct antigens that are targets for T cells with the aim to provide a vaccine that activate both arms of the immune system.

15 Claims, 28 Drawing Sheets

Specification includes a Sequence Listing.

(56) References Cited

OTHER PUBLICATIONS

Cotter, et al . . . , Protective efficacy of major outer membrane protein-specific immunoglobulin A (IgA) and IgG monoclonal antibodies in a murine model of Chlamydia trachomatis genital tract infection, Infect Immun., Dec. 1995, 63(12): 4704-4714.
Crane, et al., Chlamydia trachomatis polymorphic membrane protein D is a species-common pan-neutralizing antigen, Proc Natl Acad Sci USA., Feb. 7, 2006, 103(6): 1894-1899.
Darville, et al., Pathogenesis of genital tract disease due to *Chlamydia trachomatis*, J Infect Dis., Jun. 15, 2010, 201 Suppl 2: S114-S125—author manuscript format submitted (available in PMC Aug. 4, 2011—18 pp.).
Farris, et al., Vaccination against Chlamydia genital infection utilizing the murine *C. muridarum* model, Infect Immun., Mar. 2011, 79(3): 986-996.
Findlay, et al., Surface expression, single-channel analysis and membrane topology of recombinant Chlamydia trachomatis Major Outer Membrane Protein, BMC Microbiol., Jan. 26, 2005, 5:5, 15 pp.
Follmann, et al., Antigenic profiling of a Chlamydia trachomatis gene-expression library, J Infect Dis., Mar. 15, 2008 edition, published electronically on Feb. 20, 2008, 197 (6):897-905.
Golden, et al., Duration of untreated genital infections with chlamydia trachomatis: a review of the literature, Sex Transm Dis., Jul. 2000, 27(6): 329-337.
Hansen, et al., Liposome Delivery of *Chlamydia muridarum* Major Outer Membrane Protein Primes a Th1 Response That Protects against Genital Chlamydial Infection in a Mouse Model, J Infect Dis., electronically published Jul. 24, 2008, 198(5): 758-767.
Harboe, et al., Evidence for occurrence of the ESAT-6 protein in *Mycobacterium tuberculosis* and virulent *Mycobacterium bovis* and for its absence in *Mycobacterium bovis* BCG, Infect Immun., Jan. 1996, 64(1): 16-22.
Hatch, et al., Structural and polypeptide differences between envelopes of infective and reproductive life cycle forms of *Chlamydia* spp., J Bacteriol., Jan. 1984, 157(1): 13-20.
Hinton, et al, Pattern recognition by B cells: the role of antigen repetitiveness versus Toll-like receptors. Current topics in microbiology and immunology, 2008, 319: 1-15—pp. 1-5 provided.
Hsu, et al., Genotyping of *Chlamydia trachomatis* from clinical specimens in Taiwan, J Med Microbiol., Mar. 2006, 55(Pt 3): 301-308.
Jonsdottir, et al., The molecular epidemiology of genital Chlamydia trachomatis in the greater Reykjavik area, Iceland, Sex Transm Dis., Mar. 2003, 30(3): 249-256.
Kari, et al., Chlamydia trachomatis native major outer membrane protein induces partial protection in nonhuman primates: implication for a trachoma transmission-blocking vaccine, J Immunol., Jun. 15, 2009, 182(12): 8063-8070.
Karunakaran, et al., Immunoproteomic discovery of novel T cell antigens from the obligate intracellular pathogen *Chlamydia*, J Immunol., Feb. 15, 2008, 180(4): 2459-2465.
Kawa, et al., Immune response to the Chlamydia trachomatis outer membrane protein PorB, Vaccine, Oct. 2004, 22(31-32):4282-4286.
Kim, et al., Epitope clusters in the major outer membrane protein of Chlamydia trachomatis, Curr Opin Immunol., Aug. 2001, 13(4): 429-436.
Kubo, et al., Characterization and functional analysis of PorB, a Chlamydia porin and neutralizing target, Mol Microbiol., Nov. 2000, 38(4): 772-780.
Li, et al., Immunization with a combination of integral chlamydial antigens and a defined secreted protein induces robust immunity against genital chlamydial challenge, Infect Immun., Sep. 2010, 78(9): 3942-3949.
Lysen, et al., Characterization of ompA genotypes by sequence analysis of DNA from all detected cases of Chlamydia trachomatis infections during 1 year of contact tracing in a Swedish County, J Clin Microbiol., Apr. 2004, 42(4): 1641-1647.
Millman, et al. Population-based genetic and evolutionary analysis of Chlamydia trachomatis urogenital strain variation in the United States, J Bacteriol., Apr. 2004, 186(8): 2457-2465.
Molina, et al., Identification of immunodominant antigens of Chlamydia trachomatis using proteome microarrays, Vaccine Apr. 9, 2010, 28(17): 3014-3024—author manuscript format submitted (available in PMC Apr. 9, 2011—21 pp.).
Moore, et al., Fc receptor-mediated antibody regulation of T cell immunity against intracellular pathogens, J Infect Dis., electronically published Mar. 17, 2003, 188(4): 617-624.
Morrison, et al., Immunity to murine Chlamydia trachomatis genital tract reinfection involves B cells and CD4(+) T cells but not CD8(+) T cells, Infect Immun., Dec. 2000, 68(12): 6979-6987.
Morrison, et al., Resolution of secondary Chlamydia trachomatis genital tract infection in immune mice with depletion of both CD4+ and CD8+ T cells, Infect Immun., Apr. 2001, 69(4): 2643-2649.
Morrison, et al., Immunity to murine chlamydial genital infection, Infect Immun., Jun. 2002, 70(6): 2741-2751.
Motin, et al., Immunization with a peptide corresponding to chlamydial heat shock protein 60 increases the humoral immune response in C3H mice to a peptide representing variable domain 4 of the major outer membrane protein of *Chlamydia trachomatis*, Clin Diagn Lab Immunol., May 1999, 6(3): 356-363.
Murdin, et al., A poliovirus hybrid expressing a neutralization epitope from the major outer membrane protein of Chlamydia trachomatis is highly immunogenic, Infect Immun., Oct. 1993, 61(10): 4406-4414.
Murdin, et al., Poliovirus hybrids expressing neutralization epitopes from variable domains I and IV of the major outer membrane protein of Chlamydia trachomatis elicit broadly cross-reactive *C. trachomatis*-neutralizing antibodies, Infect Immun., Mar. 1995, 63(3): 1116-1121.
Mygind, et al., Detection of Chlamydia trachomatis-specific antibodies in human sera by recombinant major outer-membrane protein polyantigens, J Med Microbiol, May 2000, 49(5): 457-465.
Nunez, et al., Dominant Antigen Reveals Distinct Evolutionary Scenarios for B- and T-cell Epitopes: Worldwide Survey, PLOS One, Oct. 5, 2010, 5(10):e13171 (10 pp.).
Olsen, et al., Identification of CT521 as a frequent target of Th1 cells in patients with urogenital Chlamydia trachomatis infection, J Infect Dis., electronically published Sep. 22, 2006, 194(9): 1258-1266.
Olsen, et al., Identification of human T-cell targets recognized during the Chlamydia trachomatis genital infection, J Infect Dis., electronically published Oct. 31, 2007, 196: 1546-1552.
Olsen, et al., Protection against Chlamydia promoted by a subunit vaccine (CTH1) compared with a primary intranasal infection in a mouse genital challenge model, PLoS One, May 21, 2010, 5(5): e10768 (11 pp.).
Paavonen, et al., Chlamydia trachomatis: impact on human reproduction, Hum Reprod Update., Sep. 1999, 5(5): 433-447.
Pal, et al., Vaccination of mice with DNA plasmids coding for the Chlamydia trachomatis major outer membrane protein elicits an immune response but fails to protect against a genital challenge, Vaccine, Feb. 5, 1999, 17(5): 459-465.
Pal, et al., Immunogenic and protective ability of the two developmental forms of *Chlamydiae* in a mouse model of infertility, Vaccine, Nov. 12, 1999, 18(7-8): 752-761.
Pal, et al., Immunization with the *Chlamydia trachomatis* mouse pneumonitis major outer membrane protein can elicit a protective immune response against a genital challenge, Infect Immun., Oct. 2001, 69(10): 6240-6247.
Peeling, et al., In vitro neutralization of Chlamydia trachomatis with monoclonal antibody to an epitope on the major outer membrane protein, Infect Immun., Nov. 1984, 46(2): 484-488.
Peterson, et al., The effect of orientation within a chimeric peptide on the immunogenicity of Chlamydia trachomatis epitopes, Mol Immunol., Mar. 1996, 33(4-5): 335-339.
Plummer, et al., Cofactors in male-female sexual transmission of human immunodeficiency virus type 1, J Infect Dis., Feb. 1991, 163(2): 233-239.
Qu, et al., Characterization of a Neutralizing Monoclonal Antibody Directed at Variable Domain I of the Major Outer Membrane

(56) References Cited

OTHER PUBLICATIONS

Protein of *Chlamydia trachomatis* C-Complex Serovars, Infect Imm., Apr. 1993, 61(4):1365-1370.
Qu, et al., Analysis of the humoral response elicited in mice by a chimeric peptide representing variable segments I and IV of the major outer membrane protein of *Chlamydia trachomatis*, Vaccine, May 1994, 12(6): 557-564.
Rasmussen, Chlamydia immunology, Curr Opin Infect Dis., Feb. 1998, 11(1): 37-41.
Ravn, et al., Human T cell responses to the ESAT-6 antigen from *Mycobacterium tuberculosis*, J Infect Dis, Mar. 1999, 179(3): 637-645.
Rockey, et al., Chlamydia vaccine candidates and tools for chlamydial antigen discovery, Expert Rev Vaccines., Oct. 2009, 8(10):1365-1377.
Sette, et al., Reverse vaccinology: developing vaccines in the era of genomics, Immunity, Oct. 2010, 33(4): 530-541—author manuscript format submitted (available in PMC Apr. 6, 2012—23 pp.).
Sharma, et al., Profiling of human antibody responses to Chlamydia trachomatis urogenital tract infection using microplates arrayed with 156 chlamydial fusion proteins, Infect Immun., Mar. 2006, 74(3): 1490-1499.
Shaw, et al., Dendritic cells pulsed with a recombinant chlamydial major outer membrane protein antigen elicit a CD4(+) type 2 rather than type 1 immune response that is not protective, Infect Immun., Mar. 2002, 70(3): 1097-1105.
Stephens, et al., Diversity of Chlamydia trachomatis major outer membrane protein genes, J Bacteriol., Sep. 1987, 169(9): 3879-3885.
Stephens, et al., High-resolution mapping of serovar-specific and common antigenic determinants of the major outer membrane protein of Chlamydia trachomatis, J Exp Med., Mar. 1, 1988, 167(3): 817-831.
Su, et al., Immunogenicity of a synthetic oligopeptide corresponding to antigenically common T-helper and B-cell neutralizing epitopes of the major outer membrane protein of Chlamydia trachomatis, Vaccine, 1993, 11(11): 1159-1166.
Su, et al., Protective efficacy of a parenterally administered MOMP-derived synthetic oligopeptide vaccine in a murine model of Chlamydia trachomatis genital tract infection: serum neutralizing IgG antibodies do not protect against chlamydial genital tract infection, Vaccine, Aug. 1995, 13(11):1023-1032.
Su, et al., CD4+ T cells play a significant role in adoptive immunity to *Chlamydia trachomatis* infection of the mouse genital tract, Infect Immun., Sep. 1995, 63(9): 3302-3308.
Tifrea, et al., Vaccination with the Recombinant Major Outer Membrane Protein Elicits Antibodies to the Constant Domains and Induces Cross-Serovar Protection against Intranasal Challenge with Chlamydia trachomatis, Infect. Immun., epub Mar. 11, 2013, 81(5):1741-1750.
Toye, et al., Immunologic characterization of a cloned fragment containing the species-specific epitope from the major outer membrane protein of *Chlamydia trachomatis*, Infect Immun., Dec. 1990, 58(12): 3909-3913.
Villeneuve, et al., Characterization of the humoral response induced by a synthetic peptide of the major outer membrane protein of Chlamydia trachomatis serovar B, Infect Immun., Aug. 1994, 62(8): 3547-3549.
Villeneuve, et al., Determination of neutralizing epitopes in variable domains I and IV of the major outer-membrane protein from Chlamydia trachomatis serovar K, Microbiology, Sep. 1994, 140 ( Pt 9): 2481-2487.
Volp, et al., Peptide immunization of guinea pigs against *Chlamydia psittaci* (GPIC agent) infection induces good vaginal secretion antibody response, in vitro neutralization and partial protection against live challenge, Immunol Cell Biol., Jun. 2001, 79(3): 245-250.

Who, Global Prevalence and Incidence of selected Curable Sexually Transmitted Infections: Overview and Estimates, World Health Organization, Geneva, Switzerland, Nov. 2001, 50 pp. (42 numbered pages).
Xu, et al., Protective immunity against *Chlamydia trachomatis* genital infection induced by a vaccine based on the major outer membrane multi-epitope human papillomavirus major capsid protein L1, Vaccine, Mar. 2011, epub Feb. 12, 2011, 29(15):2672-2678.
Yen, et al., Characterization of the disulfide bonds and free cysteine residues of the *Chlamydia trachomatis* mouse pneumonitis major outer membrane protein, Biochemistry, Apr. 2005, 44(16):6250-6256.
Yu, et al., Novel Chlamydia muridarum T cell antigens induce protective immunity against lung and genital tract infection in murine models, J Immunol., Feb. 1, 2009, 182(3): 1602-1608—author manuscript format submitted (available in PMC Feb. 1, 2010—18 pp.).
Zhang, et al., Protective monoclonal antibodies recognize epitopes located on the major outer membrane protein of Chlamydia trachomatis, J Immunol., Jan. 15, 1987, 138(2): 575-581.
Zhang, et al., Protective monoclonal antibodies to Chlamydia trachomatis serovar- and serogroup-specific major outer membrane protein determinants, Infect Immun., Feb. 1989, 57(2): 636-638.
Zhang, et al., Characterization of immune responses following intramuscular DNA immunization with the MOMP gene of *Chlamydia trachomatis* mouse pneumonitis strain, Immunology, Feb. 1999, 96(2): 314-321.
International Search Report dated Jul. 24, 2014 in International Patent Application No. PCT/DK2014/000015, which application shares common priority with the present application.
Written Opinion dated Jul. 24, 2014 in International Patent Application No. PCT/DK2014/000015, which application shares common priority with the present application.
Sep. 24, 2014 Letter accompanying the Article 34 Claim Amendments and comments to the Written Opinion in International Patent Application No. PCT/DK2014/000015, which application shares common priority with the present application.
Sep. 24, 2014 Article 34 Claim Amendments in International Patent Application No. PCT/DK2014/000015, which application shares common priority with the present application.
Batteiger, et al., The major outer membrane protein of a single Chlamydia trachomatis serovar can possess more than one serovar-specific epitope, Infect Immun., Feb. 1996, 64(2):542-547.
Batteiger, et al., Species-, serogroup-, and serovar-specific epitopes are juxtaposed in variable sequence region 4 of the major outer membrane proteins of some *Chlamydia trachomatis* serovars, Infect Immun., Jul. 1996, 64(7):2839-2841.
Su, et al., Immunogenicity of a chimeric peptide corresponding to T helper and B cell epitopes of the Chlamydia trachomatis major outer membrane protein, J Exp Med., Jan. 1992, 175(1):227-235.
Kang, et al., Processing and Reactivity of T Cell Epitopes Containing Two Cysteine Residues from Hen Egg-White Lysozyme ($HEL_{74-90}$), J. Immunol., Feb. 2000, 164 (4) 1775-1782.
Kalbina, et al., A novel chimeric MOMP antigen expressed in *Escherichia coli, Arabidopsis thaliana*, and *Daucus carota* as a potential Chlamydia trachomatis vaccine candidate, Protein Expression and Purification, Dec. 2011, 80(2):194-202.
Pal, et al., Mapping of a surface-exposed B-cell epitope to the variable sequent 3 of the major outer-membrane protein of Chlamydia trachomatis, J. Gen. Microbiol., Jul. 1993, 139(7):1565-70.
Office Action dated Jun. 16, 2020 (drafted Jun. 2, 2020) in counterpart Japanese Patent Application No. 2019-052389.
Kaltenboeck, et al., Structures of and allelic diversity and relationships among the major . . . , J Bacteriol., Jan. 1993, 175(2): 487-502.
Su, et al., Differential effect of trypsin on infectivity of Chlamydia trachomatis . . . , Infect Immun., Aug. 1988, 56(8): 2094-2100.
Yuan, et al., Nucleotide and deduced amino acid sequences for the four variable domains . . . , Infect Immun., Apr. 1989, 57(4): 1040-1049.
Zhang, et al., Cloning and sequence analysis of the major outer membrane protein genes . . . , Infect Immun., May 1989, 57(5): 1621-1625.

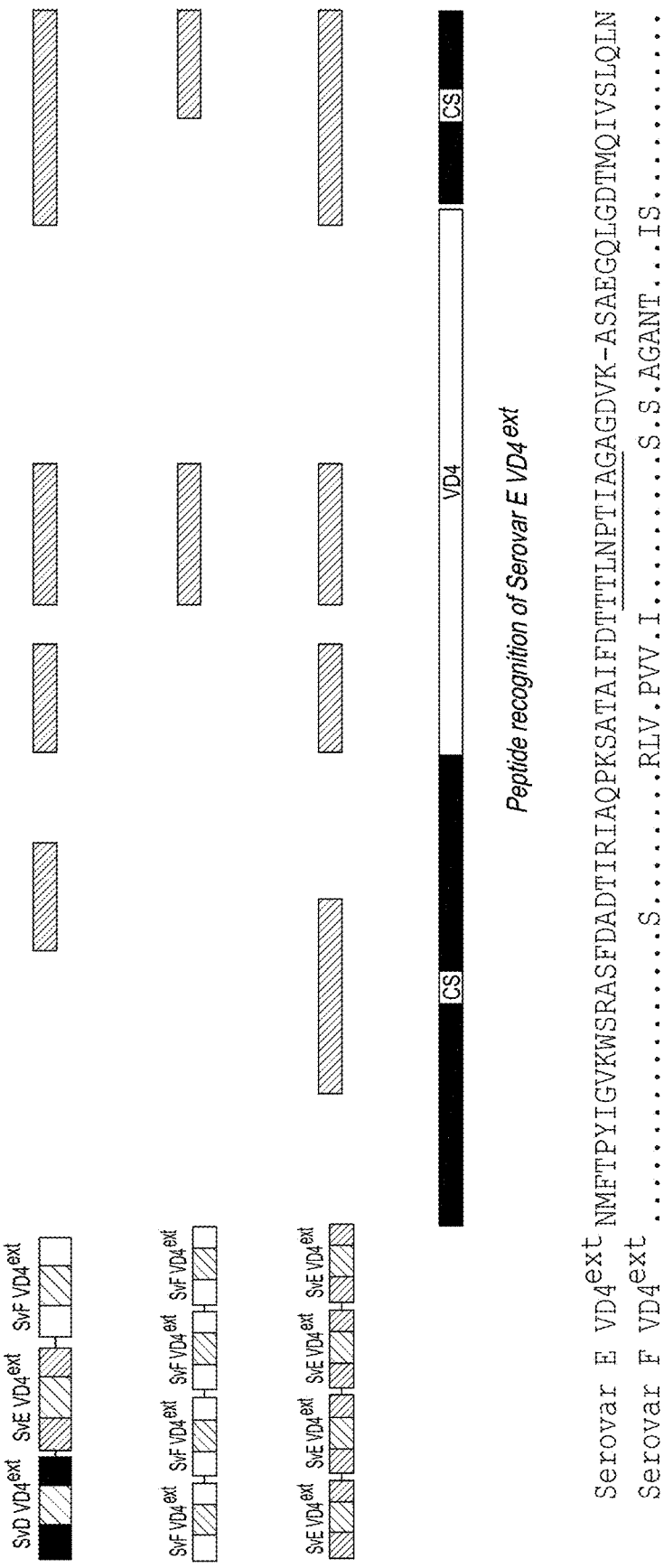

Figure 7 B)

Immunogen:

Peptide recognition of Serovar E VD4ext

```
Serovar E VD4ext  NMFTPYIGVKWSRASFDADTIRIAQPK

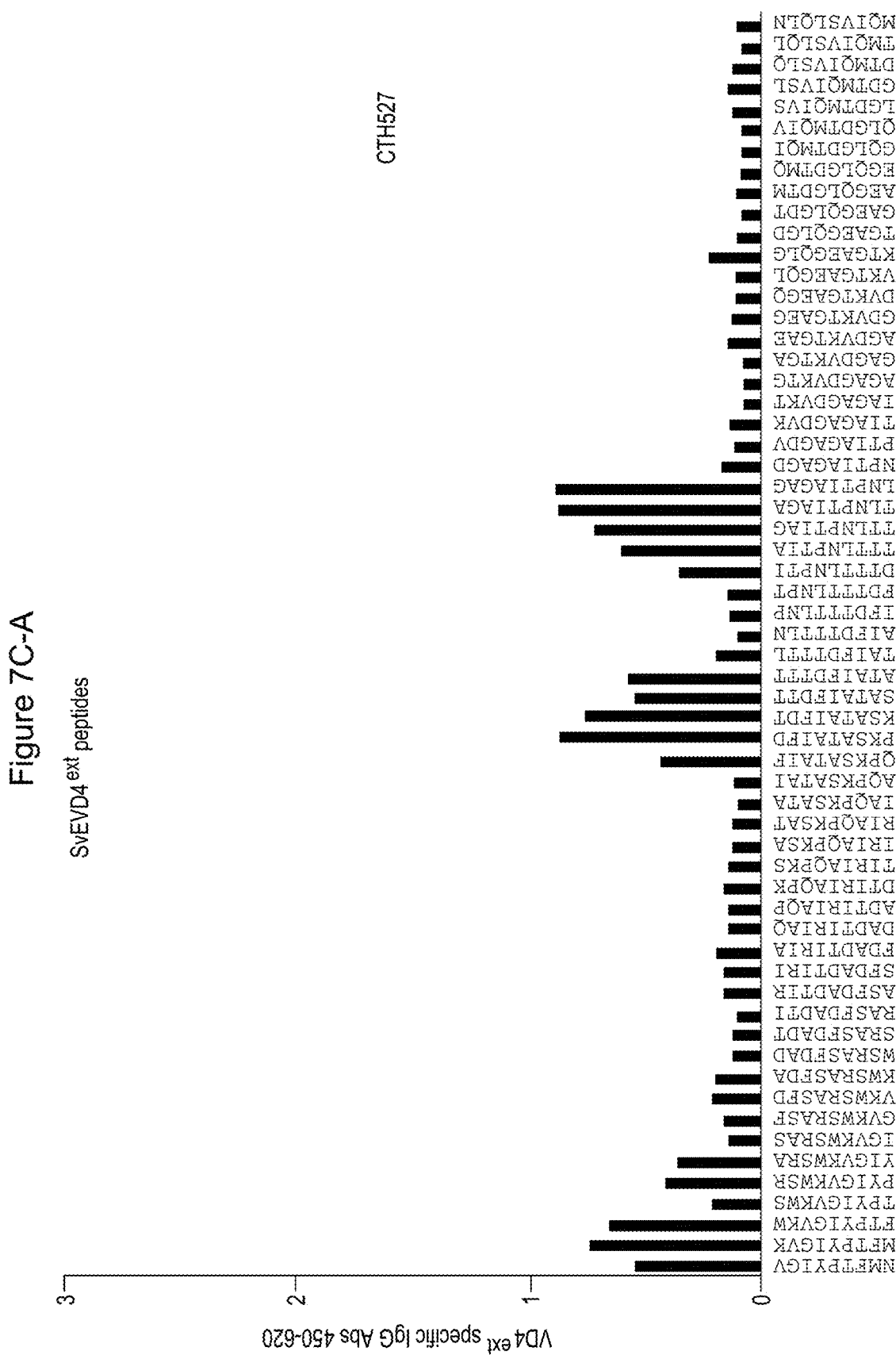

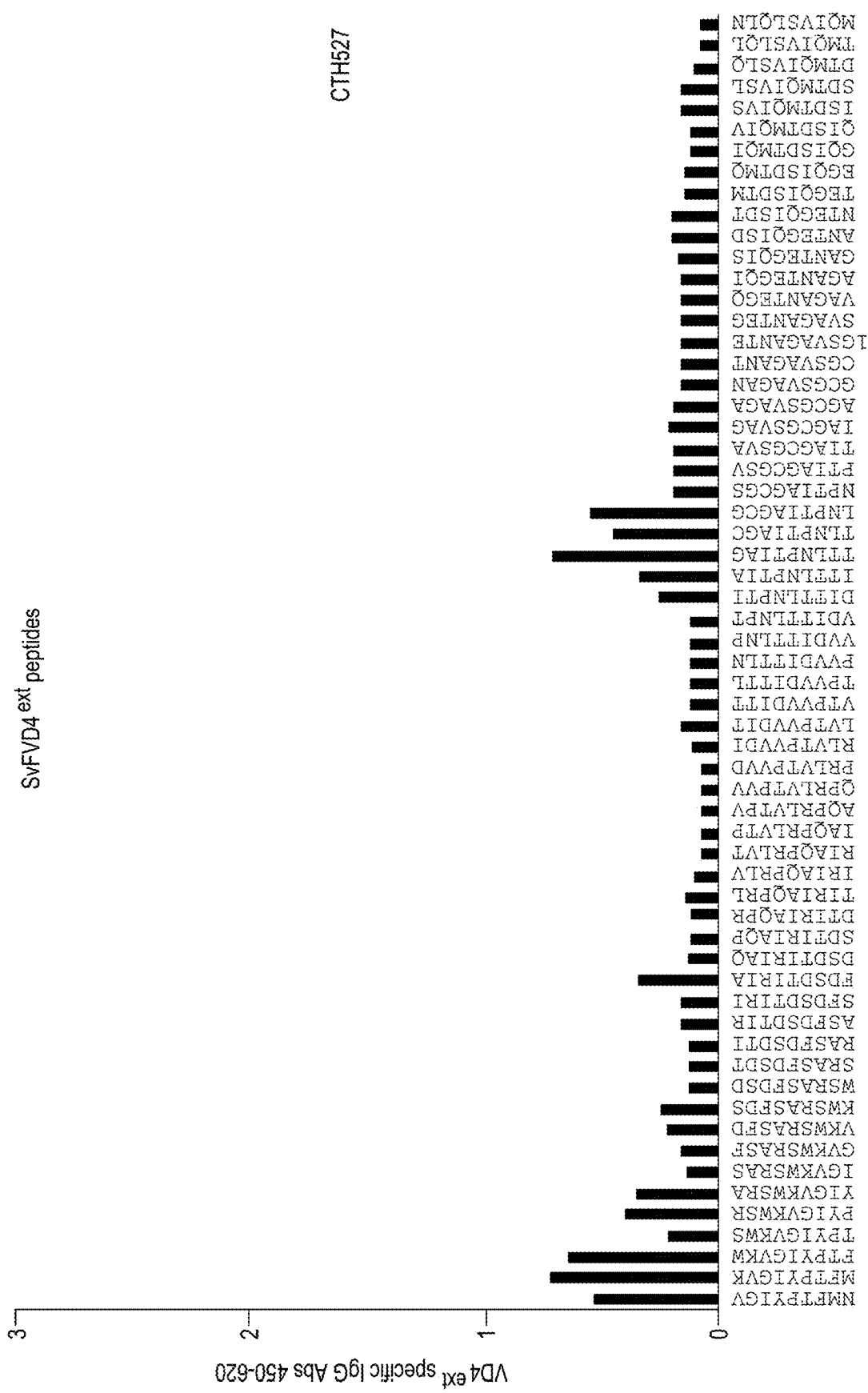

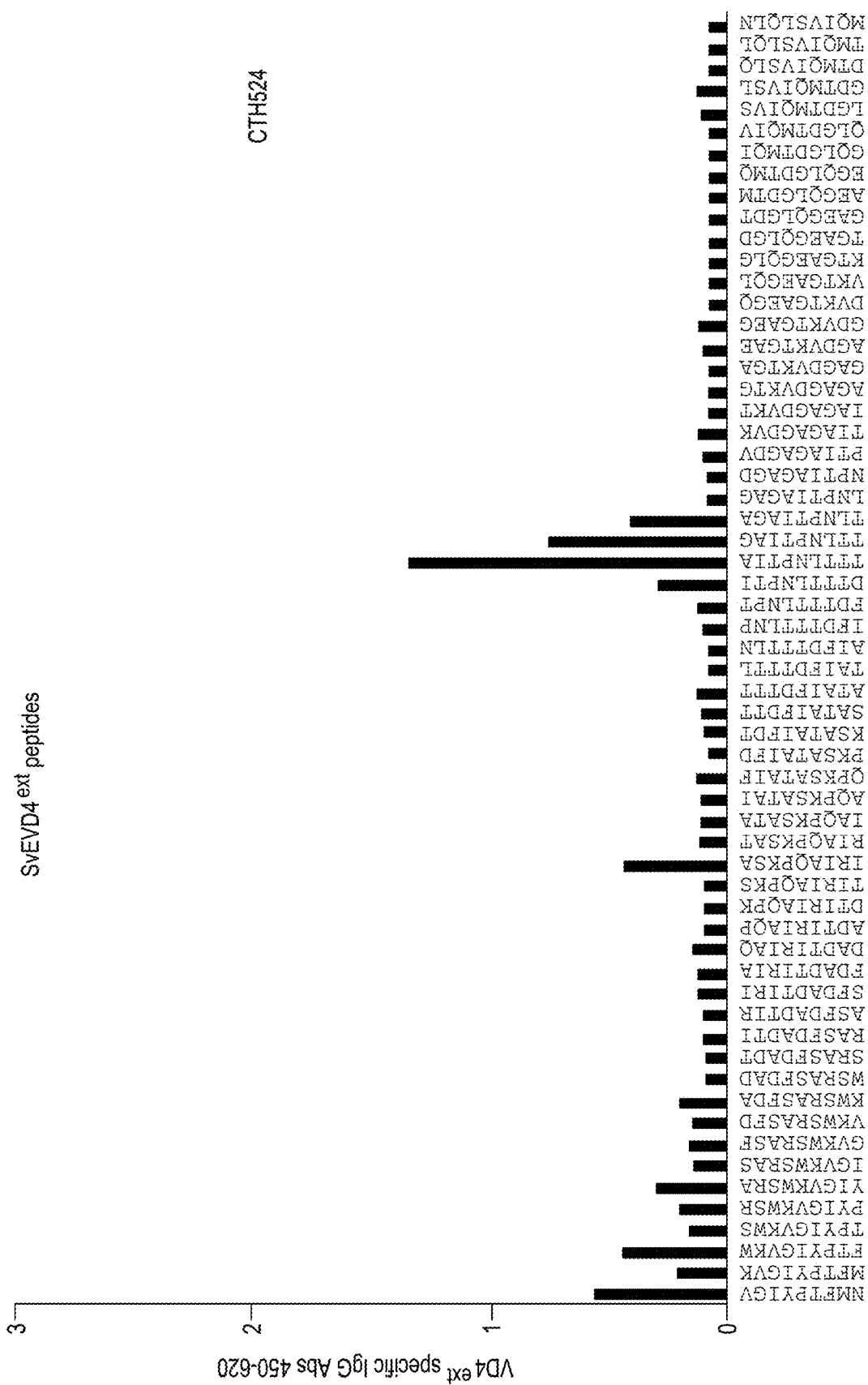
Figure 7C-B

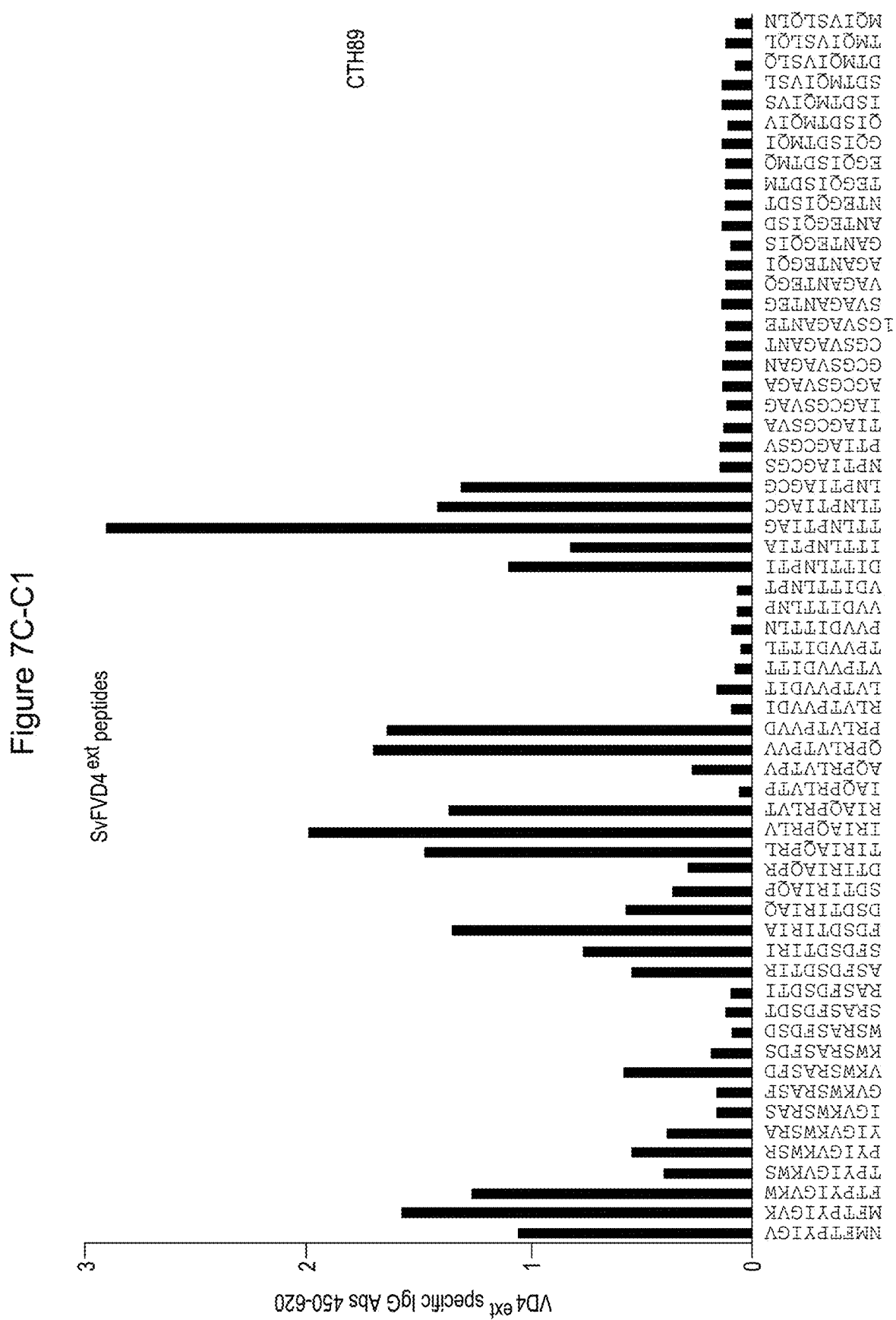

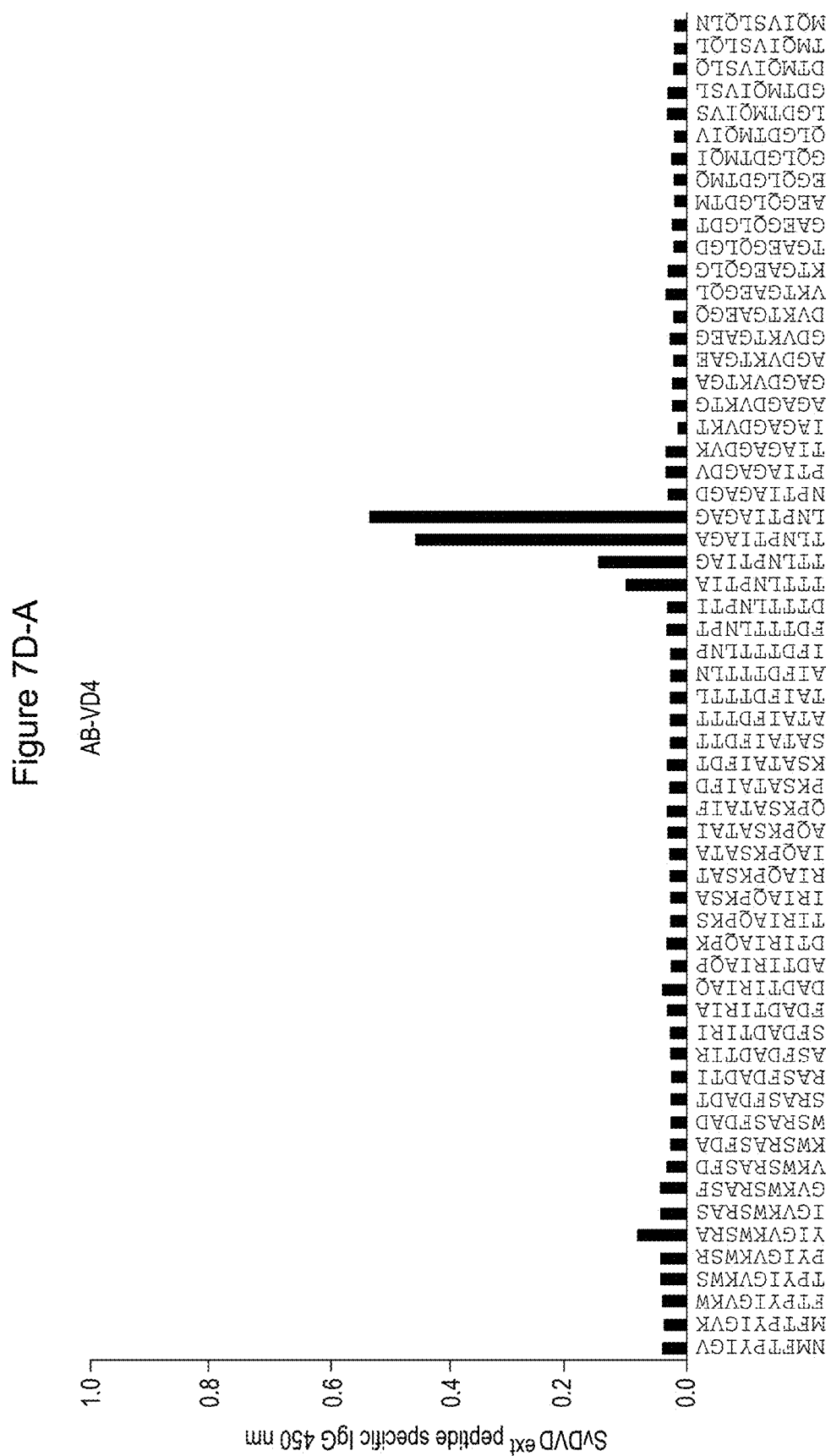
Figure 7D-A

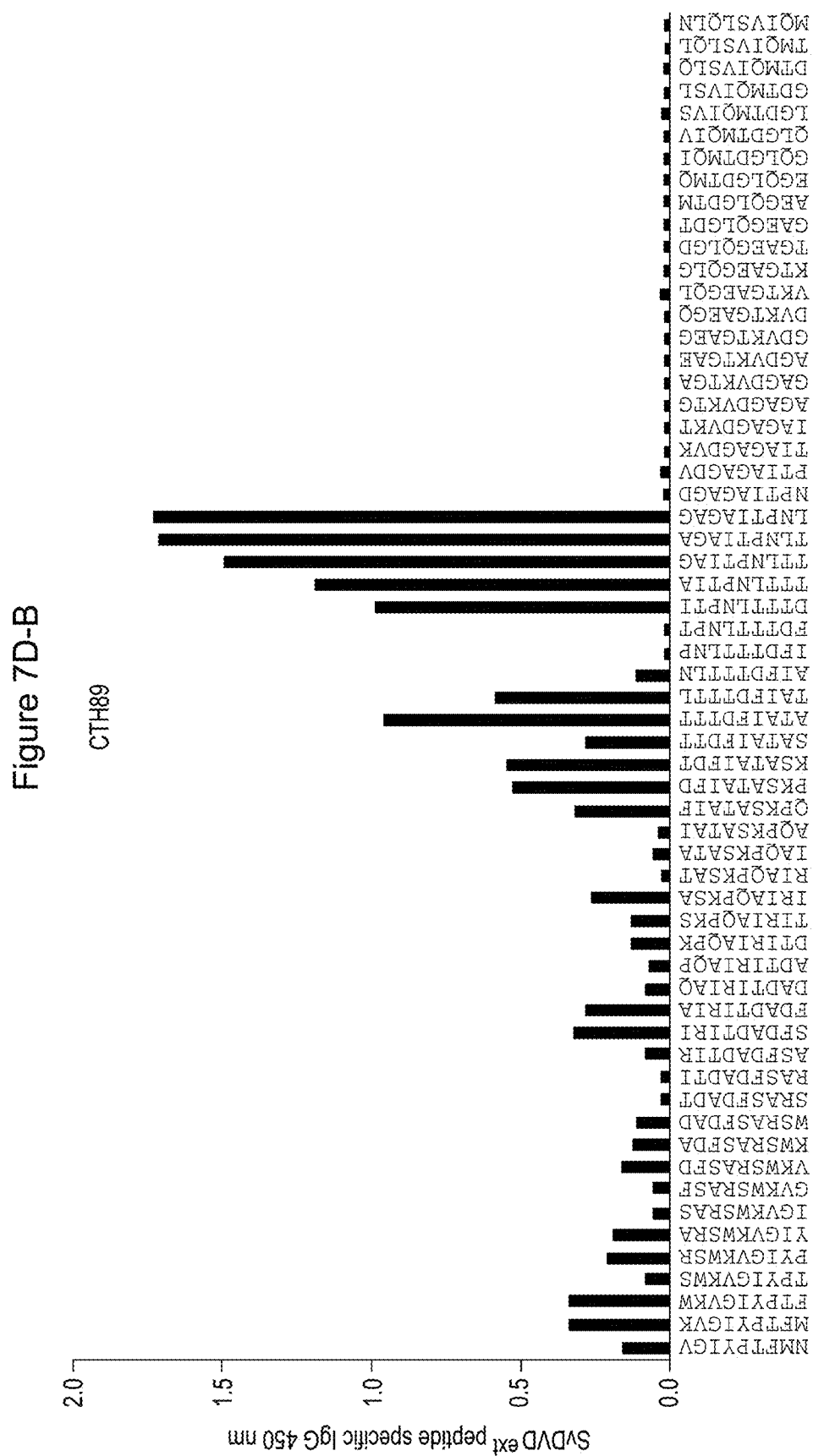
Figure 7D-B

Figure 7D-C

VACCINES AGAINST *CHLAMYDIA* SP

FIELD OF INVENTION

The present invention relates to polypeptides of repetitive units of immunogenic fragments of surface exposed regions of outer membrane proteins of *Chlamydia* sp. and pharmaceutical compositions and vaccines comprising these fusion proteins.

BACKGROUND OF THE INVENTION

Chlamydiae are intracellular bacterial pathogens responsible for a variety of infections. *Chlamydia pneumoniae* is responsible for human acute respiratory infection and believed to play a role in coronary heart disease. *Chlamydia trachomatis* is the causative agent of human sexually transmitted disease and eye infections (Trachoma). Also in animals, several infections with *Chlamydia* sp. are known, e.g. *Chlamydia Suis* infecting pigs, and *Chlamydiaphila abortus* which causes abortion in small ruminants (sheep and goats).

Worldwide, it is estimated that 92 million individuals become sexually infected with *Chlamydia trachomatis* (Ct)[1]. Urogenital infections with Ct are of public health concern because of its high prevalence and the fact that it's a risk factor for ectopic pregnancy and infertility[2]. In addition to this Ct infections have been shown to facilitate the transmission of HIV[3] and act as a co-factor in HPV-induced cervical carcinoma[4]. The duration of untreated genital Ct infection can be prolonged, and complete clearance is often not reached within the first 12 months[5]. From human studies it is known that some degree of protective immunity against genital re-infection develops, although it appears at best to be partial[6]. The infection is effectively controlled by antibiotic therapy; however the high prevalence of asymptomatic cases suggests that sustainable disease control can only be envisaged if an effective *Chlamydia* vaccine is developed.

A vaccine against Ct needs to elicit protective T-cell and B-cell immunity in the genital tract mucosa[1]. Immune mechanisms of clearance of infection and resistance to re-infection have been described in numerous studies. A variety of animal models and chlamydial species have been used in attempts to identify protective and damaging immune responses. A general consensus has emerged that, in mice, CD4+ Th1 cell mediated immune responses plays a major role in the resolution of Ct infection[8,9,10], whereas the role of humoral immunity in protection has remained less well defined. In guinea pigs immunity to chlamydial infection is mediated at least partly by secretory IgA at the mucosal surface[11,12] and also in the mouse model there is increasing evidence to support a role for antibodies in protective immunity[9]. Data from animal models that has emerged over the last years clearly demonstrate that if antibodies are formed after the infection is established they play a minimal role, whereas their presence at the time of infection (e.g. in a secondary response) promotes significant levels of protection, an effect that is however clearly amplified in the presence of *Chlamydia* specific CD4+ cells 9,13, 14. A strong cell mediated immune (CMI) response without antibodies may on the other hand control bacterial replication but can in the worst case exacerbate the pathology associated with *Chlamydia* infection[15,16]. The importance of this interplay between cell mediated immunity and antibodies is also becoming increasingly clear to support a preferential role of neutralizing antibodies in the initial phase of infection, whereas CD4+ cells are the main effectors throughout the rest of the infection[17,18,19]. In summary balancing the immune effector mechanisms between antibodies and T cells seems to be crucial for disease outcome.

We and others have identified a range of chlamydial antigens recognized during a natural infection in either humans or animal models[20,21,22,23,24,25,26,27]. Especially the publishing of the genome sequence in 1998 and modern high throughput techniques have led to the testing of almost the entire genome of 875 open reading frames[28]. Importantly, identifying proteins as antigenic during an infection do not necessarily mean they are protective as vaccines[29] and despite the characterization of such a large number of antigens only very few of these have been demonstrated to mediate protection as vaccines in animal models[30,31,32]. Furthermore for the majority of the vaccines recently reported the partial protection observed is mediated by T cells with no neutralizing antibodies. Therefore there is a lack of vaccine candidates that generate neutralizing antibodies that can cope with the infection in the initial phase and creating a balanced immune response.

Until now there has only been convincing data on neutralizing antibodies with three surface exposed antigens; PorB, which localized in the chlamydial outer membrane and functions as a porin[33]. Antibodies against this has been shown to neutralize chlamydial infectivity[34] patent ref: U.S. Pat. No. 7,105,171. Another more recent antigen is PmpD. This protein has been shown to generate neutralizing antibodies in vitro, however the in vivo relevance of these antibodies have not yet been demonstrated[35].

MOMP is the classical target antigen for neutralizing antibodies and one of the first antigenic molecules described. It is a surface-exposed trans membrane protein which has structural (porin) properties[36,37,38]. MOMP is a 40 kDa protein making up roughly 60% of the protein in the Ct membrane and is a target for neutralizing antibodies with proven efficacy both in vitro and in vivo. MOMP consists of four variable surface exposed domains (VD-1 to VD-4) separated by five constant segments[38,39] and it is the molecular basis of the serovar (~15) grouping of *Chlamydia* (FIG. 1). The in vitro and in vivo neutralizing antibody epitopes have been mapped to these VDs[40,41,42,43,44]. The distribution profile of Ct urogenital serovars has been described for regions worldwide, providing epidemiological data for the serovar coverage needed of a MOMP based vaccine. The most common serovar detected worldwide is E (22-49% of cases) followed by serovars F and D (17-22% and 9-19%, respectively)[45,46,47,48,49,50], meaning that a vaccine targeting serovars E, D and F would have a significant impact and cover more than 70% of the human population.

MOMP is highly immunogenic in humans and animals and has therefore been studied in great detail as a vaccine candidate, both as a natively purified protein, recombinantly and as DNA-vaccine. These vaccination attempts gave variable results[17,51,52,53,54,55,56,57]. The reason for the relative inconsistency of MOMP as a vaccine is not fully understood, but the fact that the synthetic MOMP immunogens do not mimic the native structure of the protein has been the major concern[54]. In this regard, the structure of this membrane bound cysteine rich molecule and refolding various products to achieve native protein structure has been extremely challenging and is not suitable for large scale vaccine production[58]. Therefore, although clearly with vaccine potential, full size MOMP has so far not been a feasible vaccine candidate and several attempts have therefore been made to construct a vaccine based on selected epitopes (such as the highly conserved TTLNPTIAG (SEQ ID NO: 76) in VD4[36,59]) or based on selected regions rich in neutralizing target epitopes (such as the VD's) from MOMP (WO9406827, U.S. Pat. No. 6,384,206)[60, 61 62, 63 64 51, 65 66].

There has been special focus on VD1, VD2 and VD4 because neutralizing monoclonal antibodies used for serotyping has been shown to map to these regions. These VD regions are targeted by antibodies during natural infection and in line with this, these regions have naturally been the focus of attempts to develop immuno-diagnostics. For example Mygind et al. constructed different polyantigens containing VD regions from different serovariants in the search for a diagnostic tool based on ELISA[67]. This analysis revealed that by increasing the number of serovariants and include the species specific TTLNPTIAG (SEQ ID NO: 76) into one recombinant polyantigen, it was possible to increase the specificity and sensitivity of the assay compared to an assay based on a single serovariant antigen.

Mainly VD4 has attracted interest as an immunogen because this region was shown to contain the highly conserved species-specific epitope TTLNPTIAG (SEQ ID NO: 76) embedded in the variable region. Importantly, this conserved epitope in the VD4 region can elicit a broadly cross-reactive immune response, which is able to neutralize multiple serovars, among them the most prevalent D, E and F (FIG. 2). Peptides representing the VD4 region or the conserved epitope derived from this region have been used for immunization either alone, as chimeric peptides fused to other regions such as VD1 or mixed with T cell epitopes to potentiate the antibody response[60, 68 51, 65 64 69]. All these constructs generated antibodies with some functional capabilities of neutralizing the infection in vitro but in general these strategies suffer from a low immunogenicity and the titres did not translate into in vivo protective efficacy against genital chlamydial challenge.

Reasons for the lack of protection when using these peptide based constructs can be numerous; including route of administration, type of immune response elicited, challenge dose, but most likely reflects that the vaccine molecule is not sufficiently immunogenic for use as a vaccine. The VD4 based strategy furthermore suffers from the limitation that with the exception of the TTLNPTIAG (SEQ ID NO: 76) epitope, these fragments as mentioned above are highly specific for one or two serovariants and a vaccine would accordingly have to be composed of several components to cover the most frequent serovariants causing human disease.

In WO2012172042 it has previously been disclosed that B-cell epitopes within the VD regions, combined with defined T cell (Th1 and Th2) epitopes from non-variable domains of MOMP, could function as a poly-epitope vaccine against *Chlamydia psitattci* serovar D in chickens; in the examples they describe the combination of up to three B-cell epitopes each derived from a VD region from different variable domains of the same serovariant together with several T-cell epitopes. The use of repeats of a variable domain of a surface exposed region of MOMP and using different serovariants is not suggested and thus high titers and a broad response against different serovariants is not obtained.

The object of the current invention is to prepare recombinant fusion molecules that are capable of generating a high titered neutralizing antibody response that is protective against various Ct serovars in vivo. Our invention furthermore describes the combination of these antibody promoting fragments with Ct antigens that are targets for T cells with the aim to provide a vaccine that activate both arms of the immune system.

SUMMARY OF THE INVENTION

The present invention discloses an efficient vaccine against a pathogen, e.g. *Chlamydia trachomatis* (Cf), that incorporates repeats of surface exposed fragments of Ct antigens (homologous immuno-repeats) for maximal antibody responses. In one embodiment of the invention, these surface exposed fragments are extended to cover the flanking region of the surface exposed fragments that may contain T cell epitopes. One example is a defined large fragment representing an extended version of the VD1 or VD4 region from the Ct MOMP antigen and in the immuno-repeat format provides high levels of surface binding and neutralizing antibodies against Ct. In another important embodiment the immuno-repeat technology is used to obtain high titers and a broad response against different serovariants by the fusion of fragments that contain variable B and T cell epitopes from different serovariants (heterologous immuno-repeats). In yet another embodiment of our invention these surface exposed repeats are recombinantly fused with fragments of other surface exposed antigens such as PMPs or OMPs. Finally our invention discloses combinations of these immuno-repeat constructs with strong T cell antigens, such as MOMP(CT681), CT043 or CT004 from Ct that together form a very efficient vaccine against the different infectious stages of Ct infection.

BRIEF DESCRIPTION OF THE SEVERAL VIEWS OF THE DRAWINGS

FIGS. 7A, 7B, 7C-A, 7C-A1, 7C-B, 7C-B1, 7C-C, 7C-C1, 7D-A, 7D-B, 7D-C. Fine specificity of the antibody responses after immunization with a heterologous immuno-repeat of the extended VD4 units from SvD, E, and F (CTH89) compared to constructs composed of a homologous immuno-repeat from (SvE$^{ext}$VD4)*4 and from (SvF$^{ext}$VD4)*4. In FIGS. 7A-7B, the Serovar E sequence shown is SEQ ID NO: 24, and the Serovar F sequence shown is SEQ ID NO: 25. In FIGS. 7C-A through 7D-C, each set of overlapping peptides is NMFTPYIGV through MQI-VSLQLN, corresponding to SEQ ID NO: 195 through SEQ ID NO: 254, respectively. (See Example 3).

DETAILED DISCLOSURE OF THE INVENTION

Figure 1:
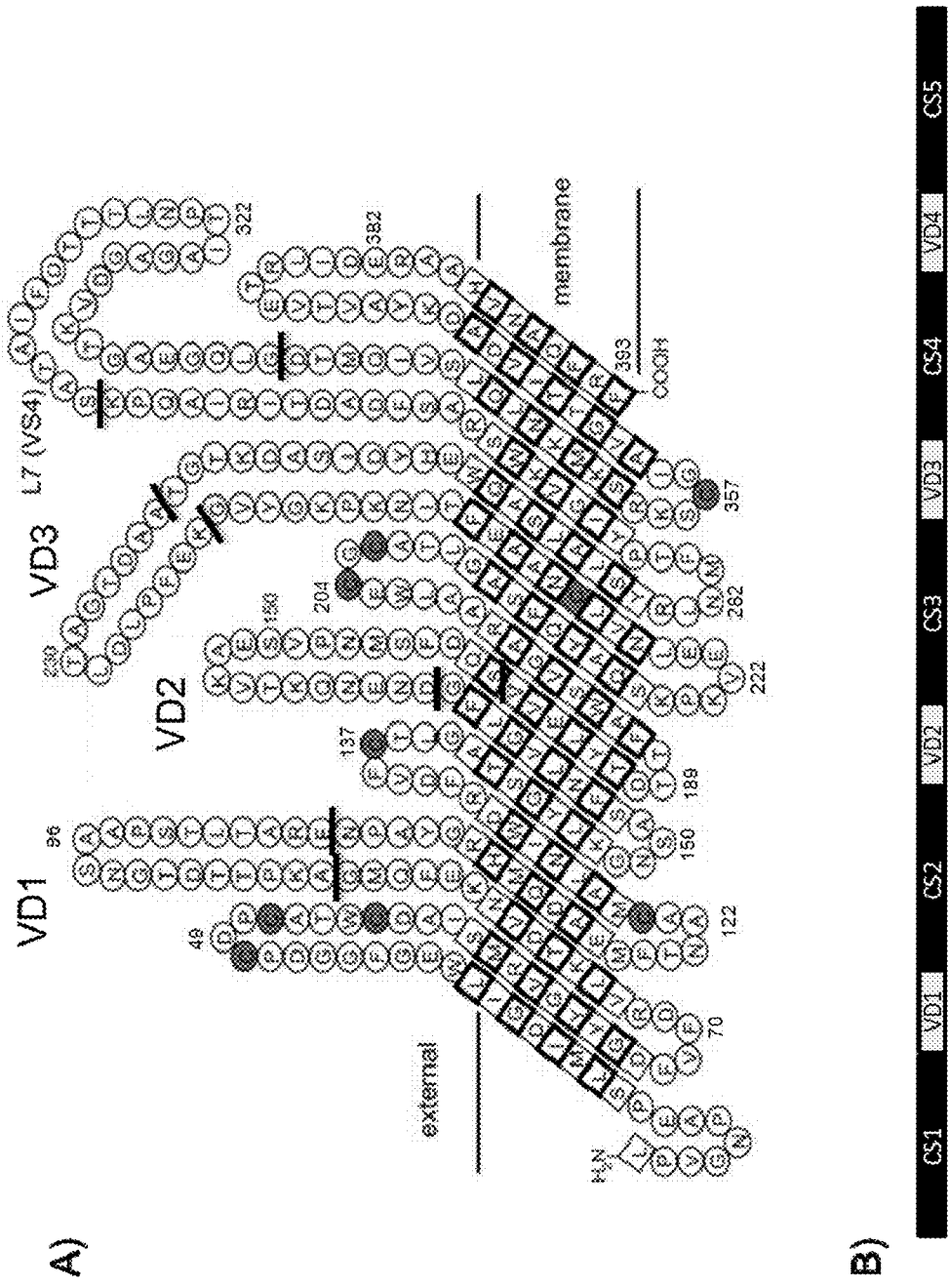
FIG. 1. Model of MOMP (Serovar D, strain: D/B-120) membrane topology adapted from Findlay et al[77]. The VD1, VD2, VD3 and VD4 are marked by black lines in the AA sequence (SEQ ID NO: 68) and in the linear model MOMP depicted interspaced with 5 constant segments (CS).

The invention discloses a polypeptide comprising
a) an amino acid sequence comprising one or more surface exposed fragments of the same outer membrane protein expressed in a serotype of *Chlamydia* sp.; and
b) two or more additional amino acid sequences which is either the same sequence as defined in a) or is the corresponding surface exposed fragments from a variant of said outer membrane protein expressed in a serotype of *Chlamydia* sp., which is different from the serotype in a).

The invention thus discloses polypeptides comprising immuno-repeats, which is 3 or more such as 4 or more repeats of an amino acid sequence comprising an immunogenic portion of a surface exposed region of an outer membrane protein of *Chlamydia* sp. Hence the invention can be described as a polypeptide comprising an amino acid sequence comprising one or more surface expose fragments of the same outer membrane protein expressed in a serotype of *Chlamydia* sp. and two or more such as three or more additional amino acid sequences which is either the same sequence as defined in a) or is the corresponding surface exposed fragments from a variant of said outer membrane protein expressed in a serotype of *Chlamydia* sp., which is different from the serotype in a).

In a preferred embodiment the polypeptide comprises 3 or more different amino acid sequences, where said amino acid sequences each comprises one or more surface exposed fragments from different variants or isotypes of the same outer membrane protein that varies in different *Chlamydia* sp. serotypes, said amino acid sequences derived from different *Chlamydia* sp. serotypes (heterologous immuno-repeats in our terminology), but the invention also discloses a polypeptide comprising 3 or more repetitions of an amino acid sequence, where said amino acid sequence comprises one or more surface exposed fragments of the same outer membrane protein that varies in different *Chlamydia* sp. serotypes, said amino acid sequences derived from the same *Chlamydia* sp. serotype (homologous immuno-repeats in our terminology).

The outer membrane protein is preferable the major outer membrane protein (MOMP) from any *Chlamydia* sp. serotype and the surface exposed fragment is chosen from variable domain 1 (VD1), variable domain 2 (VD2), variable domain 3 (VD3) or variable domain 4 (VD4) of MOMP. The surface exposed fragment can optionally be linearized by substitution of cysteine in the amino acid sequence to prevent disulfide bonds.

A preferred embodiment of the invention is polypeptides comprising immuno-repeats with 3 or more repeats of the variable domain 4 (VD4) of MOMP from any of serovars D, E, F, G, Ia and J of *Chlamydia trachomatis*, where each variable domain consists of an amino acid sequence, which corresponds to the position of amino acid residues Nos. 309-338 in the amino acid sequence of MOMP of *Chlamydia trachomatis* serovar D (SvD) (SEQ ID NO: 68) and where the variable domains in the immune-repeat is independently selected from the group consisting of the VD4 of serovar D, the VD4 of serovar E, the VD4 of serovar F, the VD4 of serovar G, the VD4 of serovar Ia and the VD4 of serovar J of *Chlamydia trachomatis* or has 80% sequence identity herewith.

The amino acid sequence of VD4 from serovar D, E, F, G, Ia and J corresponds to SEQ ID NO: 15-20 respectively. Each variable domain can additionally be flanked/extended on the N-terminal side by either
i) The amino acid sequence EWQASLAL-SYRLNMFTPYIGVKWSRASFDADTIRIAQPK (SEQ ID NO: 21) or
ii) A subsequence of the amino acid sequence in i) said subsequence comprising 1 or more amino acid residues,
On the C-terminal side the variable domain can additionally be flanked/extended by
iii) The amino acid sequence DTMQI-VSLQLNKMKSRKSCGIAVGTTIVDA (SEQ ID NO: 22)
iv) A subsequence of the amino acid sequence in iv) said subsequence comprising 1 or more amino acid residues, or an amino acid sequence which has at least 80% sequence identity herewith.

Hence the preferred embodiment can be described as polypeptides comprising 2-8 different amino acid sequences each derived from MOMP from *Chlamydia trachomatis* which comprises an amino acid sequence defined in formula I:

$$xx_1\text{-VD4-}xx_2 \quad \text{(Formula I)}$$

wherein
VD4 is independently selected from SEQ ID NO: 15-20 or an amino acid sequence which has at least 80% sequence identity herewith,
and
xx$_1$ consists of
i) The amino acid sequence EWQASLAL-SYRLNMFTPYIGVKWSRASFDADTIRIAQPK (SEQ ID NO: 21) or ii) A subsequence of the amino acid sequence in i) said subsequence comprising 1-38 amino acid residues, starting with the C-terminal K in the amino acid sequence in i)
and
$xx_2$ consists of
iii) The amino acid sequence DTMQI-VSLQLNKMKSRKSCGIAVGTTIVDA (SEQ ID NO: 22)
v) A subsequence of the amino acid sequence in iii) said subsequence comprising 1-29 amino acid residues, starting with the N-terminal D in the amino acid sequence in iii).

Examples of fusion proteins comprising immuno-repeats of VD4 of MOMP is indicated by SEQ ID NO: 49-59.

In another embodiment of the invention the polypeptide additionally comprises immuno-repeats of 3 or more variable domain 1 (VD1) of MOMP from any of serovars D, E, F, G, Ia and J of *Chlamydia trachomatis*, each variable domain consisting of an amino acid sequence, which corresponds to position of amino acid residues nos. 91-105 in the amino acid sequence of MOMP of *Chlamydia trachomatis* serovar D (SvD) (SEQ ID NO: 68) and is independently selected from the group consisting of the VD1 of serovar D, the VD1 of serovar E, the VD1 of serovar F, the VD1 of serovar G, the VD1 of serovar Ia and the VD1 of serovar J of *Chlamydia trachomatis* or has 80% sequence identity herewith.

The amino acid sequence of VD1 from serovar D, E, F, G, Ia and J corresponds to SEQ ID NO: 1-6 respectively. Each variable domain can additionally be flanked/extended on the N-terminal side by either
vi) The amino acid sequence SMRVGYYGDFVFDRVLKTDVNKEFQMG (SEQ ID NO: 77)
vii) A subsequence of the amino acid sequence in v) said subsequence comprising 1 or more amino acid residues.

On the C-terminal side the variable domain can additionally be flanked/extended by
viii) The amino acid sequence NPAYGRHMQDAEMFT-NAACMALNIWD (SEQ ID NO: 78)
ix) A subsequence of the amino acid sequence in x) said subsequence comprising 1 or more amino acid residues;
Or an amino acid sequence which has at least 80% sequence identity herewith.

Hence another preferred embodiment can be described as polypeptides comprising 2-8 different amino acid sequences each derived from MOMP from *Chlamydia trachomatis* which comprises an amino acid sequence defined in formula I and additionally comprising an amino acid sequence defined in formula II:

$$yy_1\text{-VD1-}yy_2 \quad \text{(Formula II)}$$

wherein
VD1 is independently selected from SEQ ID NO: 1-6 or an amino acid sequence which has at least 80% sequence identity herewith, and
$yy_1$ consists of
v) The amino acid sequence DAISMRVGYYGDFVFDRVLKTDVNKEFQMG (SEQ ID NO: 7) or
vi) A subsequence of the amino acid sequence in v) said subsequence comprising 1-30 amino acid residues, starting with the C-terminal G in the amino acid sequence in v) and
$yy_2$ consists of
vii) The amino acid sequence NPAYGRHMQDAEMFT-NAA (SEQ ID NO: 8) or
viii) A subsequence of the amino acid sequence in vii) said subsequence comprising 1-18 amino acid residues, starting with the N-terminal N in the amino acid sequence in vii).

Examples of polypeptides comprising immuno-repeats of VD1 is indicated by SEQ ID NO: 9-14 and 45-48.

Further embodiments of the invention comprises additionally comprises a fragment comprising the variable domains 2 (VD2) and/or variable domains 3 (VD3) of MOMP respectively comprising an amino acid sequence defined in formula III and/or formula IV:

$$zz_1\text{-VD2-}zz_2 \quad \text{(Formula III)}$$

$$qq1\text{-VD3-}qq2 \quad \text{(Formula IV)}$$

wherein
VD2 is independently selected from SEQ ID NO: 29-34 or an amino acid sequence which has at least 80% sequence identity herewith,
and
$zz_1$ consists of
ix) The amino acid sequence TLGATSGYLKGN-SASFNLVGLFG (SEQ ID NO: 35) or
x) A subsequence of the amino acid sequence in ix) said subsequence comprising 1-23 amino acid residues, starting with the C-terminal G in the amino acid sequence in ix) and
$zz_2$ consists of
xi) The amino acid sequence WELYTDTTFAWSVGA-RAALWE (SEQ ID NO: 36) or
xii) A subsequence of the amino acid sequence in xi) said subsequence comprising 1-22 amino acid residues, starting with the N-terminal V in the amino acid sequence in xi).
And wherein wherein
VD3 is independently selected from SEQ ID NO: 37-42 or an amino acid sequence which has at least 80% sequence identity herewith,
and
$qq_1$ consists of
xiii) The amino acid sequence ATL-GASFQYAQSKPKVEELNVLCNAAEFTINKPKGYVG (SEQ ID NO: 43) or
xiv) A subsequence of the amino acid sequence in xiii) said subsequence comprising 1-22 amino acid residues, starting with the C-terminal G in the amino acid sequence in xiii)
and
$qq_2$ consists of
xv) The amino acid sequence TGTKDASIDY-HEWQASLALSYRLNMFTPYIGVKWS (SEQ ID NO: 44) or
xvi) A subsequence of the amino acid sequence in xv) said subsequence comprising 1-35 amino acid residues, starting with the N-terminal T in the amino acid sequence in xv).

The immuno-repeats can be heterologous, that is where the variable domain is derived from different serotypes or they can be homologous, that is where the variable domain is derived one serotype. The preferred number of repeats are 2, 3, 4, 5, 6, 7 or 8 repeats.

Furthermore the immuno-repeats in the polypeptides can be linearized, that is cysteine residues are replaced with serine.

The polypeptides comprising immuno-repeats can additionally comprise a moiety that facilitate export of the polypeptide whens produced recombinantly (e.g. signal peptides), a moiety that facilitate purification of the polypeptide (e.g. his-tags) and/or a moiety which enhance the immunogenicity (e.g. a T cell antigen). The T-cell target can be chosen from a Ct antigen such as CT043, CT004, CT414, CT681 or part hereof. Examples of such fusion proteins are indicated by SEQ ID NO 60-67.

A polypeptide according to the invention having the following functional abilities:

a) neutralize *C. trachomatis* serovar D in vitro with a 50% neutralization titer of $10^{-3}$ or less, when tested in an experimental set-up comprising the administering a heterologous immuno-repeats;

b) neutralize *C. trachomatis* serovar D in vivo in at least 50% of the mice at day 7 post infection when tested in a mouse model comprising administering a heterologous immuno-repeats c) broaden the immune response to multiple serovars of *C. trachomatis* in vitro when administering heterologous immuno-repeats.

The present invention also discloses nucleic acids encoding above described polypeptides.

The disclosed polypeptides or nucleic acids are used for the preparation of a pharmaceutical composition such as a vaccine. The vaccine can additionally comprise a pharmacologically acceptable carrier (virus like particles), excipient, adjuvant (e.g. DDA/TDB or alum) or immune modulator. The pharmaceutical composition can be used for prophylactic or therapeutic use against *Chlamydia* sp. Infections, including infections with *Chlamydia trachomatis* or *C. pneumoniae*.

A method for preventing, treating and/or reducing the incidence of *Chlamydia* sp. Infections, including infections with *Chlamydia trachomatis* or *C. pneumoniae*, by administering this pharmaceutical composition is also disclosed.

In the following the invention will be described in more detail and exemplified.

The preferred outer membrane protein is MOMP but may also include other surface exposed antigens from *Chlamydia* species that are targets for humoral responses.

The immuno-repeat from a surface exposed region can be from the same serotype (homologous immuno-repeats) or represent fragments that contain variable epitopes and are derived from different serotypes (heterologous immuno-repeat). In a preferred embodiment the immuno-repeats contain an extended fragment that contains both a variable and a conserved region known to be rich in T cell epitopes.

A preferred surface exposed region of an outer membrane protein is chosen from VD1, VD2, VD3 and VD4 from MOMP.

The amino acid sequences used for constructing the immuno-repeats described in the examples are chosen from table 1, 2 and 3.

The variable domain of VD4 of MOMP can be described as an amino acid sequences as defined as:

La1-Aa2-Aa1-Aa3-La2 wherein

Aa1 consists of the amino acid sequence TTLNPTIAG (SEQ ID NO: 76)(which is conserved for all serovars);

Aa2 is selected from the group consisting of: SATAIFDT (SEQ ID NO: 79)(from serovar D and E), LVTPVVDI (SEQ ID NO: 80)(from serovar F), LAKPVVDI (SEQ ID NO: 81)(from serovar G) and LAEAILDV (SEQ ID NO: 82) (from serovar Ia and J).

When Aa2 is the sequence from serovar D or E, then Aa3 is selected from the sequences set forth in AGDVKTGAEGQLG (SEQ ID NO: 83)(from serovar D) and AGDVKASAEGQLG (SEQ ID NO: 84)(serovar E).

When Aa2 is the sequence from serovar F, then Aa3 is the sequence CGSVAGANTEGQIS (SEQ ID NO: 85)(from serovar F).

When Aa2 is the sequence from serovar G, then Aa3 is the sequence CGSVVAANSEGQIS (SEQ ID NO: 86)(from serovar G).

When Aa2 is the sequence from serovar Ia or J), then Aa3 is selected from KGTWSSAENELA (SEQ ID NO: 87)(from serovar Ia) and KGTWASGSENDLA (SEQ ID NO: 88) (from serovar J)

Figure 2:
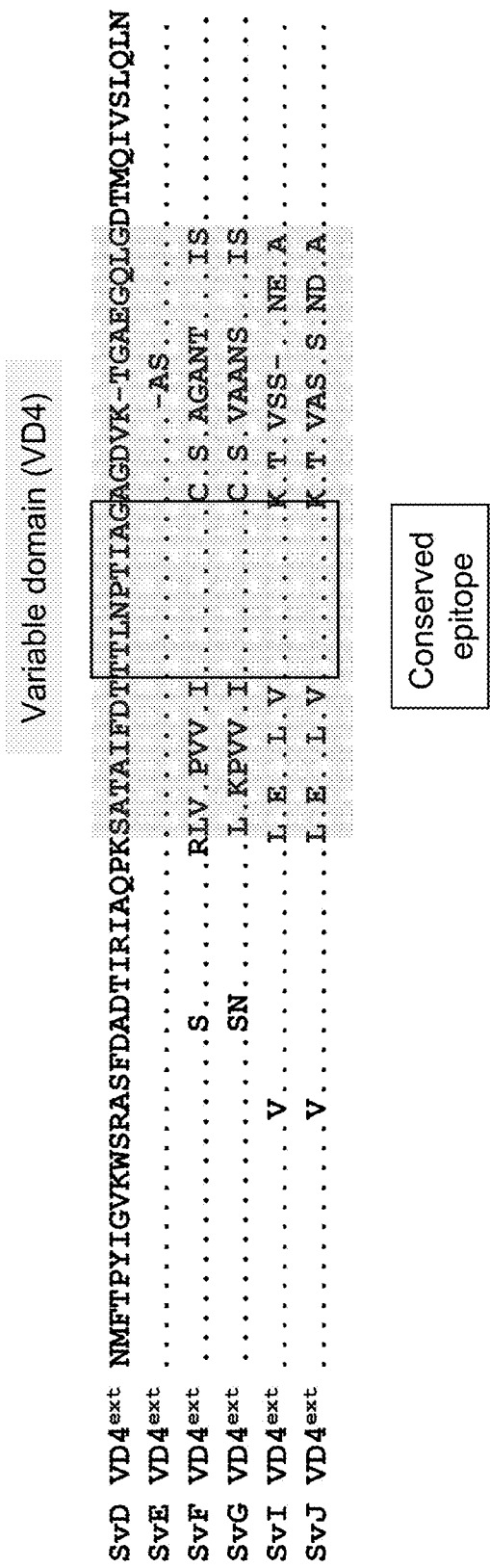
FIG. 2. Alignment of amino acid sequence of Ct MOMP VD4$^{ext}$ for serovars D, E, F, G, Ia and J. The serovar D sequence is used as prototype, and conserved amino acids in other serovars are shown as ".". The variable domain VD4 according to Baehr et al (PNAS, 1988)[36] is shaded in gray and the conserved epitope TTLNPTIAG (SEQ ID NO: 76) is boxed. SvD VD4$^{ext}$ (SEQ ID NO: 23), SvE VD4$^{ext}$ (SEQ ID NO: 24), SvF VD4$^{ext}$ (SEQ ID NO: 25), SVG VD4$^{ext}$ (SEQ ID NO: 26), SvI VD4$^{ext}$ (SEQ ID NO: 27), and SvJ VD4$^{ext}$ (SEQ ID NO: 26) are shown.

The variable domain VD4 of MOMP is depicted in FIG. 2. The immuno-repeats preferably additionally comprises extensions on either sides which are also depicted in FIG. 2.

The N-terminal side of a VD4 domain can be flanked or extended by one or more amino acids from the more conserved and T-cell epitope rich La1, where La1 is the part of VD4 of MOMP which is embedded in the membrane and has the amino acid sequence EWQASLALSYRLNMFTPYIGVKWSRASFDADTIRIAQPK (SEQ ID NO: 21) or an amino acid sequence having 80% sequence identity herewith.

The C-terminal side of a VD4 domain can correspondingly be flanked or extended by one or more amino acids from the more conserved and T-cell epitope rich La2, where La2 is the part of VD4 of MOMP which is embedded in the membrane on the C-terminal side and has the amino acid sequence DTMQIVSLQLNKMKSRKSCGIAVGTTIVDA (SEQ ID NO: 22) or an amino acid sequence having 80% sequence identity herewith.

A similar illustration (see FIG. 1) can describe immuno-repeats comprising the variable domain 1 (VD1) of MOMP with the variable domains (Aa2-Aa1-Aa3) of the various serovars are given by SEQ ID NO: 1-6 in table 1. The corresponding N-terminal and C-terminal extensions (La1 and La2) have the respective amino acid sequences SMRVGYYGDFVFDRVLKTDVNKEFQMG (SEQ ID NO: 77)(La1) and NPAYGRHMQDAEMFTNAACMALNIWD (SEQ ID NO: 78)(La2) which are given in table 2 by SEQ ID NO: 7-8.

Immuno-repeats comprising VD2 and VD3 can in a similar manner be deduced from FIG. 1 and table 1.

Hence above example La1-Aa2-Aa1-Aa3-La2 defines one of the immune-repeat units. If additionally e.g. VD1 is added to a VD4 unit, this can be described as adding one more sequence to make up a larger immune-repeat unit. Hence the polypeptide of the invention comprises 2, 3, 4, 5, 6, 7 or 8 repeats of immune-repeat units.

Definitions

Outer Membrane Proteins

The outer membrane of *Chlamydia* sp. can be isolated by treating intact, purified elementary bodies with detergent such as 2% Sarkosyl followed by ultracentrigation (100,000 g for one hour) which will lead to a supernatant with cytosolic components and a pellet containing the outer membrane as previously described[70]. Outer membrane proteins can then be identified by standard protein techniques, e.g. by mass spectrometry after SDS-PAGE.

Surface Exposed Fragments or Regions

Bacterial surface or membrane proteins comprises trans membrane proteins, secretory and lipoproteins, and anchorless surface proteins. Surface exposed regions on intact bacteria are accessible to antibodies. Methods to identify surface exposed regions of proteins (the 'surfaceome' comprise e.g. biotinylation of the membrane proteins in intact bacteria, followed by isolation of the biotin-labelled fraction using streptavidin. The isolated proteins can then be identified by mass spectrometry. Another approach is to treat intact bacteria with a protease, e.g. trypsin ('shaving') to cleave surface exposed peptides, followed by collection of the released peptides for identification by mass spectrometry.

Variants

Variants of outer membrane proteins provided herein describes proteins encoded by the same gene from different serotypes of Chlamydia sp. A variant protein shares significant homology with a reference polypeptide.

An Isoform of Protein

In the context of the present application an "isoform" of protein is under stood as any of several different forms of the same protein e.g. a protein that has the same function but which is encoded by a different gene and may have small differences in its sequence or arises from either single nucleotide polymorphisms, differential splicing of mRNA, or post-translational modifications. Different serotypes of bacteria may have different isoforms of certain proteins.

Chlamydia Species

By the term "Chlamydia species" is understood a bacterium capable of causing the Chlamydia infection in an animal or in a human being. Examples are C. trachomatis, C. pneumoniae and C. muridarum. Also in animals, several infections with Chlamydia sp. are known, e.g. Chlamydia Suis infecting pigs, and Chlamydiaphila abortus which causes abortion in small ruminants (sheep and goats).

Serovariants, Serovars or Serotypes

Based on the reactivity of specific mono clonal antibodies against and detailed sequence analysis of the MOMP variable regions Ct can be divided into 15 different serovariants and of these serovariants A, B, Ba and C causes Trachoma, D-K causes sexually transmitted disease (STD), L1-L3 causes Lymphogranuloma venerum, and MoPn (C. muridarum) infects mice. Serovariants are sometimes mentioned as serovars or serotypes with the same meaning.

Immuno-Repeats

By immuno-repeats is understood: repetitive units of one or more amino acid sequences comprising an immunogenic portion or fragment of an antigen. The units that are repeated can be described as one or more VD regions, that optionally can be extended as described above, that are repeated e.g. 4 examples with three repeats VD4-VD4-VD4, VD4-VD1-VD4-VD1-VD4-VD1, $VD4_D$-$VD4_D$-$VD4_D$, $VD4_D$-$VD4_F$-$VD4_G$, $VD4_D$-$VD3_E$-$VD4_D$-$VD3_E$-$VD4_D$-$VD3_E$.

Homologous Immuno-Repeat

Repetitive units of one or more amino acid sequences comprising an immunogenic portion or fragment of an antigen from one serovariant only (FIG. 4)

Heterologous Immuno-Repeat

Repetitive units of one or more amino acid sequences comprising an immunogenic portion or fragment encoding the same antigen derived from different serovariants (FIG. 4).

Heterologous Challenge

Refers to the situation where the protein used for vaccination is derived from a different bacterial serovariant than the serovariant used for challenge.

Homologous Challenge

Refers to the situation where the protein used for vaccination is derived from the same bacterial serovariant as the serovariant used for challenge.

MOMP

The Major Outer Membrane Protein (MOMP) of Ct, is expressed during all phases of the developmental life cycle of Ct and constitutes approximately 60% of the total protein content of the *chlamydia* outer membrane. MOMP can be divided into conserved domains interrupted by four highly variable domains (VD1-4 or VS1-4)[59] (FIG. 1)

VD1

Variable domain 1 (VD1) of MOMP as defined by Baehr et al (1988)[36] which corresponds to amino acids 91-105 and make up a highly variable region in MOMP from Ct (Seq no 1-6 VD1 from SvD, E, F, G, Ia and J respectively). The extended VD1 region ($VD1^{ext}$) corresponds to amino acids 57-115 and make-up said highly variable region flanked by highly conserved regions in MOMP from Ct (Seq no 9-14 $VD1^{ext}$ from SvD, E, F, G, Ia and J respectively) (FIG. 3).

VD4

Variable domain 4 of MOMP as defined by Baehr et al (1988)[36] which corresponds to amino acids 309-338 and make up a highly variable region in MOMP from Ct (Seq no 15-20 VD4 from SvD, E, F, G, Ia and J respectively). The extended VD4 region ($VD4^{ext}$) corresponds to amino acids 282-349 and make-up said highly variable region flanked by highly conserved regions in MOMP from Ct (Seq no 23-28 $VD4^{ext}$ from SvD, E F, G, Ia and J respectively).

Linearized

The word "linearized" in the present invention refers to an amino acid chain of any length, including a full-length protein, oligopeptides, short peptides and fragments thereof, wherein the amino acid cysteine has been substituted with serine in order to hinder the cysteine residues to form disulfide bonds.

Neutralizing Epitope

Neutralizing epitope as used herein is intended an amino acid sequence that defines an antigenic determinant which is bound by an antibody and, in the context of infection, reduces infectivity of a Chlamydial load, e.g. by blocking of the bacterial interaction with host cells, which is important in establishing bacterial infection and disease, facilitating bacterial clearance.

Neutralization

Neutralization is to encompass any biological activity of the bacteria, including reduction in the efficiency or ability of the bacterium to establish infection or cause disease or disease symptoms, inhibition of chlamydial EB formation.

Neutralizing Antibodies

Antibodies which bind a neutralizing epitope as described above.

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds.

IFN-γ

By the term "IFN-γ" is understood interferon-gamma. The measurement of IFN-γ is used as an indication of an immunological T-cell response.

Comprise

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

Immunogenic Portion or Fragment

In a preferred embodiment of the invention, the polypeptide comprises an immunogenic portion or fragment of the polypeptide, such as an epitope for a B-cell or T-cell.

The immunogenic portion or fragment of a polypeptide is a part of the polypeptide, which elicits an immune response in an animal or a human being, and/or in a biological sample determined by any of the biological assays described herein. The immunogenic portion or fragment of a polypeptide may be a T-cell epitope or a B-cell epitope. Immunogenic portions or fragments can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence.

In order to identify relevant T-cell epitopes which are recognised during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-γ assay described herein. Another method utilises overlapping oligopeptides for the detection of MHC class II epitopes, preferably synthetic, having a length of e.g. 20 amino acid residues derived from the polypeptide. These peptides can be tested in biological assays (e.g. the IFN-γ assay as described herein) and some of these will give a positive response (and thereby be immunogenic) as evidence for the presence of a T cell epitope in the peptide. For the detection of MHC class I epitopes it is possible to predict peptides that will bind[72] and hereafter produce these peptides synthetic and test them in relevant biological assays e.g. the IFN-γ assay as described herein. The peptides preferably having a length of e.g. 8 to 11 amino acid residues derived from the polypeptide. B-cell epitopes can be determined by analysing the B cell recognition to overlapping peptides covering the polypeptide of interest as e.g. described in Harboe et al[73].

Immunogenic

An immunogenic polypeptide is defined as a polypeptide that induces an immune response in a biological sample or an individual currently or previously infected with a *chlamydia*.

Fusion Proteins

By a fusion protein is understood two or more polypeptides linked together covalently. The fusion proteins can be produced with superior characteristics of the polypeptide. For instance, fusion partners that facilitate export of the fusion protein when produced recombinantly (e.g. signal peptides), fusion partners that facilitate purification of the fusion protein (e.g. his-tags), and fusion partners which enhance the immunogenicity of the fusion protein are all interesting possibilities. The fusion partner can, in order to enhance immunogenicity, be another polypeptide derived from *C. trachomatis*, such as a polypeptide, a polypeptide fragment or at least one T-cell epitope or B cell epitope.

Pharmaceutical Composition

A pharmaceutical composition is defined as any vaccine (both therapeutic and prophylactic) or any diagnostic reagent.

Vaccine, Protein

Another part of the invention pertains to a vaccine composition comprising a fusion protein or a nucleic acid encoding said fusion protein according to the invention. In order to ensure optimum performance of such a vaccine composition it is preferred that it comprises an immunologically and pharmaceutically acceptable carrier, vehicle or adjuvant.

An effective vaccine, wherein a fusion protein of the invention is recognized by a mammal including a human being, will decrease bacterial load in target organs, prolong survival times and/or diminish weight loss after challenge with virulent chlamydial bacteria, compared to non-vaccinated individuals.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyl-dioctadecylammonium bromide (DDA), Quil A, poly I:C, aluminium hydroxide, Freund's incomplete adjuvant, IFNγ, IL-2, IL-12, monophosphoryl lipid A (MPL), Trehalose Dimycolate (TDM), Trehalose Dibephenate (TDB) and muramyl dipeptide (MDP), Monomycolyl glycerol (MMG) or a combination hereof. A preferred combination is a cationic liposome such as DDA combined with TDB and/or poly I:C.

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Therapeutic Vaccine.

The invention also relates to the use of a polypeptide or nucleic acid of the invention for use as therapeutic vaccines as have been described in the literature exemplified by D. Lowry (Lowry et al 1999). Antigens with therapeutic properties may be identified based on their ability to diminish the severity of Ct infection in experimental animals or prevent reactivation of previous infection, when administered as a vaccine. The composition used for therapeutic vaccines can be prepared as described above for vaccines.

Figure 3:
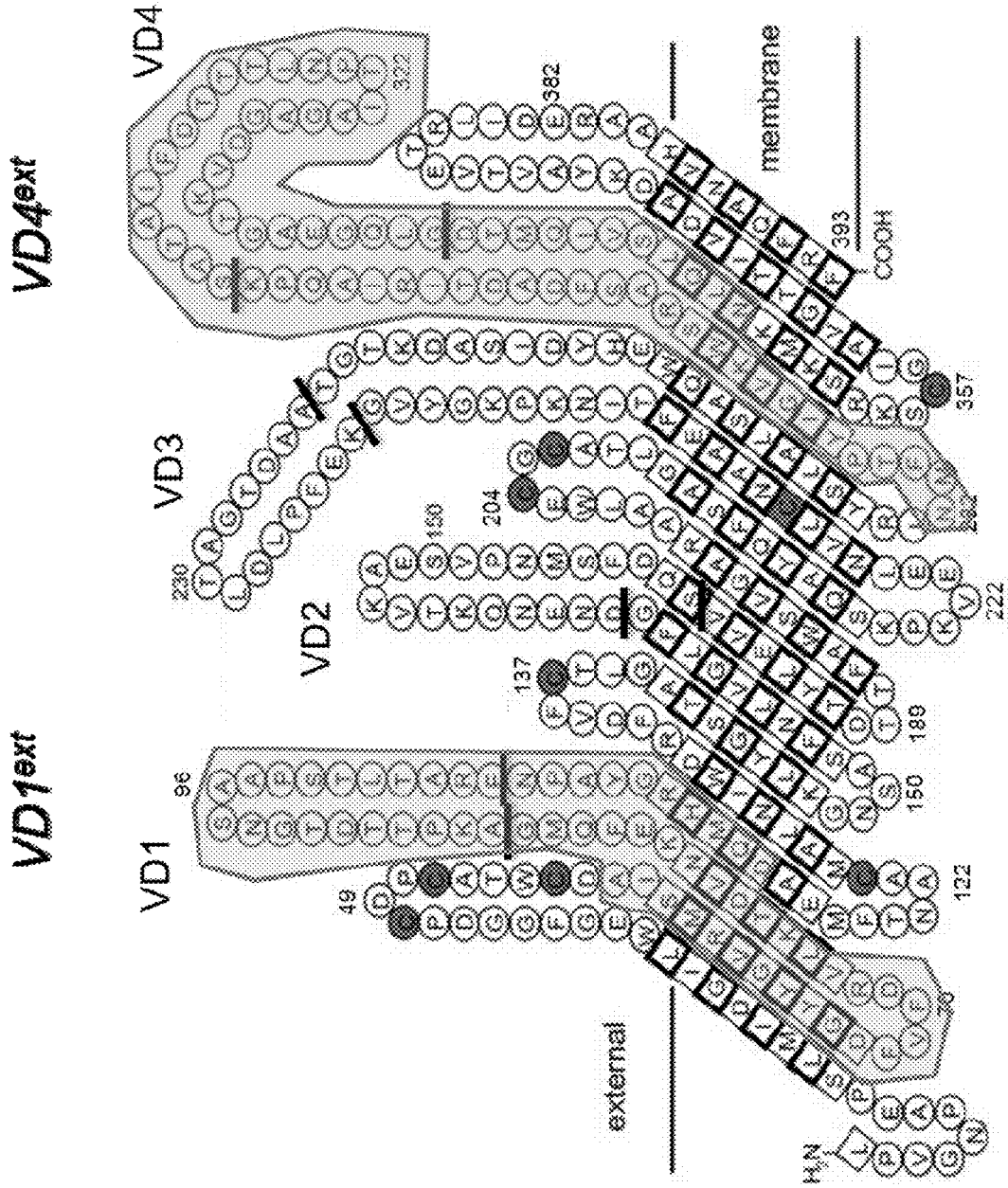
FIG. 3. Model of MOMP (Serovar D, strain: D/B-120) membrane topology adapted from Findlay et al. The VD1ext and VD4$^{ext}$ described in this invention are shown as shaded in the figure. Amino acid sequence shown is SEQ ID NO: 68.
Figure 4:
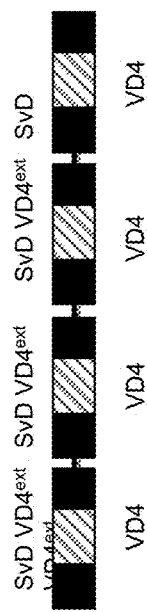
FIG. 4. Illustration of the design of homologous and heterologous immuno-repeats. The immuno-repeats are fusion proteins of e.g. four VD4$^{ext}$ regions, either from the same serovar, homologous immuno-repeats, or from different serovars, heterologous immuno-repeats. The variable VD4 region within each VD4$^{ext}$ region is illustrated as hatched.
Figure 4:
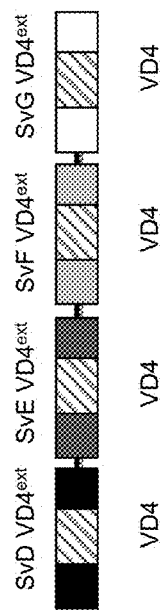

The present invention describes novel highly immunogenic vaccine antigens with broad antibody based neutralizing capacity that protects against different serovariants of *Chlamydia trachomatis*. We demonstrate that repetitive units of defined fragments from the MOMP antigen provide highly immunogenic molecules which we refer to as immuno-repeats. Vaccination with homologous immuno-repeats containing VD4 extended fragments (covers the VD4 variable domain of MOMP and the adjacent conserved flanking regions) in different adjuvants provides very high antibody titers and we demonstrate that these constructs are much more efficient than immunizing with single units of the VD4 extended fragment. The increased effect can be observed both as markedly increased titer, increased antibody targeting of the surface of the bacteria, increased neutralizing capacity, increased and broadened T cell response and increased protection against a challenge with the homologous strain. We furthermore demonstrate that the immuno-repeat technology can be utilized also to improve the protection against and neutralization of other serovariants by constructing heterologous immuno-repeats based on VD4 extended fragments from different serovariants such as serovar D, E, F and G (FIG. 3).

TABLE 1

Description of sequences used in constructing immuno-repeats

| SEQ ID NO | Variable domaines | Description |
|---|---|---|
| 1 | VD1_SvD | Serovar D variable domaine 1 of MOMP |
| 2 | VD1_SvE | Serovar E variable domaine 1 of MOMP |
| 3 | VD1_SvF | Serovar F variable domaine 1 of MOMP |
| 4 | VD1_SvG | Serovar G variable domaine 1 of MOMP |
| 5 | VD1_SvIa | Serovar Ia variable domaine 1 of MOMP |

TABLE 1-continued

Description of sequences used in constructing immuno-repeats

| SEQ ID NO | Variable domaines | Description |
|---|---|---|
| 6 | VD1_SvJ | Serovar J variable domain 1 of MOMP |
| 7 | VD1 N-terminal | VD1 N-terminal extension |
| 8 | VD1 C-terminal | VD1 C-terminal extension |
| 9 | VD1ext_SvD | Serovar D extended VD1 of MOMP |
| 10 | VD1ext_SvE | Serovar E extended VD1 of MOMP |
| 11 | VD1ext_SvF | Serovar F extended VD1 of MOMP |
| 12 | VD1ext_SvG | Serovar G extended VD1 of MOMP |
| 13 | VD1ext_SvIa | Serovar Ia extended VD1 of MOMP |
| 14 | VD1ext_SvJ | Serovar J extended VD1 of MOMP |
| 15 | VD4_SvD | Serovar D variable domaine 4 of MOMP |
| 16 | VD4_SvE | Serovar E variable domaine 4 of MOMP |
| 17 | VD4_SvF | Serovar F variable domaine 4 of MOMP |
| 18 | VD4_SvG | Serovar G variable domaine 4 of MOMP |
| 19 | VD4_SvIa | Serovar Ia variable domaine 4 of MOMP |
| 20 | VD4_SvJ | Serovar J variable domaine 4 of MOMP |
| 21 | VD4 N-terminal | VD4 N-terminal extension |
| 22 | VD4 C-terminal | VD4 C-terminal extension |
| 23 | VD4ext_SvD | Serovar D extended VD4 of MOMP |
| 24 | VD4ext_SvE | Serovar E extended VD4 of MOMP |
| 25 | VD4ext_SvF | Serovar F extended VD4 of MOMP |
| 26 | VD4ext_SvG | Serovar G extended VD4 of MOMP |
| 27 | VD4ext_SvIa | Serovar Ia extended VD4 of MOMP |
| 28 | VD4ext_SvJ | Serovar J extended VD4 of MOMP |
| 29 | VD2_SvD | Serovar D variable domaine 2 of MOMP |
| 30 | VD2_SvE | Serovar E variable domaine 2 of MOMP |
| 31 | VD2_SvF | Serovar F variable domaine 2 of MOMP |
| 32 | VD2_SvG | Serovar G variable domaine 2 of MOMP |
| 33 | VD2_SvIa | Serovar Ia variable domaine 2 of MOMP |
| 34 | VD2_SvJ | Serovar J variable domaine 2 of MOMP |
| 35 | VD2 N-terminal | VD2 N-terminal extension |
| 36 | VD2 C-terminal | VD2 C-terminal extension |
| 37 | VD3_SvD | Serovar D variable domaine 3 of MOMP |
| 38 | VD3_SvE | Serovar E variable domaine 3 of MOMP |
| 39 | VD3_SvF | Serovar F variable domaine 3 of MOMP |
| 40 | VD3_SvG | Serovar G variable domaine 3 of MOMP |
| 41 | VD3_SvIa | Serovar Ia variable domaine 3 of MOMP |
| 42 | VD3_SvJ | Serovar J variable domaine 3 of MOMP |
| 43 | VD3 N-terminal | VD3 N-terminal extension |
| 44 | VD3 C-terminal | VD3 C-terminal extension |

Heterologous immuno-repeats were highly immunogenic but in addition increased the breadth of the antibody responses which was associated with a broader fine specificity of the antibody response (measured by peptide scans) that targets a more diverse repertoire of linear epitopes within the VD4 region than the homologous immuno-repeats. We also demonstrate that highly immunogenic heterologous immuno-repeats can be based on even larger fragments that incorporate fusions of VD1 and VD4 extended fragments and we confirm that in animal models protection promoted by these heterologous immuno-repeats are mediated predominantly by antibodies. As there is a generally recognized need for a strong CMI component (e.g. a T-cell epitope) in an efficient protective immune response against Ct, we have also demonstrated that by fully extending the VD4 region N-terminally to include a T cell rich region, we can generate immune-repeats that combine the ability to generate high tittered neutralizing antibodies with a strong T cell response clearing residual infection in one construct. We have also demonstrated that immune-repeats can be fused to or mixed with T-cell antigens with vaccine potential and that this combination provide both an early antibody mediated protection against Ct as well as an efficient CMI mediated clearance of residual organisms.

MOMP is an important protective antigen with a generally recognized potential in Ct vaccines. The MOMP antigen is however a very complicated antigen to target by vaccines because it has a complex structure with numerous internal disulfide bonds and where important neutralizing epitopes have been exceedingly difficult to expose in recombinant molecules. Adding to this, the MOMP antigen is highly variable and is the basis for the majority of the serovariance found in different strains causing human disease. Any vaccine based on intact MOMP would therefore have to incorporate a number of different versions of the molecule (at least 4-5) to cover the major strains giving rise to disease in humans. As described above the MOMP antigen contains 4 variable regions (VD1-4) of which in particular the VD1 and VD4 contain important neutralizing epitopes but vaccines based on fragments representing these regions have so far failed to induce sufficiently high titers of functional antibodies to have any in vivo effect in animal challenge studies[51 74].

The immuno-repeat technology of the present invention solves this problem: By repeating the important variable VD1 and/or VD4 regions flanked by conserved sequences from the MOMP antigen we have obtained immunogens that promote extraordinary levels of functional antibodies. Surprisingly we also demonstrate that the improved immunogenicity can even be achieved in heterologous immuno-repeat constructs that employs variable regions from different serovars interspaced between conserved fragments and that this strategy produces a broadly neutralizing antibody response that protect against different serovariants. Furthermore, do the immuno-repeat technology provide a large number of relevant T cell epitopes that promote T cells with direct effector function as well as the ability to promote accelerated recall responses to the adjacent B cell epitopes.

Our invention therefore represents a breakthrough in developing efficient Ct vaccines with a broad response and the ability to neutralize different serovars.

It is well known that antigens with a large number of repeats and organized structure are optimal for the activation of the B-cell receptor (BCR), leading to an increased humoral response and a decreased dependence on T-cell help. This was originally reported with natural polysaccharide based antigens from various pathogens (Pneumococcal polysaccharide and *Salmonella* polymerized flagellin) where the repetitive nature of the antigen is assumed to trigger several BCR simultaneously thereby lowering the overall activation threshold which triggers antibody production from plasma B-cells without the need for prior T-cell help. Such antigens are referred to as type 2 T-cell independent B-cell antigens and in artificial systems have been shown to depend on a large number of repeats (typically a minimum of 12-16[75]), that constitute the minimal epitope and are closely located. This is clearly different from our repeat technology where large fragments (69 amino acids, Mw>7 kDa) are repeated and these fragments contain both B-cell and T-cell epitopes[76].

In contrast to previous observations[75], we observe an increase by just 4 repeats which is not further improved by 8 repeats. Importantly, the repetition of a conserved sequence with hypervariable domains inserted, amplify responses not only to the repeated conserved element but importantly to the variable inserts. The molecular mechanism behind this surprising amplification is not completely clear but it most likely relates to the fact that many of the important epitopes are located in the overlap between variable and conserved regions which therefore may allow simultaneous triggering of different BCR's that all share some recognition of the conserved part of the epitope. Although the mechanism is not completely clear the practical consequence is that the heterologous immune-repeat technology allows the synthesis of a multivalent immunogens that promote the generation of a diverse antibody response that targets different serovariants.

Our immuno-repeat constructs provide antigens of an extraordinary immunogenicity compared to previous attempts to use the variable domains from Ct MOMP. All previous vaccines based on VDs of MOMP did, in spite of generating antibodies with some functional capabilities, fail to generate titres that translated into in vivo protection against genital chlamydial challenge[51, 65, 64] In particular the heterologous immuno-repeat strategy solves a very fundamental problem seen for many pathogens and that is how to promote diverse antibody responses to diverse and variable antigens.

TABLE 2

Immuno-repeats

| SEQ ID NO | Polypeptide names | Description |
|---|---|---|
| 45 | CTH87 (CT681_VD1ext_VD4ext_SvD) | Fusion of VD1-VD4 of serovar D |
| 46 | CTH88 (CT681_lin_VD1ext_VD4ext_SvD_E_F) | Heterologous immune repeat of VD1-VD4 |
| 47 | CTH88ext = CTH69 (CT681_lin_VD1ext_VD4ext_SvD_E_F_ext) | Same as SEQ ID NO 46 with longer flanking region. |
| 48 | CTH72 (CT681_lin_VD1ext_VD4ext_SvD_E_F_G_Ia_J_ext) | Same as seq id no 47 additionally with VD1ext and VD4ext from SvG, SvIa and SvJ |
| 49 | CTH89 (CT681_lin_VD4ext_SvD_E_F) | Heterologous immune repeat of VD4 |
| 50 | CTH181 (CT681_VD4ext_SvE) | Same as SEQ ID NO 24 |
| 51 | CTH182 (CT681_lin_VD4ext_F) | Same as SEQ ID NO 25 linearized |
| 52 | CTH183 (CT681_VD4ext_F) | Same as SEQ ID NO 25 |
| 53 | CTH518 (CT681_Lin_VD4ext_D_E_F_G) | Heterologous immune repeat of VD4 |
| 54 | CTH518ext = CTH70 (CT681_lin_VD4ext_SvD_E_F_G_ext) | Same as SEQ ID NO 53 with longer flanking regions |
| 55 | CTH71 (CT681_lin_VD4ext_SvD_E_F_G_Ia_J_ext) | Same as seq id no 54 additionally with VD1ext and VD4ext from SvIa and SvJ |
| 56 | CTH524 (CT681_lin_4_VD4ext_F) | Same as SEQ ID NO 59 linearized |
| 57 | CTH526 (CT681_8_VD4ext_SvE) | Homologous immune repeat of VD4 (8x) |
| 58 | CTH527 (CT681_4_VD4ext_SvE) | Homologous immune repeat of VD4 (4x) |
| 59 | CTH529 (CT681_4_VD4ext_F) | Homologous immune repeat of VD4 (4x) |

TABLE 3

Examples of immuno-repeats fused with T-cell antigens

| SEQ ID NO | Fusions of immuno repeats with T-cell antigens (all his-tagged) |
|---|---|
| 60 | CTH91 (CT043-CT414p-CT681_lin_VD1ext_VD4ext_SvD_E_F) |
| 61 | CTH93 (CT043_CT414p_CT681_Lin_56-281_VD4ext_D) |
| 62 | CTH520 (CT681_56-281_VD4ext_D) |
| 63 | CTH521 (CT681_Lin_56-281_VD4ext_D) |
| 64 | CTH522 (CT681_lin_56-281_VD4ext_D_E_F_G) |
| 65 | CTH531 (CT414_CT043_CT043_681_lin_56-281_VD4ext_SvD_E_F_G) |
| 66 | CTH533 (CT043_CT043_CT681_lin_VD4ext_SvD_E_F_G) |
| 67 | CTH534 (CT043_CT043_CT004_CT681_lin_VD4ext_SvD_E_F_G) |
| 68 | CT681_SvD |
| 69 | CTH285 (VD4_lin_SvD, E, F, G) |
| 70 | CTH286 (VD4 classic + 7_lin_SvD, E, F, G) |

TABLE 4

Overlapping peptides of VD4 from serovar E

| VD4 serovar E peptides (20mers) | Amino acid sequence | SEQ ID NO |
|---|---|---|
| CT681_25_SvE | DASIDYHEWQASLALSYRLN | 89 |
| CT681_26_SvE | ASLALSYRLNMFTPYIGVKW | 90 |
| CT681_27_SvE | MFTPYIGVKWSRASFDADTI | 91 |
| CT681_28_SvE | SPASFDADTIRIAQPKSATA | 92 |
| CT681_29_SvE | RIAQPKSATAIFDTTTLNPT | 93 |
| CT681_30_SvE | IFDTTTLNPTIAGAGDVKAS | 94 |
| CT681_31_SvE | IAGAGDVKASAEGQLGDTMQ | 95 |
| CT681_32_SvE | AEGQLGDTMQIVSLQLNKMK | 96 |

TABLE 5

Overlapping peptides of VD4 from serovar F

| Serovar F peptides (20mers) | Amino acid sequence | SEQ ID NO |
|---|---|---|
| CT681_25_SvF | DASIDYHEWQASLSLSYRLN | 97 |
| CT681_26_SvF | ASLSLSYRLNMFTPYIGVKW | 98 |
| CT681_27_SvF | MFTPYIGVKWSRASFDSDTI | 99 |
| CT681_28_SvF | SRASFDSDTIRIAQPRLVTP | 100 |
| CT681_29_SvF | RIAQPRLVTPVVDITTLNPT | 101 |
| CT681_30_SvF | VVDITTLNPTIAGCGSVAGA | 102 |

TABLE 5-continued

Overlapping peptides of VD4 from serovar F

| Serovar F peptides (20mers) | Amino acid sequence | SEQ ID NO |
|---|---|---|
| CT681_31_SvF | IAGCGSVAGANTEGQISDTMQ | 103 |
| CT681_32_SvF | TEGQISDTMQIVSLQLNKMK | 104 |

TABLE 6

Overlapping peptides of VD4 from serovar D

| VD4 serovar D peptides (9mers) | Amino acid sequence | SEQ ID NO | VD4 serovar D peptides (9mers) | Amino acid sequence | SEQ ID NO |
|---|---|---|---|---|---|
| VD4_P1_SvD | SRASFDADT | 105 | VD4_P24_SvD | TTTLNPTIA | 128 |
| VD4_P2_SvD | RASFDADTI | 106 | VD4_P25_SvD | TTLNPTIAG | 76 |
| VD4_P3_SvD | ASFDADTIR | 107 | VD4_P26_SvD | TLNPTIAGA | 129 |
| VD4_P4_SvD | SFDADTIRI | 108 | VD4_P27_SvD | LNPTIAGAG | 130 |
| VD4_P5_SvD | FDADTIRIA | 109 | VD4_P28_SvD | NPTIAGAGD | 131 |
| VD4_P6_SvD | DADTIRIAQ | 110 | VD4_P29_SvD | PTIAGAGDV | 132 |
| VD4_P7_SvD | ADTIRIAQP | 111 | VD4_P30_SvD | TIAGAGDVK | 133 |
| VD4_P8_SvD | DTIRIAQPK | 112 | VD4_P31_SvD | IAGAGDVKT | 134 |
| VD4_P9_SvD | TIRIAQPKS | 113 | VD4_P32_SvD | AGAGDVKTG | 135 |
| VD4_P10_SvD | IRIAQPKSA | 114 | VD4_P33_SvD | GAGDVKTGA | 136 |
| VD4_P11_SvD | RIAQPKSAT | 115 | VD4_P34_SvD | AGDVKTGAE | 137 |
| VD4_P12_SvD | IAQPKSATA | 116 | VD4_P35_SvD | GDVKTGAEG | 138 |
| VD4_P13_SvD | AQPKSATAI | 117 | VD4_P36_SvD | DVKTGAEGQ | 139 |
| VD4_P14_SvD | QPKSATAIF | 118 | VD4_P37_SvD | VKTGAEGQL | 140 |
| VD4_P15_SvD | PKSATAIFD | 119 | VD4_P38_SvD | KTGAEGQLG | 141 |
| VD4_P16_SvD | KSATAIFDT | 120 | VD4_P39_SvD | TGAEGQLGD | 142 |
| VD4_P17_SvD | SATAIFDTT | 121 | VD4_P40_SvD | GAEGQLGDT | 143 |
| VD4_P18_SvD | ATAIFDTTT | 122 | VD4_P41_SvD | AEGQLGDTM | 144 |
| VD4_P19_SvD | TAIFDTTTL | 123 | VD4_P42_SvD | EGQLGDTMQ | 145 |
| VD4_P20_SvD | AIFDTTTLN | 124 | VD4_P43_SvD | GQLGDTMQI | 146 |
| VD4_P21_SvD | IFDTTTLNP | 125 | VD4_P44_SvD | QLGDTMQIV | 147 |
| VD4_P22_SvD | FDTTTLNPT | 126 | VD4_P45_SvD | LGDTMQIVS | 148 |
| VD4_P23_SvD | DTTTLNPTI | 127 | | | |

TABLE 7

Overlapping peptides of VD4 from serovar F

| VD4 serovar F peptides (9mers) | Amino acid sequence | SEQ ID NO | VD4 serovar F peptides (9mers) | Amino acid sequence | SEQ ID NO |
|---|---|---|---|---|---|
| VD4_P1_SvF | SRASFDSDT | 149 | VD4_P24_SvF | ITTLNPTIA | 172 |
| VD4_P2_SvF | RASFDSDTI | 150 | VD4_P25_SvF | TTLNPTIAG | 76 |
| VD4_P3_SvF | ASFDSDTIR | 151 | VD4_P26_SvF | TLNPTIAGC | 173 |

TABLE 7-continued

Overlapping peptides of VD4 from serovar F

| VD4 serovar F peptides (9mers) | Amino acid sequence | SEQ ID NO | VD4 serovar F peptides (9mers) | Amino acid sequence | SEQ ID NO |
|---|---|---|---|---|---|
| VD4_P4_SvF  | SFDSDTIRI | 152 | VD4_P27_SvF | LNPTIAGCG | 174 |
| VD4_P5_SvF  | FDSDTIRIA | 153 | VD4_P28_SvF | NPTIAGCGS | 175 |
| VD4_P6_SvF  | DSDTIRIAQ | 154 | VD4_P29_SvF | PTIAGCGSV | 176 |
| VD4_P7_SvF  | SDTIRIAQP | 155 | VD4_P30_SvF | TIAGCGSVA | 177 |
| VD4_P8_SvF  | DTIRIAQPR | 156 | VD4_P31_SvF | IAGCGSVAG | 178 |
| VD4_P9_SvF  | TIRIAQPRL | 157 | VD4_P32_SvF | AGCGSVAGA | 179 |
| VD4_P10_SvF | IRIAQPRLV | 158 | VD4_P33_SvF | GCGSVAGAN | 180 |
| VD4_P11_SvF | RIAQPRLVT | 159 | VD4_P34_SvF | CGSVAGANT | 181 |
| VD4_P12_SvF | IAQPRLVTP | 160 | VD4_P35_SvF | GSVAGANTE | 182 |
| VD4_P13_SvF | AQPRLVTPV | 161 | VD4_P36_SvF | SVAGANTEG | 183 |
| VD4_P14_SvF | QPRLVTPVV | 162 | VD4_P37_SvF | VAGANTEGQ | 184 |
| VD4_P15_SvF | PRLVTPVVD | 163 | VD4_P38_SvF | AGANTEGQI | 185 |
| VD4_P16_SvF | RLVTPVVDI | 164 | VD4_P39_SvF | GANTEGQIS | 186 |
| VD4_P17_SvF | LVTPVVDIT | 165 | VD4_P40_SvF | ANTEGQISD | 187 |
| VD4_P18_SvF | VTPVVDITT | 166 | VD4_P41_SvF | NTEGQISDT | 188 |
| VD4_P19_SvF | TPVVDITTL | 167 | VD4_P42_SvF | TEGQISDTM | 189 |
| VD4_P20_SvF | PVVDITTLN | 168 | VD4_P43_SvF | EGQISDTMQ | 190 |
| VD4_P21_SvF | VVDITTLNP | 169 | VD4_P44_SvF | GQISDTMQI | 191 |
| VD4_P22_SvF | VDITTLNPT | 170 | VD4_P45_SvF | QISDTMQIV | 192 |
| VD4_P23_SvF | DITTLNPTI | 171 | VD4_P46_SvF | ISDTMQIVS | 193 |

TABLE 8

CT681 amino acid sequences

| SEQ ID NO | Amino acid sequences of MOMP (CT681) from different serovars |
|---|---|
| 68 | CT681_SvD |
| 71 | CT681_SvE |
| 72 | CT681_SvF |
| 73 | CT681_SvG |
| 74 | CT681_SvIa |
| 75 | CT681_SvJ |

The nucleic acid of the invention, that is nucleic acid encoding above mentioned fusion proteins, may be used for effecting in vivo expression of immunogenic polypeptides, i.e. the nucleic acid may be used in so-called DNA vaccines as reviewed in Ulmer et al 1993, which is included by reference.

In the construction and preparation of plasmid DNA encoding a fusion polypeptide to be used defined for DNA vaccination a host strain such as E. coli can be used. Plasmid DNA can then be prepared from overnight cultures of the host strain carrying the plasmid of interest, and purified using e.g. the Qiagen Giga-Plasmid column kit (Qiagen, Santa Clarita, Calif., USA) including an endotoxin removal step. It is essential that plasmid DNA used for DNA vaccination is endotoxin free.

Hence, the invention also relates to a vaccine comprising a nucleic acid according to the invention, the vaccine effecting in vivo expression of the immunogenic polypeptide by an animal, including a human being, to whom the vaccine has been administered, the amount of expressed polypeptide being effective to confer substantially increased resistance to infections caused by virulent bacteria in an animal, including a human being.

The efficacy of such a DNA vaccine can possibly be enhanced by administering the gene encoding the expression product together with a DNA fragment encoding a polypeptide which has the capability of modulating an immune response.

One possibility for effectively activating a cellular immune response can be achieved by expressing the relevant immunogenic polypeptide in a non-pathogenic microorganism or virus. Well-known examples of such microorganisms are *Mycobacterium bovis* BCG, *Salmonella* and Pseudomona and examples of viruses are Vaccinia Virus and Adenovirus.

Therefore, another important aspect of the present invention is an improvement of the live BCG vaccine presently available, wherein one or more copies of a DNA sequence encoding one or more fusion polypeptides as defined above has been incorporated into the genome of the micro-organism in a manner allowing the micro-organism to express and secrete the fusion polypeptide. The incorporation of more than one copy of a nucleic acid sequence of the invention is contemplated to enhance the immune response.

Another possibility is to integrate the DNA encoding the fusion polypeptide according to the invention in an attenuated virus such as the Vaccinia virus or Adenovirus (Rolph et al 1997). The recombinant vaccinia virus is able to enter within the cytoplasma or nucleus of the infected host cell and the fusion polypeptide of interest can therefore induce an immune response, which is envisioned to induce protection against TB.

Although DNA vaccines were developed more than 16 years ago, clinical trials preceding stage I and II in humans are rare. Two veterinary DNA vaccines however, have been licensed; one for West Nile Virus (in horse) and a second for Infectious Hematopoetic Necrosis virus in Salmon. This demonstrates that DNA vaccines can have good protective effects and that new DNA vaccines are not limited by the size of the animal or species. The great success with DNA vaccines observed for the murine model for first generation DNA vaccines did not translate well to humans, nonetheless; researchers have recently demonstrated protective antibodies levels by a single dose of gene gun administrated HA DNA vaccine to humans.

"Nucleic acid immunization" or the commonly preferred name "DNA vaccines" are the inoculation of antigen encoding DNA or RNA as expression cassettes or expression vectors or incorporated into viral vectors with the purpose of inducing immunity to the gene product. Thus, in our definition of DNA vaccines we include all kinds of delivery systems for the antigen encoding DNA or RNA. The vaccine gene can be in form of circular plasmid or a linear expression cassette with just the key features necessary for expression (promotor, the vaccine gene and polyadenylation signal). Delivery systems may most often be naked DNA in buffer with or without adjuvant, DNA coupled to nanoparticles and/or formulated into adjuvant containing compounds or inserted into live viral or bacterial vectors such as Adenovirus, adeno associated virus, alphavirus, poxviruses, herpes virus etc. DNA vaccines hold great promise since they evoke both humoral and cell-mediated immunity, without the same dangers associated with live virus vaccines. In contrast to live attenuated virus vaccines DNA vaccines may be delivered to same or different tissue or cells than the live virus that has to bind to specific receptors. The production of antigens in their native forms improves the presentation of the antigens to the host immune system. Unlike live attenuated vaccines, DNA vaccines are not infectious and cannot revert to virulence.

DNA vaccines offer many advantages over conventional vaccines. It can be produced in high amounts in short time, abolishing the need for propagation in eggs, it is cost-effective, reproducible and the final product does not require cold storage conditions, because DNA is stable and resistant to the extremes of temperature. All currently licensed inactivated vaccines are efficient at inducing humoral antibody responses but only live attenuated virus vaccines efficiently induce a cytotoxic cellular response as well. DNA vaccines also have this ability and the induced response therefore may better mimic the natural response to viral infection than inactivated vaccines in respect to specificity and antibodies isotypes.

DNA vaccines induce an immune response which is comparable to the response acquired by natural virus infection by activating both humoral and cell-mediated immunity. The broad response to DNA vaccines is a result of the encoded genes being expressed by the transfected host cell, inducing both a Th1 and Th2 immune responses. The production of antigens in their native form improves the presentation of the antigens to the host immune system.

The two most common types of DNA vaccine administration are saline injection of naked DNA and gene gun DNA inoculations (DNA coated on solid gold beads administrated with helium pressure). Saline intra muscular injections of DNA preferentially generates a Th1 IgG2a response while gene gun delivery tends to initiate a more Th2 IgG1 response. Intramuscular injected plasmids are at risk of being degraded by extracellular deoxyribonucleases, however, the responses induced are often more long-lived than those induced by the gene gun method. Vaccination by gene gun delivery of DNA, to the epidermis, has proven to be the most effective method of immunization, probably because the skin contains all the necessary cells types, including professional antigen presenting cells (APC), for eliciting both humoral and cytotoxic cellular immune responses (Langerhans and dendritic cells). Complete protection from a lethal dose of influenza virus has been obtained with as little as 1 µg DNA in mice. The standard DNA vaccine vector consists of the gene of interest cloned into a bacterial plasmid engineered for optimal expression in eukaryotic cells. Essential features include; an origin of replication allowing for production in bacteria, a bacterial antibiotic resistance gene allowing for plasmid selection in bacterial culture, a strong constitutive promotor for optimal expression in mammalian cells (promoters derived from cytomegalovirus (CMV) or simian virus provide the highest gene expression), a polyadenylation sequence to stabilise the mRNA transcripts, such as bovine growth hormone (BHG) or simian virus polyadenylation, and a multiple cloning site for insertion of an antigen gene. An intron A sequence improves expression of genes remarkably. Many bacterial DNA vaccine vectors contain unmethylated cytidinephosphate-guanosine (CpG) dinucleotide motifs that may elicit strong innate immune responses in the host. In recent years there have been several approaches to enhance and customise the immune response to DNA vaccine constructs (2nd generation DNA vaccines). For instance dicistronic vectors or multiple geneexpressing plasmids have been used to express two genes simultaneously. Specific promoters have been engineered that restrict gene expression to certain tissues, and cytokine/antigen fusion genes have been constructed to enhance the immune response. Furthermore, genes may be codon optimised for optimal gene expression in the host and naïve leader sequences may be substituted with optimised leaders increasing translation efficiency.

The administration of DNA vaccine can be by saline or buffered saline injection of naked DNA or RNA, or injection of DNA plasmid or linear gene expressing DNA fragments coupled to particles, or inoculated by gene gun or delivered by a viral vector (virus like particle) such as Adenovirus, Modified vaccinia virus Ankara (MVA), Vaccinia, Adeno-associated virus (AAV), Alphavirus etc.

In one embodiment is a polypeptide comprising a) an amino acid sequence comprising one or more surface exposed fragments of the same outer membrane protein expressed in a serotype of *Chlamydia* sp.; and b) two or more additional amino acid sequences which is either the same sequence as defined in a) or is the corresponding surface exposed fragments from a variant of said outer membrane protein expressed in a serotype of *Chlamydia* sp., which is different from the serotype in a).

In a further embodiment is a polypeptide comprising 3 or more different amino acid sequences, where said amino acid sequences each comprises one or more surface exposed fragments from different variants of the same outer membrane protein that varies in different *Chlamydia* sp. serotypes, said amino acid sequences derived from different *Chlamydia* sp. serotypes.

In another further embodiment is a polypeptide comprising 3 or more repetitions of an amino acid sequence, where said amino acid sequence comprises one or more surface exposed fragments of the same outer membrane protein that varies in different *Chlamydia* sp. serotypes, said amino acid sequences derived from the same *Chlamydia* sp. serotype.

A polypeptide as described bove is provided, wherein the outer membrane protein is MOMP from any serotype. The outer membrane protein may be MOMP from serotype D, E, F, G, Ia or J of *Chlamydia trachomatis* or *C. pneumoniae*. Still further, a polypeptide may comprise one or more of the variable domains 1, 2, 3, 4 of MOMP. These variable domain sequences may optionally be linearized. These variable domain sequences may comprise the variable domains 4 (VD4) of MOMP, and may be placed next to each other or be spaced with a linker. In an embodiment thereof is a polypeptide comprising an amino acid sequence defined in formula I:

$$xx_1\text{-VD4-}xx_2 \qquad \text{(Formula I)}$$

wherein
VD4 is independently selected from SEQ ID NO: 15-20 or an amino acid sequence which has at least 80% sequence identity herewith
and
$xx_1$ consists of
i) The amino acid sequence EWQASLAL-SYRLNMFTPYIGVKWSRASFDADTIRIAQPK (SEQ ID NO: 21) or
ii) A subsequence of the amino acid sequence in i) said subsequence comprising 1-38 amino acid residues, starting with the C-terminal K in the amino acid sequence in i)
and
$xx_2$ consists of
iii) The amino acid sequence DTMQI-VSLQLNKMKSRKSCGIAVGTTIVDA (SEQ ID NO: 22) or
iv) A subsequence of the amino acid sequence in iii) said subsequence comprising 1-29 amino acid residues, starting with the N-terminal D in the amino acid sequence in iii).

In these embodiments, the sequences may be chosen from SEQ ID NO: 23-28, 49-59.

Polypeptides according to any of the above embodiments are also provided additionally comprising a fragment comprising the variable domains 1 (VD1) of MOMP and wherein the amino acid sequences comprising VD1 of MOMP are placed next to each other or are spaced with a linker. In an embodiment thereof is a polypeptide comprising an amino acid sequence defined in formula II:

$$yy_1\text{-VD1-}yy_2 \qquad \text{(Formula II)}$$

wherein
VD1 is independently selected from SEQ ID NO: 1-6 or an amino acid sequence which has at least 80% sequence identity herewith and
$yy_1$ consists of
v) The amino acid sequence DAISMRVGYYGDFVFDRVLKTDVNKEFQMG SEQ ID NO: 7) or vi) A subsequence of the amino acid sequence in v) said subsequence comprising 1-30 amino acid residues, starting with the C-terminal G in the amino acid sequence in v)
and
$yy_2$ consists of
vii) The amino acid sequence NPAYGRHMQDAEMFT-NAA (SEQ ID NO: 8) or
viii) A subsequence of the amino acid sequence in vii) said subsequence comprising 1-18 amino acid residues, starting with the N-terminal N in the amino acid sequence in vii).

In these embodiments, the sequences may be chosen from SEQ ID NO: 9-14, 45-48.

Polypeptides according to any of the above embodiments are also provided comprising a fragment comprising the variable domains 2 (VD2) of MOMP and wherein the amino acid sequences comprising VD2 of MOMP are placed next to each other or are spaced with a linker. In an embodiment thereof is a polypeptide comprising an amino acid sequence defined in formula III:

$$zz_1\text{-VD2-}zz_2 \qquad \text{(Formula III)}$$

wherein
VD2 is independently selected from SEQ ID NO: 29-34 or an amino acid sequence which has at least 80% sequence identity herewith,
and
$zz_1$ consists of
ix) The amino acid sequence TLGATSGYLKGN-SASFNLVGLFG (SEQ ID NO: 35) or
x) A subsequence of the amino acid sequence in ix) said subsequence comprising 1-23 amino acid residues, starting with the C-terminal G in the amino acid sequence in ix)
and
$xx_2$ consists of
xi) The amino acid sequence WELYTDTTFAWSVGA-RAALWE (SEQ ID NO: 36) or
xii) A subsequence of the amino acid sequence in xi) said subsequence comprising 1-22 amino acid residues, starting with the N-terminal V in the amino acid sequence in xi).

Polypeptides according to any of the above embodiments are also provided comprising a fragment comprising the variable domains 3 (VD3) of MOMP and wherein the amino acid sequences comprising VD3 of MOMP are placed next to each other or are spaced with a linker. In an embodiment thereof is a polypeptide comprising an amino acid sequence defined in formula IV:

$$qq_1\text{-VD3-}qq_2 \qquad \text{(Formula IV)}$$

wherein
VD3 is independently selected from SEQ ID NO: 37-42 or an amino acid sequence which has at least 80% sequence identity herewith,
and
$qq_1$ consists of
xiii) The amino acid sequence ATL-GASFQYAQSKPKVEELNVLCNAAEFT-INKPKGYVG (SEQ ID NO: 43) or
xiv) A subsequence of the amino acid sequence in xiii) said subsequence comprising 1-22 amino acid residues, starting with the C-terminal G in the amino acid sequence in xiii)

and qq₂ consists of xv) The amino acid sequence TGTKDASIDY-HEWQASLALSYRLNMFTPYIGVKWS (SEQ ID NO: 44) or xvi) A subsequence of the amino acid sequence in xv) said subsequence comprising 1-35 amino acid residues, starting with the N-terminal T in the amino acid sequence in xv).

Polypeptides according to any of the above embodiments are also provided comprising a moiety that facilitate export of the polypeptide when produced recombinantly (e.g. signal peptides), a moiety that facilitate purification of the fusion protein (e.g. his-tags) and/or a moiety which enhance the immunogenicity (e.g. a T cell antigen). In some embodiments, the enhancer of immunogenicity is an additional T-cell target which is chosen from a Ct antigen such as CT043, CT004, CT414, CT681 or part hereof. In these embodiments, said sequences may be chosen from SEQ ID NO: 60-68.

Still further provided are polypeptides according to any of the above embodiments, said polypeptide having the ability to a) neutralize *C. trachomatis* serovar D in vitro with a 50% neutralization titer of $10^{-3}$ or less, when tested in an experimental set-up comprising the administering heterologous immuno-repeats b) neutralize *C. trachomatis* serovar D in vivo in at least 50% of the mice at day 7 post infection when tested in a mouse model comprising administering heterologous immuno-repeats c) broaden the immune response to multiple serovars of *C. trachomatis* in vitro when administering a heterologous of immuno-repeats Still further provided are nucleic acids encoding a polypeptides according to any of the above embodiments.

Also provided are pharmaceutical compositions comprising a polypeptide according to any of the above embodiments or a nucleic acid according to any of the above embodiments. The pharmaceutical compositions may be vaccines. The pharmaceutical compositions may additionally comprise a pharmacologically acceptable carrier, excipient, adjuvant or immune modulator. The pharmaceutical compositions may include an adjuvant selected from DDA/TDB or alum. In further embodiments, pharmaceutical compositions may include a carrier that is a virus-like particle.

Still further provided are pharmaceutical compositions comprising a polypeptide according to any of the above embodiments or a nucleic acid according to any of the above embodiments for prophylactic or therapeutic use against *Chlamydia* sp. infections, including infections with *Chlamydia trachomatis* or *C. pneumoniae*.

Methods for preventing, treating and/or reducing the incidence of *Chlamydia* sp. infections, including infections with *Chlamydia trachomatis* and *C. pneumoniae*, said method comprising administering a pharmaceutical composition described herein are also provided.

Material and Methods

Cultivation of *C. trachomatis*

Ct serovar D, E and F was propagated in Hela 229 cells (ATCC, Rockville, Md., USA). The cells were cultivated in RPMI 1640 (Gibco BRL, Grand Island, N.Y., USA) media containing 5 fetal calf serum (Gibco BRL; heat inactivated), 1% v/v Hepes, 1% v/v L-glutamine, 1% v/v pyrovate and 10 µg/ml gentamycine. Semiconfluent monolayers of Hela 229 cells in 6 well-plates were infected with 1.5 inclusion forming unit per cell of Ct serovar E or F in 0.3 ml SPG-buffer/well. The plates were centrifuged 1 hour in a Heraeus Multifuge 3S at 750 g and incubated on a plate rocker for 2 h at 35° C. After 2 h 2 ml cultivation media supplemented with 5% glucose and 1 µg/ml cycloheximid were added pr. well and the cells were further incubated for 72 h at 37° C. in an atmosphere of 5% $CO_2$ in humidified air.

Harvesting of Ct

Chlamydiae were harvested 72 h post infection. The cells were dislodged from the wells with a cell scraper and centrifuged 30 minutes at 35.000 g and 4° C. The pellets were resuspended in HBSS, sonicated on ice and centrifuged at 500 g and 4° C. for 15 minutes. The supernatant was collected and saved on ice and the pellet was resuspended to same volume as before and sonication and centrifugation were repeated. The two supernatants were pooled and centrifuged 30 minutes at 30000 g and 4° C. and the pellet resuspended with a needle and syringe in a SPG buffer (3 ml/Plate). After a brief sonication the suspension was gently layered over a 30% Diatrizoate solution (50 g Meglumine diatrizoate, 7.7 g Sodium diatrizoate in 76 ml $H_2O$) and centrifuged at 40,000 g for 30 min. After centrifugation the pellet were resuspended in SPG buffer and stored at -70° C. The IFU of the batches were quantified by titration on McCoy cells and the concentration of the batches was determined by BCA.

Antigen and Fusion Preparation Methods

The genome of *C. trachomatis* serovar D, E, F and G are publicly available (NCBI-GenBank). Genes coding for *C. trachomatis* antigens and fusions where all obtained synthetically for cloning into *E. coli* bacterial protein expression system (DNA2.0). The pET411 vector was used for expression of the recombinant *C. trachomatis* protein in *E. coli* with a Histidine affinity tag. The bacterial host was BL21-STAR™. *E. coli* was grown at 37° C. to reach the logarithmic phase OD600~0.5 and protein expression was induced for 4 hours and cells were harvested by centrifugation (6,000 g for 15 min.). *E. coli* were lysed using Bugbuster (Novagen) containing Benzonase, rLysozyme and Protease inhibitor Cocktail I (Calbiochem). Inclusion bodies were isolated by centrifugation (10,000 g for 10 min.) The pellet was dissolved in 50 mM NaH2PO4, 0.4M NaCl, 8M Urea, 10 mM Imidazole pH 7.5 and loaded onto HisTrap HP column (Amersham Biosciences) and bound proteins were eluted by applying a gradient of 50 to 500 mM imidazole. Depending on the antigen and fusions isoelectric point they were further purified by ion exchange chromatography. Protein concentrations was determined by BCA protein assay (Pierce).

Animals

Female B6C3F1 mice, 8-12 weeks of age, were obtained from Harlan Laboratories. Animals were housed under standard environmental conditions and provided standard food and water ad libitum. The use of mice is guided by the regulations set forward by the Danish Ministry of Justice (Lov om dyreforsøg, jvf lovbekendelser nr. 726 of 9. September 1993), and Animal protection committees. A detailed description of the experiments was submitted to and approved by the regional ethical review board (2012-15-2934-00100) held by the applicant.

Immunization

Mice were immunized 3 times with 14 days between immunizations. The poly peptides were emulsified in CAF01 and administered simultaneously by the subcutaneous (sc) and intranasal (i.n) route. The vaccines given by both routes consisted of 5 ug of peptide (see above) emulsified in 250 ug DDA and 100 ug TDB. As a negative control, DDA/TDB alone, without peptide was injected.

*Chlamydia*-Specific Cellular Responses

Blood lymfocytes or splenocytes were purified. Blood lymphocytes were pooled from 8 mice in each group and spenocytes were cultivated individually (n=4) and cultured in triplicate in round-bottomed microtiter plates (Nunc, Denmark) containing 2×10$^5$ cells/well in a volume of 200 µl RPMI-1640 supplemented with 5×10$^{-5}$M 2-mercaptoethanol, 1 mM glutamine, 1% pyruvate, 1% penicillin-streptomycin, 1% HEPES and 10% fetal calf serum (FCS) (Invitrogen, Denmark). The cells were re-stimulated with individual antigens in 1-10 µg/ml or VD1 and VD4 peptide pools (2 µg/ml of each peptide). Stimulation with Concanavalin A (5 µg/ml) or media as positive control for cell viability and negative control, respectively. After 72 h of incubation at 37° C. in 5% $CO_2$, supernatants were harvested and stored at −20° C. before use. The amounts of secreted IFN-γ were determined by enzyme-linked immunosorbant assay (ELISA).

Serum Antibodies

At different time points post last vaccination the mice were bled and serum isolated by centrifugation. Serum was tested by ELISA for reactivity against the Ct surface (SvD, SvE and SvF), against the SvE VD4 monomer, and against peptides (Table 4&5) spanning the VD4 region of SvD, SvE and SvF. Briefly, plates were coated with antigen (1 to 10 ug/ml) at 4° C. in carbonate buffer overnight, blocked with BSA and washed. The plates were then incubated with pre-diluted samples at 4° C. overnight, washed and incubated with a peroxidase conjugated secondary antibody for 1 hr. Reactions were visualized by incubation with TMB substrate and the reaction stopped with sulphuric acid and read at 450 nm. When ELISA reactivity against a 9mer overlapping peptide panel spanning the VD4 region of SvD (SvE) (Table 6) and SvF (Table 7) was investigated minor changes were done. Briefly, plates were treated with streptavidin and coated with biotinylated peptides, blocked for 2 h at room temperature with skimmed-milk powder and washed. The plates were then incubated with pre-diluted (1:100) serum samples for 2 h at room temperature, washed and incubated with a peroxidase conjugated secondary antibody for 1 hr. Reactions were visualized by incubation with TMB substrate and the reaction stopped with sulphuric acid and read at 450 nm.

Neutralization Assay

HaK cells were grown to confluence in 96-well flat-bottom microtiter plates in RPMI 1640 media supplemented with 5% fetal calf serum (Gibco BRL; heat inactivated), 1% v/v Hepes, 1% v/v L-glutamine, 1% v/v pyrovate and 10 µg/ml gentamycine.

The *Chlamydia* stocks were previously titrated and diluted to 3×10$^6$ IFU/ml for SvE, 2×10$^6$ IFU/ml for SvD and 5×10$^6$ IFU/ml for SvF. Serum (pooled) isolated from vaccinated mice was heat inactivated at 56° C. for % h, diluted 2-4 times and 4-5 fold titrated. 80 µl of the bacteria suspension was mixed with 80 µl of serum (+/−20 µg/ml peptide) and incubated for 30 min. at 37° C. on a slowly rocking platform and 50 µl of the suspension were then inoculated onto the previously prepared HaK cells in duplicates. To do this, the media was removed from the HaK monolayers and 100 µl of the above media supplemented with 0.5% glucose and 10 µg/ml cyclohexamide was added followed by 50 µl of the serum/bacteria suspension. Plates were incubated at 35° C. on a slowly rocking platform, then inoculum was removed and 100 µl of the above media supplemented with 0.5% glucose and 10 µg/ml cycloheximide was added. The plates were then incubated for 24 h at 37° C. in an atmosphere of 5% $CO_2$ in humidified air. After incubation the medium was removed and the monolayers were fixed with 96% ethanol for 10 min. Inclusions were visualized by staining with polyclonal rabbit anti-CT755 serum made in our laboratory, followed by FITC-conjugated swine anti-rabbit immunoglobulin (Dako). Background staining was done with propidium iodide (Invitrogen)

Vaginal Challenge and Vaginal Chlamydial Load

Ten and 3 days before Ct serovar D challenge, the oestrus cycle was synchronized by injection of 2.5 mg Medroxyprogesteronacetat (Depo-Provera; Pfizer). Six weeks after the final vaccination the mice were challenged i. vag. with 4-8×10$^5$ IFU of Ct serovar D in 10 µl SPG buffer. Vaginal swabs were obtained at 3, 7, 10 and 14 days after infection. Swabs were vortexed with glass-beads in 0.6 ml SPG buffer and stored at −80 C until analysis. Infectious load was determined as described in[17]. Briefly, McCoy cell monolayers were infected with a titrated volume of the swab suspension in duplicates. The plates were centrifuged at 750×g for 1 h at RT followed by incubation at 35 C for 2 h. Infection-media was then replaced with fresh media and the cells incubated at 37 C for 30 h. Inclusions were visualised by staining with polyclonal rabbit anti-CT681 serum made in our laboratory, followed by a FITC conjugated swine anti-rabbit Ig (DAKO, Glostrup, Denmark). Background staining was done with propidium iodide (Invitrogen, Taastrup, Denmark). Inclusions were enumerated by fluorescence microscopy observing at least 20 individual fields of vision for each well.

Depletion of $CD4^+$ and $CD8^+$ T-cells

Monoclonal anti-mouse CD4 (clone GK1.5) and anti-mouse CD8 (clone YTS156 and YTS169 a gift from Stephen Cobbold)[78, 79] was purified from hybridoma supernatants made in our lab, using HiTrap protein G HP columns (GE-Healthcare Life Sciences, Denmark). The purified IgG was dialyzed against PBS, filtered through 0.22 um filter and protein concentration was determined by OD 280 nm. Mice were depleted of $CD4^+$ or $CD8^+$ T-cells by 4 injections of 250-300 µg purified anti-CD4 or a mix of anti-CD8 antibodies at day −7, −4, −1 and +2 and +6 relative to the day of infection. The $CD4^+$ and $CD8^+$ T cell depletions were verified by FACS analysis on PBMCs at day 1 post infection using a FITC conjugated anti-CD4 antibody (clone RM4-4) and a PE-conjugated anti-CD8 antibody (clone 53-6) (BD Biosciences, Denmark).

In Vivo Depletion

The *Chlamydia* serovar D stock was previously titrated and diluted to 8×10$^4$ IFU/µl, mixed 1:1 with serum isolated from mice immunized with a heterologous VD4 immuno-repeat SvD-SvE-SvF (CTH89). Ten and 3 days before Ct serovar D challenge, the oestrus cycle was synchronized by injection of 2.5 mg Medroxyprogesteronacetat (Depo-Provera; Pfizer). Mice were challenged i. vag. with 10 µl of the above mix (4×10$^5$ IFU of Ct serovar D). Vaginal swabs were obtained at 3, 7 and 10 days after infection.

Statistical Analysis

Statistical analysis was done using GraphPad Prism 4. Medians of vaginal *Chlamydia* load were analyzed using Kruskall-Wallis followed by Dunn's post test or Mann-Whitney. Example 1: Enhanced Immune Responses after Immunization with Homologous Immuno-repeats of VD4$^{ext}$ compared with a monomeric VD4$^{ext}$ unit.

Introduction

Here we selected polypeptide units containing extended VD4 fragments of serovar E (for sequence see FIG. 2) (SvE VD4$^{ext}$). In order to potentiate the immune response against these domains we designed recombinant polypeptides were the SvEVD4$^{ext}$ unit was presented in a repetitive manner. To investigate if a repetitive form of the construct could enhance the antibody response compared to a monomeric form, we designed recombinant polypeptides where the units were presented either as a single unit or in a repetitive manner. For serovar E (SvE), a monomeric (SvE VD4$^{ext}$)*1 (CTH181), four immuno-repeats (SvE VD4$^{ext}$)*4 (CTH527) and eight immuno-repeats (SvE VD4$^{ext}$)*8 (CTH526) of the extended VD4 unit were constructed. These homologous immuno-repeat constructs were formulated in the adjuvant CAF01 and used to vaccinate mice; each mice was vaccinated with 2×5 μg peptide so the amount of VD4 was the same. Immunogenicity of the constructs was studied by ELISA against SvE VD4$^{ext}$, peptides covering SvE VD4$^{ext}$ and the bacterial surface of chlamydia.

Results

Figure 5:
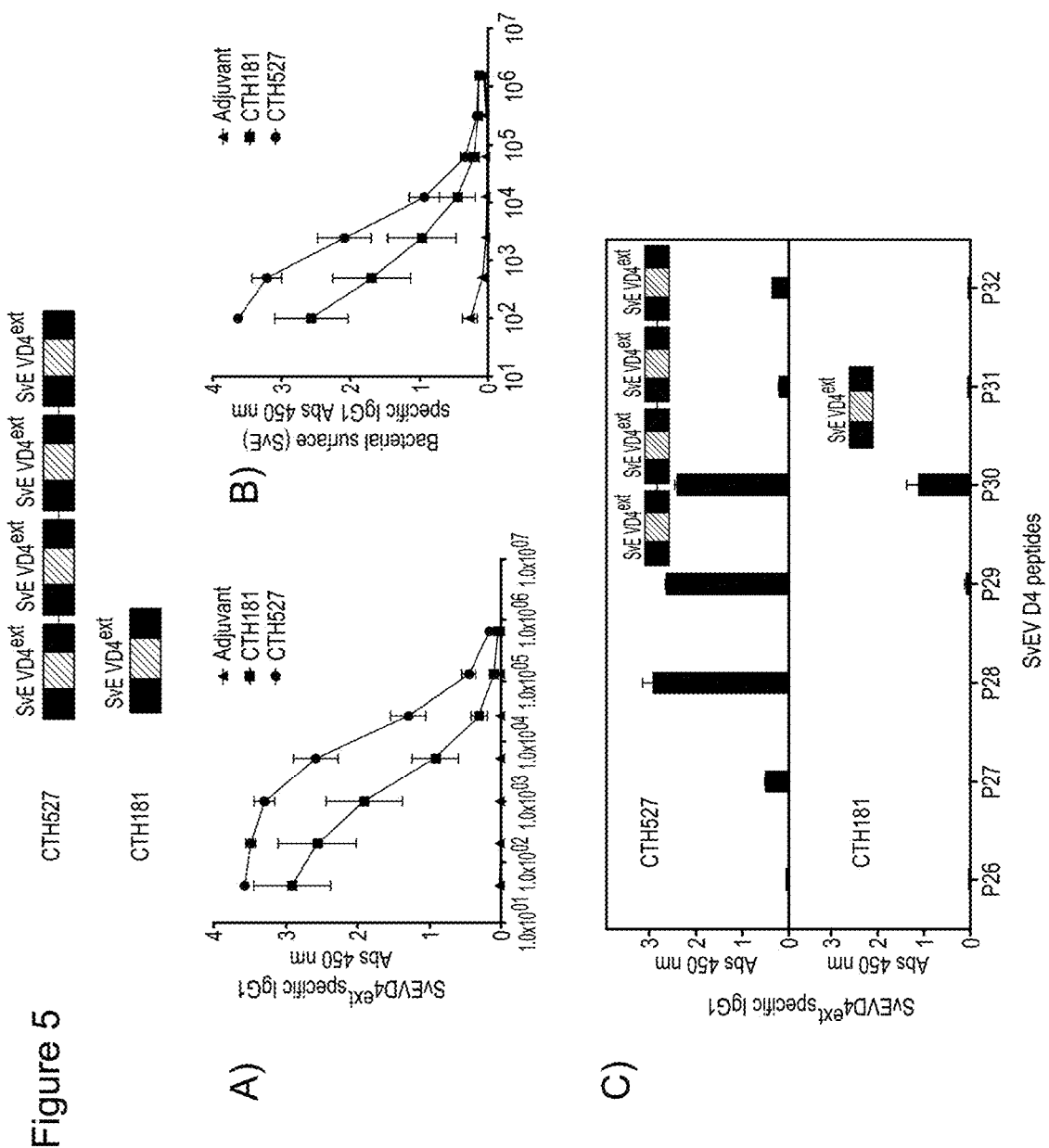
FIGS. 5A-5C. Enhanced and broadened immune responses after immunization with homologous immuno-repeats of VD4$^{ext}$ compared with a monomeric VD4$^{ext}$ unit.

Six mice/group were immunized 2 times with 14 days between immunizations. The vaccines (2×5 μg) were emulsified in CAF01 and administered simultaneously by the sc. and i.n routes. At certain time points post last vaccination blood was collected and antibody levels against the extended VD4 units from SvE and against the bacterial surface of SvE were measured by ELISA. Vaccination with a single VD4$^{ext}$ unit (monomeric VD4$^{ext}$, CTH181) induced lower levels of VD4$^{ext}$ specific antibodies compared to the level induced after immunization with homologous immuno-repeats composed of 4 VD4$^{ext}$ repeats of (SvE VD4$^{ext}$)*4 (FIG. 5A). The higher antibody response seen after immunizing with (SvE VD4$^{ext}$*4 resulted in a stronger recognition of the bacterial surface compared to serum isolated from (VD4$^{ext}$*1 immunized mice (FIG. 5B). The response to 20mer peptides with 10 aa overlap spanning the extended VD4 region (Table 4) was also enhanced resulting in a broader epitope recognition pattern in the (VD4$^{ext}$)*4 homologous immuno-repeat groups compared to the group of mice immunized with a monomeric VD4$^{ext}$ unit when tested in a 1:500 serum dilution (FIG. 5C). In the group immunized with the monomeric construct the response was exclusively targeted to the central region containing the TTLNPTIAG (SEQ ID NO: 76) epitope whereas immunization with the homologous immuno-repeat exposed several B cell epitopes both up- and downstream of that epitope resulting in a diverse epitope recognition pattern of various epitopes. We continued by investigating if immuno-repeats of 8 (SvE VD4$^{ext}$)*8 (CTH526, seq no 30) were more immunogenic than immuno-repeats of 4 (SvE VD4$^{ext}$*4. The two constructs induced similar levels of antibodies against the extended VD4 unit and against the bacterial surface of SvE.

Conclusion

We demonstrated that by immunizing with immuno-repeats of extended VD4 units from Serovar E we can greatly enhance antibody response both measured as the titer (FIGS. 5A&B) and the breadth of the response (FIG. 5C) directed against the extended VD4 unit resulting in a strong reactivity towards the bacterial surface. We did not find enhanced antibody titers and neutralization titers by increasing the number of repeats from 4 to 8.

Example 2: A Construct Composed of Heterologous Immuno-Repeats from SvD, E, F and G (CTH518) Induced a Stronger Response to Multiple Serovars Compared to Homologous Immuno-Repeats from SvF Introduction We investigated if immunization with at heterologous immuno-repeat composed of extended VD4 units from SvD, SvE, SvF and SvG (CTH518), maintained the strong immunogenicity and was able to induce a broader antibody response recognizing the surface of multiple serovars compared to immunization with a homologous immuno-repeat composed of extended VD4 units from SvF (SvF VD4$^{ext}$)*4, (CTH529). These immuno-repeat constructs were formulated in the adjuvant CAF01 and used to vaccinate mice. The immunogenicity of the constructs was studied by ELISA against the bacterial surface of Serovar D, E and F.

Results

Figure 6:
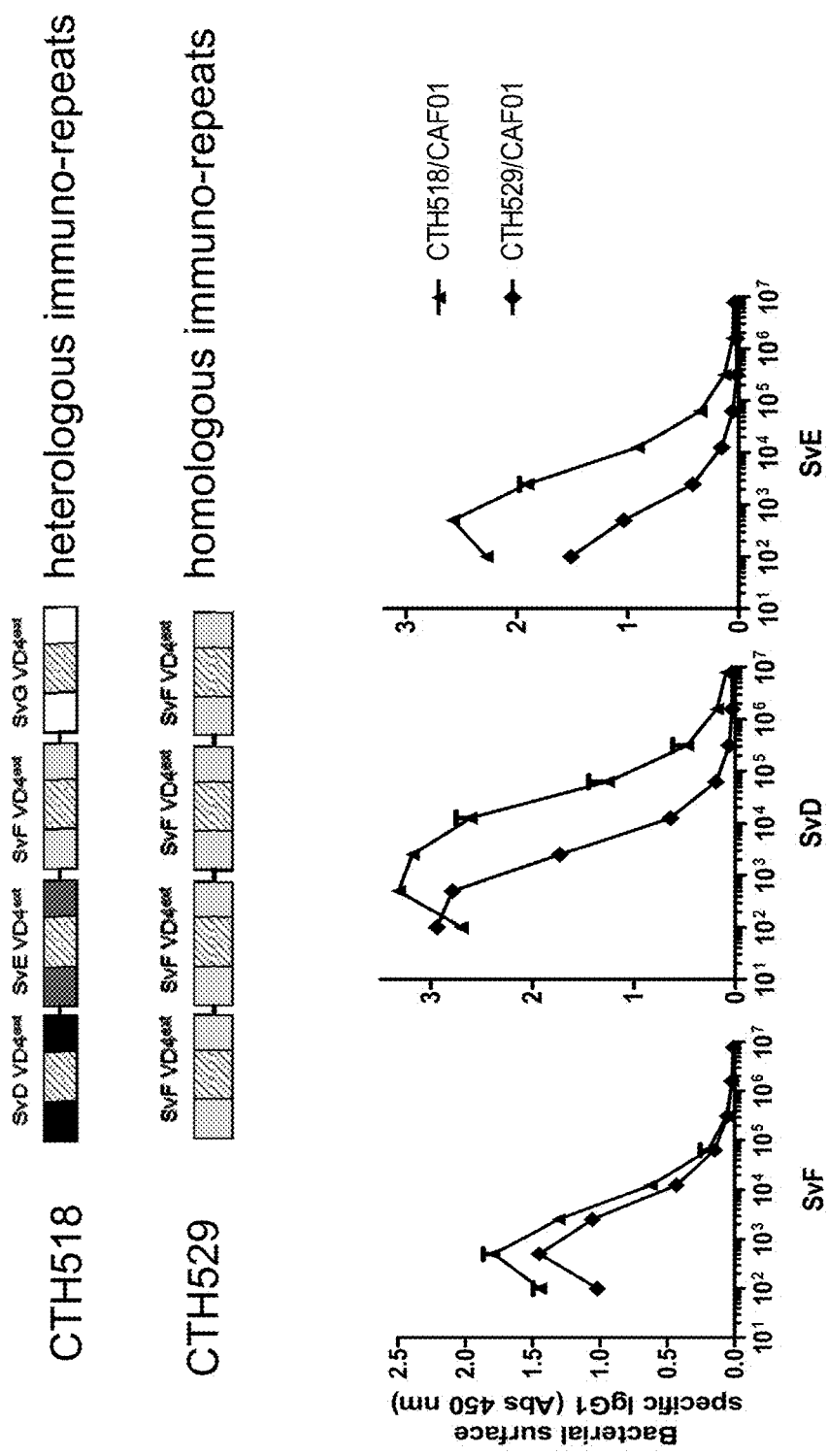
FIG. 6. A construct composed of heterologous immuno-repeats from SvD, E, F and G induced a stronger response to multiple serovars compared to homologous immuno-repeats from SvF.

Heterologous immuno-repeats promoted an antibody response that recognized the surface of the serovar F strain at the same high level as the response seen with a homologous immuno-repeat from SvF. However, by immunization with the heterologous immuno-repeat containing extended VD4 regions from the four serotypes (SvD, SvE, SvF, SvG) we observed a markedly increased titer to the D and E serovariants compared to the homologous immuno-repeat from the serovar F (FIG. 6).

Conclusion

Immunizing with the construct composed of immuno-repeats of heterologous extended VD4's induced a broader response recognizing the surface of multiple serovars (D, E and F) while maintaining the pronounced immunogenicity of the homologous immuno-repeat.

Example 3: The Specificity of the Antibody Responses after Immunization with a Heterologous Immuno-Repeat of the Extended VD4 Units from Serovar D, E, and F (CTH89) Compared to Constructs Composed of a Homologous Immuno-Repeat from (SvE$^{ext}$ VD4)*4, (SvF$^{ext}$ VD4)*4 and a Previously Published A8-VD4 Peptide[65]

Introduction

We investigated the specificity of the immune response after immunization with a heterologous repeat of extended VD4 domains from SvD, SvE, SvF (CTH89) compared to immunization with homologous immuno-repeats composed of extended VD4 repeats from Serovar E (SvE$^{ext}$VD4)*4 (CTH527), SvF (SvF$^{ext}$VD4)*4 repeats (CTH524) and A8-VD4 peptide. These constructs were formulated in the adjuvant CAF01 and used to vaccinate mice. Immunogenicity of the constructs was studied by ELISA against a peptide panel (9 and 20 AA long) spanning the VD4 region of D, E and F (Tables 4-7). Serum (from 6 to 8 mice) was tested and a response above background but below OD=1.0 is indicated by an open box, responses above 1.0 are marked by a filled box. The length of the box indicates the area recognized by antibodies.

Results

All constructs induced high antibody responses to the conserved TTLNPTIAG (SEQ ID NO: 76) part of the VD4$^{ext}$, located in the variable domain (VD). In general antibodies generated by homologous immuno-repeats were superior in recognizing their representative homologous VD4$^{ext}$ region, whereas it was evident that when these constructs were tested against peptides covering a VD4$^{ext}$ from a different serovar their epitope recognition repertoire was limited e.g. the recognition of serovar E VD4 region by serum from animals immunized with the construct (SvF$^{ext}$VD4)*4 (FIG. 7A and FIGS. 7C-A, 7C-B, and 7C-C) (and vice versa) (FIG. 7B and FIGS. 7C-A1, 7C-B1, and 7C-C1). Antibodies generated after immunization with the heterologous immuno-repeats (CTH89), recognized a much broader epitope repertoire than serum from animals immunized with the homologous immuno-repeats and the A8-VD4 (FIGS. 7A-7D-B). This construct was able to cover an epitope repertoire covering both serovar E and F at the level (or better) than achieved by immunizing with homologous immuno-repeats.

To demonstrate whether a 17 AA peptide representing a central VD4 peptide FDTTTLNPTIAGAGDVK (SEQ ID NO: 194) was able to compete with *C. trachomatis* organisms for CTH89 specific antibody binding, a competitive neutralization assay was performed. Different concentrations of CTH89 and A8-VD4 specific serum were mixed with the peptide in a concentration of 20 μg/ml (FIG. 7D-C). The results demonstrates that, in contrast to A8-VD4 specific serum, the peptide could not completely eliminate the neutralizing capacity of the CTH89 specific serum, suggesting that this serum targets a broader repertoire of neutralizing epitopes.

Conclusion

Immunizing with immuno-repeats of heterologous extended VD4's induced a broad response recognizing both conserved and serovar specific parts of the VD4 region, translating into a broader repertoire of neutralizing epitopes.

Example 4: Immunization with Heterologous Immuno-Repeats of Extended VD4's from SvD, SvE and SvF (CTH89) Generates Early T Cell Independent Protection after a SvD Challenge Introduction In order to study the effector mechanism responsible for the early protection seen after vaccination with the VD4 repetitive units, mice vaccinated with CTH89 were T cell depleted before challenge and the capacity to induce early protection was compared in depleted and non-depleted mice.

Results

Figure 8:
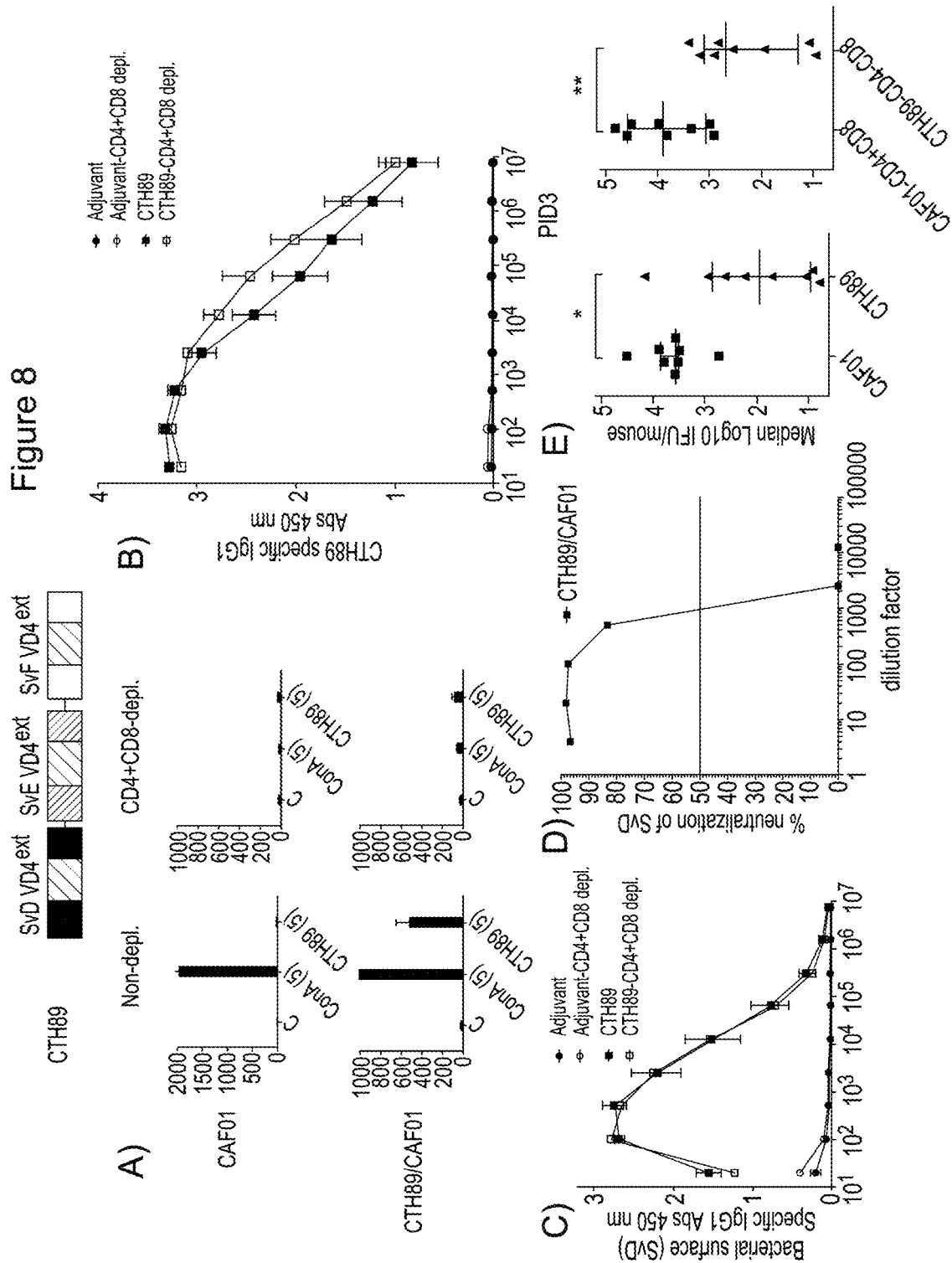
FIGS. 8A-8F. Immunization with heterologous immuno-repeats of extended VD4's from SvD, SvE and SvF (CTH89) generates early T cell independent protection after a SvD challenge.
Figure 8:
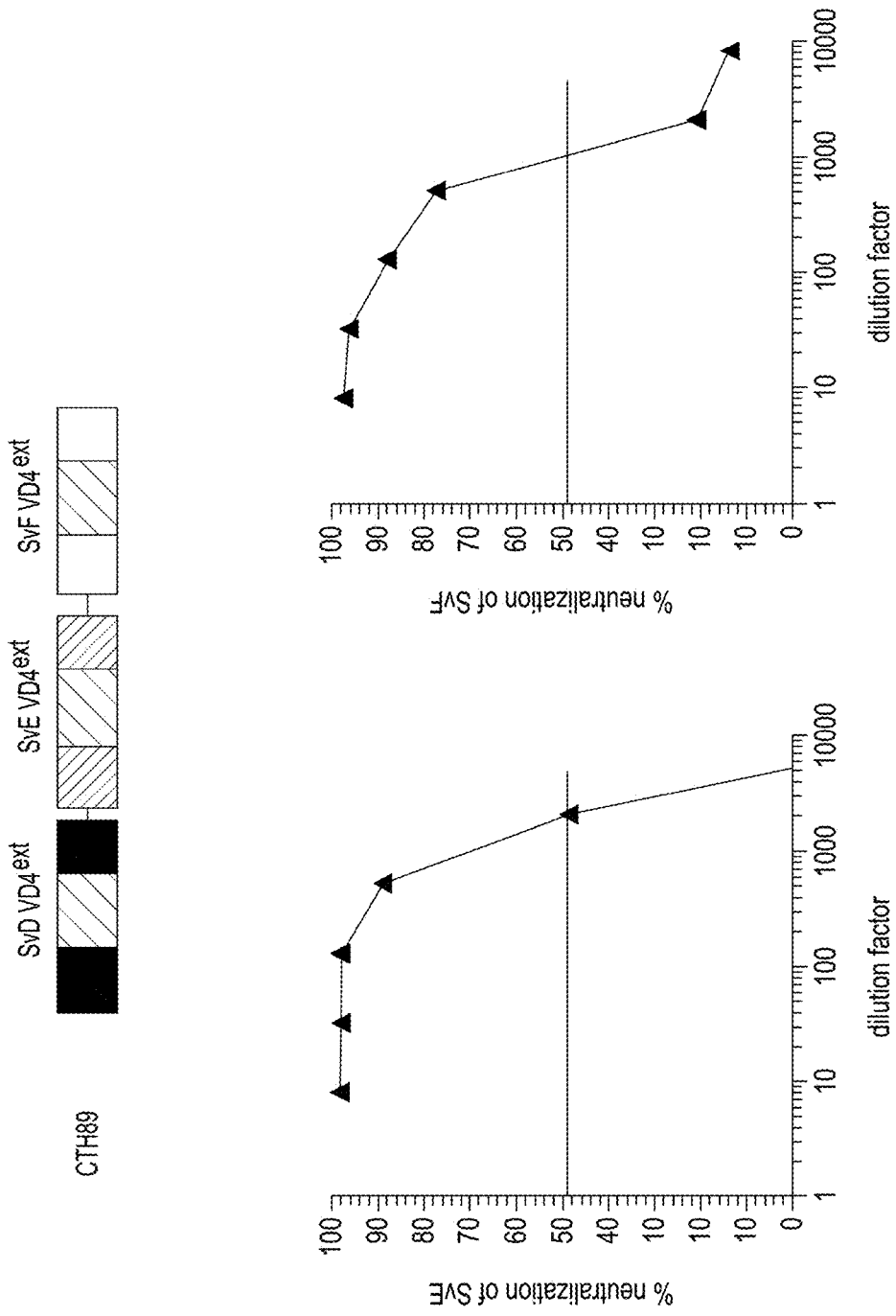

Eight mice/group were immunized 3 times with 14 days between immunizations. The vaccine (2×5 μg) was emulsified in CAF01 and administered simultaneously by the sc. and i.n routes. At certain time points post last vaccination the mice were bleed and antibody responses against *chlamydia*, the neutralization titer, and in vivo protection with and without T cell depletion were measured. Depletion of the T cell subset eliminated the T cell response to CTH89 (FIG. 8A). CTH89 induced a strong antibody response (FIG. 8B) that recognized the surface of serovar D (FIG. 8C) and was able to neutralize the bacteria in vitro with a 50% neutralization titer of around 1:10³ (FIG. 8D). However, we still found significant protection at day 3 post challenge in the T cell depleted mice (FIG. 8E) suggesting an in vivo role for antibodies recognizing the VD4 unit in early protection against *Chlamydia*. Finally we demonstrated that CTH89 serum was also able to neutralize a SvE and SvF infection with very high 50% neutralization titers at the level of that obtained with SvD (FIG. 8F).

CONCLUSIONS

Immuno-repeat generates T cell independent early protection against vaginal challenge with Serovar D suggesting an in vivo role of VD4 specific antibodies.

Example 5: In Vivo Neutralization with CTH89 Specific Serum

Introduction

In order to investigate if the in vitro neutralization could be translated to a protective effect mediated by serum in vivo, we next investigated if SvD bacteria coated with antibodies generated after CTH89 immunization could neutralize/inhibit the infection in vivo compared to serum from naive mice.

Results

Figure 9:
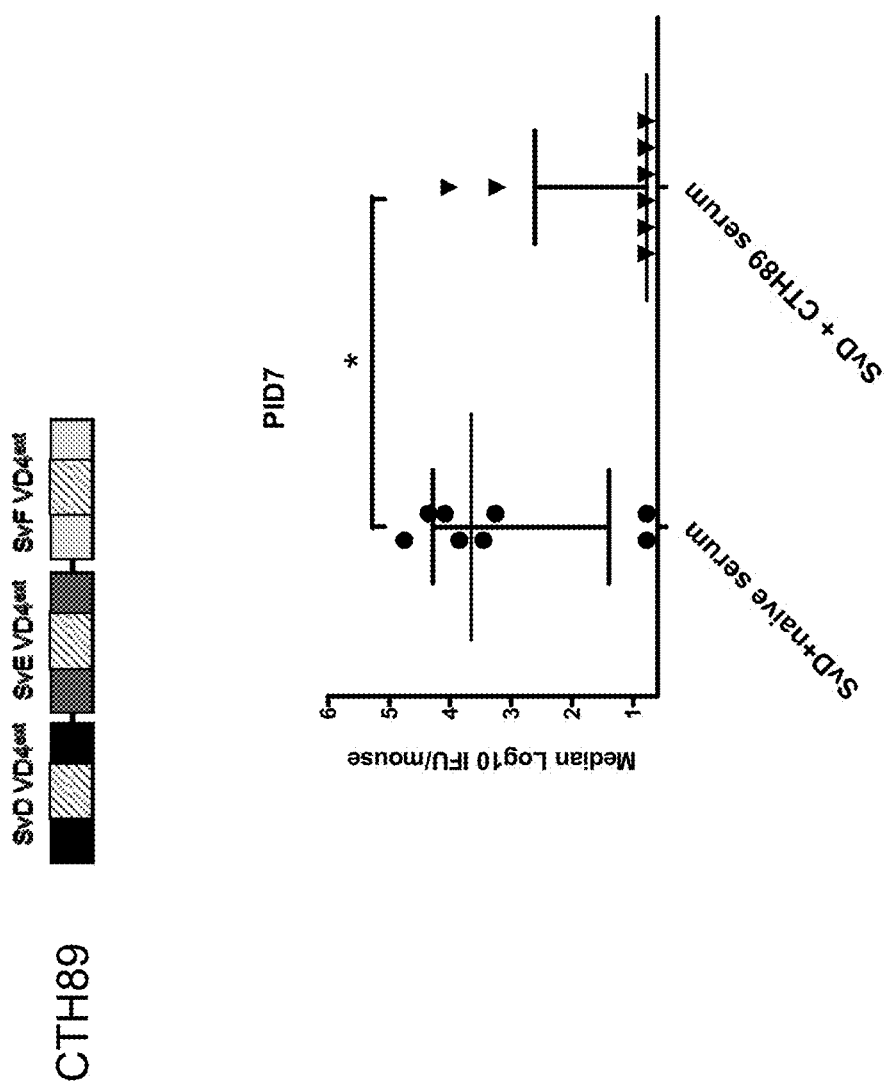
FIG. 9. In vivo neutralization with CTH89 specific serum.

SvD bacteria were mixed with serum isolated from CTH89 immunized mice or serum isolated from naive mice. Depro-provera treated mice were then infected with 4×10⁵ bacteria. Mice infected with SvD coated with CTH89 serum efficiently controlled bacterial replication compared to mice challenged with SvD coated with naive serum. Six out of 8 mice were cleared at day 7 and 10 compared to 2 and 3 respectively, in the control group (FIG. 9).

Conclusion

Figure 10:
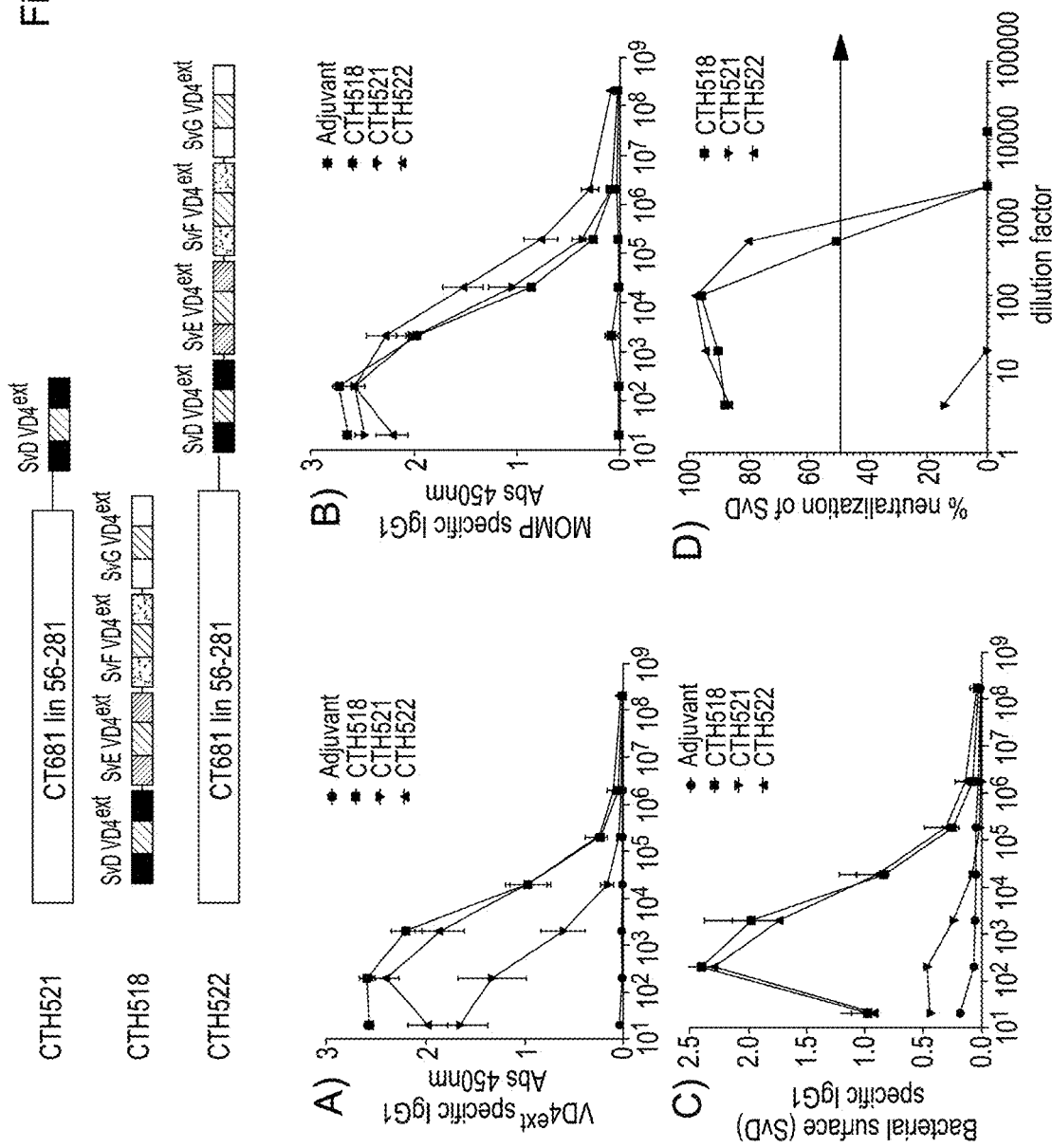
FIGS. 10A-10D. Coupling of heterologous immuno-repeats to recombinant MOMP.

Serum generated after immunization with heterologous VD4 immuno-repeat efficiently block infection of mice with SvD compared to serum isolated from naive mice Example 6. Fusion of Recombinant MOMP with Immuno-Repeats of Heterologous Extended VD4's Introduction MOMP is the target of both humoral and cellular immune-responses but despite the relative success of refolded native MOMP vaccines in generating neutralizing antibodies and protect against infection[54, 56], experimental vaccines based on recombinant MOMP (rMOMP) have failed. We designed a recombinant MOMP ranging from amino acid 56 to 349, including all variable domains (CTH521). We also selected polypeptide units containing extended VD4 fragments (covering the VD4 variable domain of MOMP and the adjacent conserved flanking regions) of serovar D, E, F and G (CT518) Finally a hybrid was constructed where CTH521 was fused to CTH518 (CT522) (FIG. 10).

Results

Eight mice/group were immunized 3 times with 14 days between immunizations. The vaccines were emulsified in CAF01 and administered simultaneously by the sc. (5 μg) and i.n. (5 μg) routes. Post vaccination blood samples were collected and antibodies against the VD4$^{ext}$ unit, recombinant MOMP and against the bacterial surface were measured. Antibodies generated after immunization with CT522 and CT518 recognized the VD4 region (FIG. 10A) and the bacterial surface (FIG. 10C) at a much higher level compared to serum isolated after CT521 immunization. Furthermore antibodies form CTH518 and CTH522 were able to neutralize a SvD infection at the same level and much higher than CTH521 (FIG. 10D).

Conclusion

Fusion of recombinant MOMP with immuno-repeats of heterologous extended VD4's results in a molecule that elicits the same functional antibody response as the immuno-repeat alone.

Example 7: Vaccination with Heterologous Immuno-Repeats of VD1$^{ext}$-VD4$^{ext}$'s Regions from SvD, SvE and SvF (CTH88) Compared to Vaccination with a Single VD1-VD4 Unit from SvD (CTH87)

Introduction

We next investigated if it was possible to fuse another VD region to the extended VD4 region and still maintain the capacity to induce neutralizing antibodies. Therefore constructs were designed were an extended version of the VD1 region was coupled to the extended VD4 region. We produced both a homologous unit composed of an extended unit of VD1 and VD4 from SvD (CTH87) and a heterologous immuno-repeat composed of extended units of VD1 and VD4 from different serovars (D, E and F; CTH88).

Figure 11:
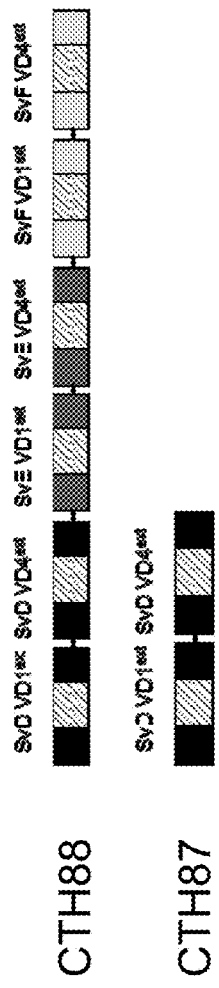
FIGS. 11A-11C. Vaccination with heterologous immuno-repeats of VD1-VD4's regions from SvD, SvE and SvF (CTH88) compared to vaccination with a single VD1-VD4 unit from SvD (CTH87)
Figure 11:
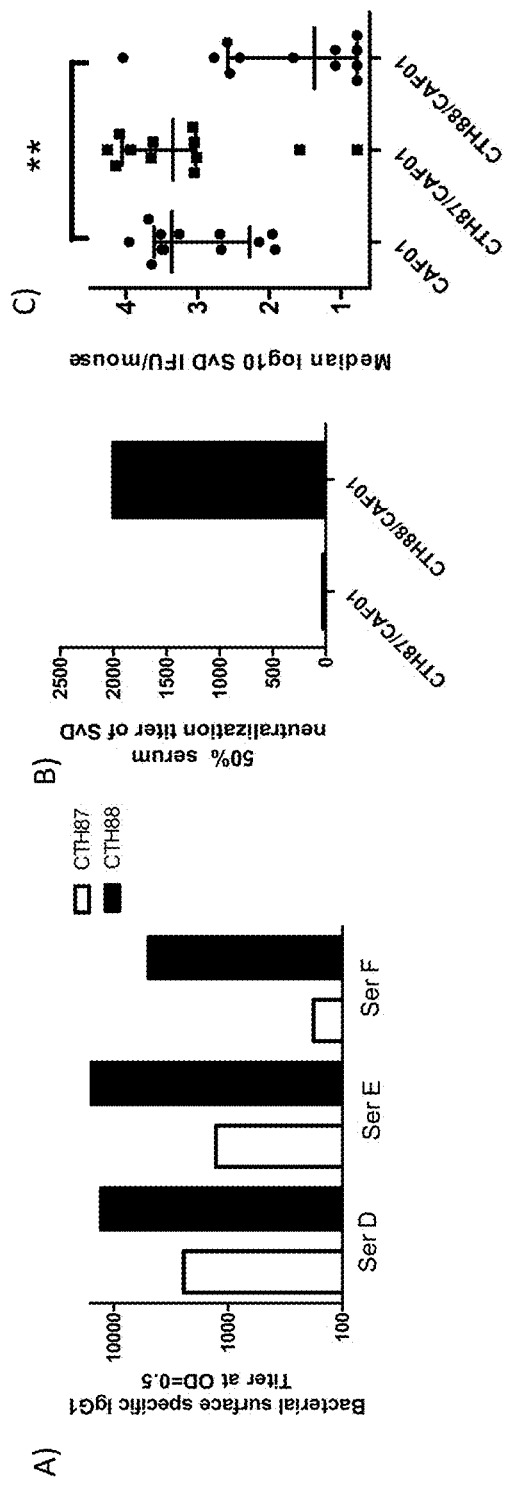

Results 12 mice/group were immunized 3 times with 14 days between immunizations. The vaccines were emulsified in CAF01 and administered simultaneously by the sc. (5 μg) and i.n. (5 μg) routes Antibodies from mice immunized with CTH87 recognized the bacterial surface of both SvD, SvE and SvF (FIG. 11A); with the highest titers observed against the homologous SvD strain and the lowest titers against the most distant SvF. Immunizing with immuno-repeats of heterologous VD1$^{ext}$-VD4$^{ext}$ units resulted in significant higher levels of antibodies against the surface of the bacteria compared to the monomeric construct and broadened the response resulting in titers increasing 6-12 times against SvD and SvE and almost 25 times against SvF (FIG. 11A). The capacity of these antibodies to neutralize infection in an in vitro neutralizing assay was even more improved as serum from animals immunized with the monomeric VD1$^{ext}$-VD4$^{ext}$ construct from serovar D only had minimal neutralizing capacity compared to the heterologous VD1-VD4 immuno-repeat construct with a neutralization titer of 1:2000 (FIG. 11B). Finally did vaccination with the heterologous VD1ext-VD4$^{ext}$ immuno-repeat construct very efficiently protect against a SvD challenge in a vaginal challenge model (FIG. 11C).

Conclusion

We demonstrated that by immunizing with immuno-repeats of heterologous VD1ext-VD4 ext units from serovar D, E and F, we can greatly enhance the antibody response directed against the bacterial surface of all three serovariants. Importantly we also show that by vaccination with a heterologous immuno-repeat, we observe a selective higher increase in Serovar F surface recognition (25 times vs. 6-12 times for serovar D and E), suggesting that the heterologous immuno-repeats not only increase the antibody levels against shared epitopes but also against serovar F specific epitopes. We demonstrated that the antibodies induced with the immuno-repeats of heterologous VD1-VD4 (CTH88) generated in vitro neutralizing titers that resulted in early in vivo protection compared to the single VD1-VD4 unit from SvD (CTH87) (FIG. 11C).

Example 8: Coupling of T Cell Antigens to Immuno-Repeats of VD4

Introduction

As there is a generally recognized need for a CMI component in an efficient protective immune response against *Chlamydia trachomatis*, we next investigated if the heterologous immuno-repeats can be fused to T cell antigens with vaccine potential. Our aim was to provide both an early antibody mediated protection against Ct as well as an efficient CMI mediated clearance of residual organisms. A constructs composed of CT043, and part of CT414 and CT681 was fused to immuno-repeats of heterologous VD1-VD4 (CTH91).

Figure 12:
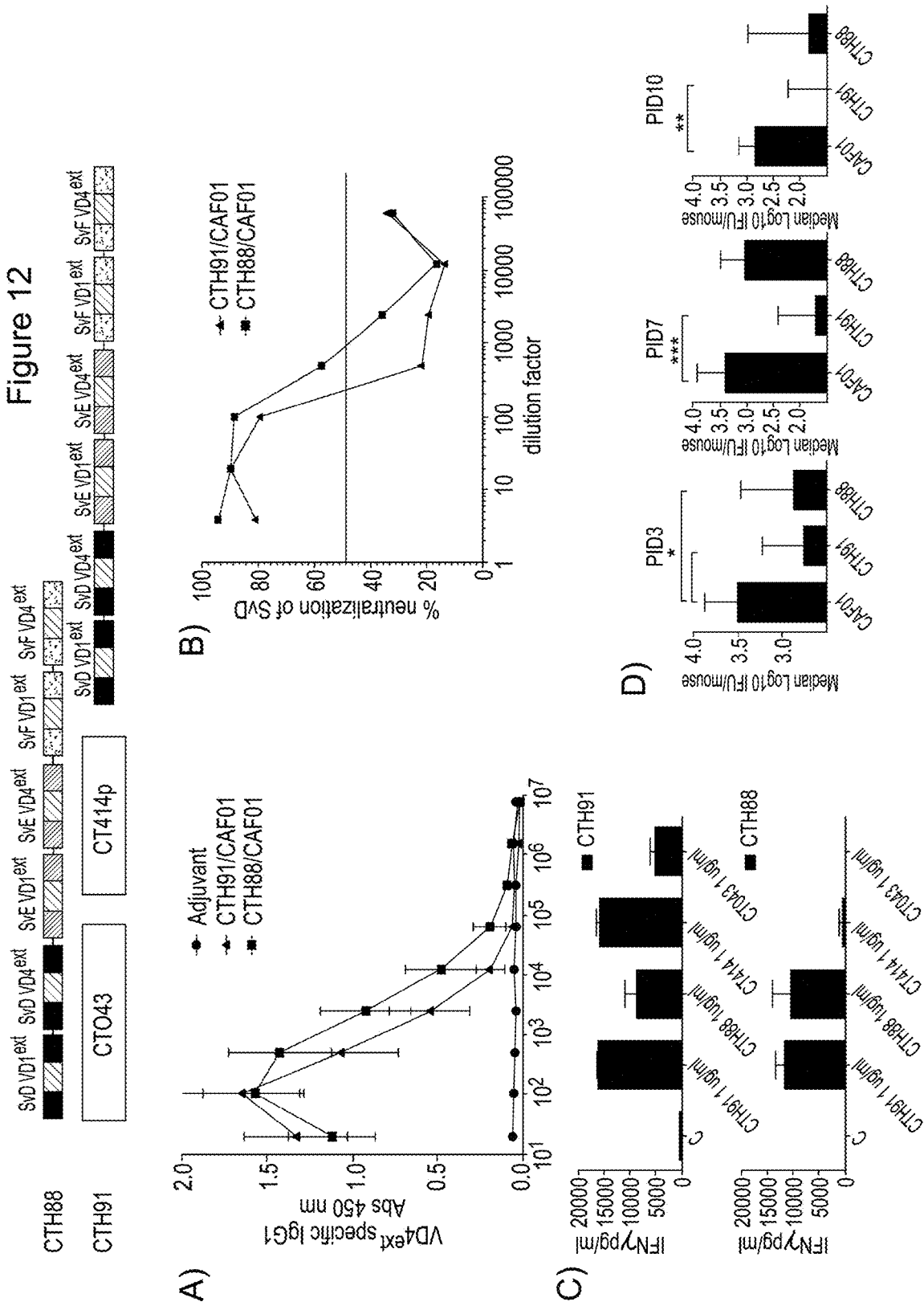
FIGS. 12A-12D. Coupling of T cell antigens to immuno-repeats of VD4

Results 12 mice/group were immunized 3 times with 14 days between immunizations. The vaccines (2×5 μg) were emulsified in CAF01 and administered by the sc. and i.n. routes. At various time points post last vaccination the mice were bleed and antibody responses and neutralization titers were measured. Antibodies generated after immunization with CTH91 and CTH88 recognized the VD4$^{ext}$ region at similar levels (FIG. 12A) and serum isolated from both groups were able to neutralize a SvD infection (FIG. 12B). Compared to CTH88 immunized mice the T cell response to CTH91 was stronger with recognition of both CT414 and CT043 (FIG. 12C). This T and B cell response resulted in significant protection at day 3 post infection for both groups, but at day 7 and 10 post infection the group vaccinated with a fused T and B cell target (CTH91) induced higher levels of protection compared to CTH88 (FIG. 12D).

Conclusion

We were able to fuse T cell antigens with the repetitive VD regions and still maintain the capacity to induce early protection and moreover these constructs induced an efficient CMI mediated clearance of residual organisms leading to high levels of protection at day 7 post infection.

Example 9: Immunization with a Cocktail of a Heterologous VD4 Immuno-Repeat and a T Cell Antigen Fusion Molecule Introduction We next investigated if immuno-repeats can be mixed with T cell antigens with vaccine potential and still provide both an early antibody mediated protection against Ct as well as an efficient CMI mediated clearance of residual organisms. We therefore investigated if we could mix a strong T cell hybrid composed of CT043, part of CT414 and CT681 (CTH93) with CTH89 (FIG. 13A) and still maintain the capacity to neutralize the SvD bacteria in vitro and induce early protection against a vaginal challenge.

Figure 13:
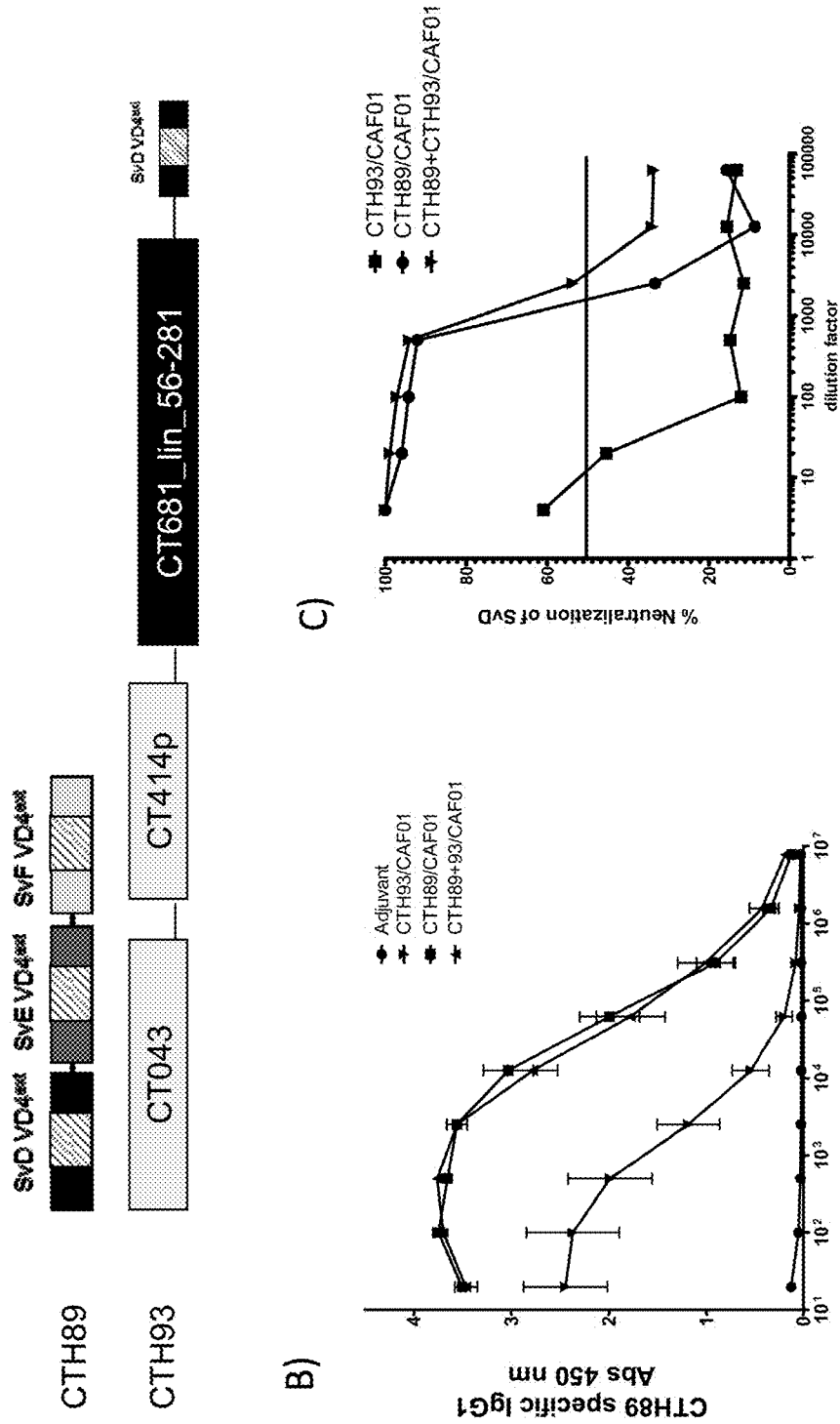
FIGS. 13A-13E. Immunization with a cocktail of a heterologous VD4 immuno-repeat and a T cell antigen fusion molecule FIGS. 14A-14B. Comparison of CAF01 and Alum as adjuvant delivery system.
Figure 13:
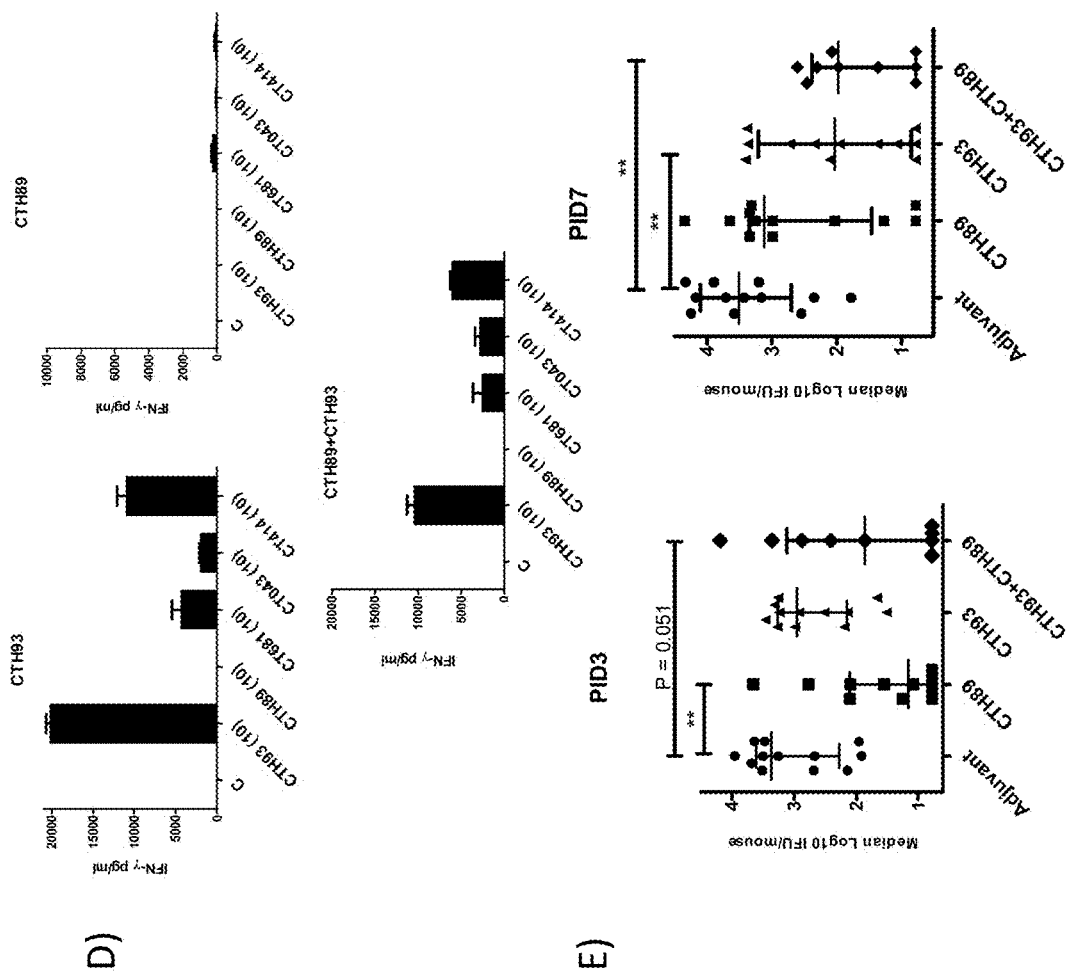

Results 12 mice/group were immunized 3 times with 14 days between immunizations. The vaccine (2×5 μg) were emulsified in CAF01 and administered simultaneously by the subcutaneous (sc) and intranasal (i.n) route (FIG. 13). Antibodies generated after immunization with CTH89 or the mixture of CTH89 and CTH93 strongly recognized the VD4 regions (FIG. 13B) and neutralized the bacteria with similar 50% neutralization titers (FIG. 13C). Much reduced levels of VD4 recognition and neutralization was seen after vaccination with the T cell antigen fusion (CTH93, FIG. 13D) although this molecules also contained MOMP (CT681) and therefore potentially the same neutralizing epitopes. This molecule also gave very low levels of recognition of the TTLNPTIAG (SEQ ID NO: 76) epitope (data not shown). This clearly emphasizes the limitation of full-size recombinant MOMP as a vaccine antigen for the induction of neutralizing antibodies as previously reported. Both the CTH89 and the cocktail of the CTH89 and CTH93 vaccines induced protection at day 3 post infection (FIG. 13E). This was in contrast to CTH93 vaccinated mice which induced no significant protection at day 3 post infection. At day 7 post infection both vaccines including the strong T cell target (CTH93) induced a significant level of protection (FIGS. 13D&E).

Conclusions

We were able to mix the heterologous VD4 repeats with strong T cell antigens without the loss of in vitro neutralization and early in vivo protection against a Serovar D challenge. Moreover, the mix of B and T cell targets induced an efficient CMI mediated clearance of residual organisms leading to high levels of protection at day 7 post infection.

Example 10: Testing the Effect of Different Adjuvant Systems

Introduction

Figure 14:
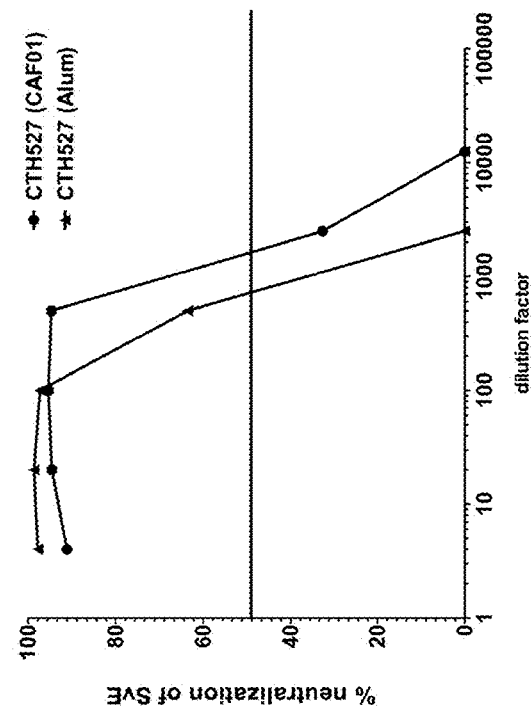
Figure 14:
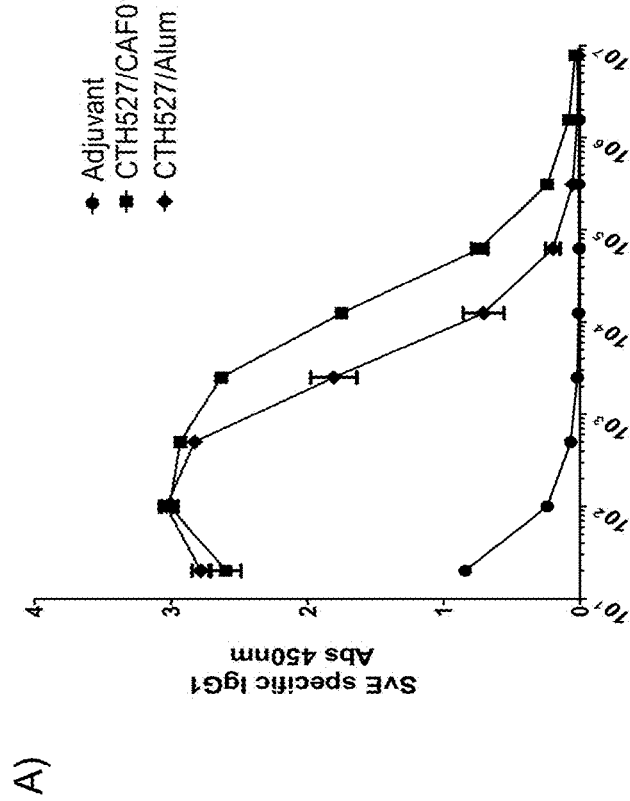

In order to investigate if the high antibody response against heterologous immuno-repeats were only seen when the vaccine were administered in CAF01-we compared the antibody response and the neutralization titer after immunizing with CTH527 (SvE VD4$^{ext}$*4 in CAF01 or Alum.
Results
Both adjuvant systems induced a high antibody response against the surface of SvE when administered together with CTH527(FIG. 14A), and the antibodies from both groups were able to neutralize SvE in vitro (FIG. 14B).

Figure 15:
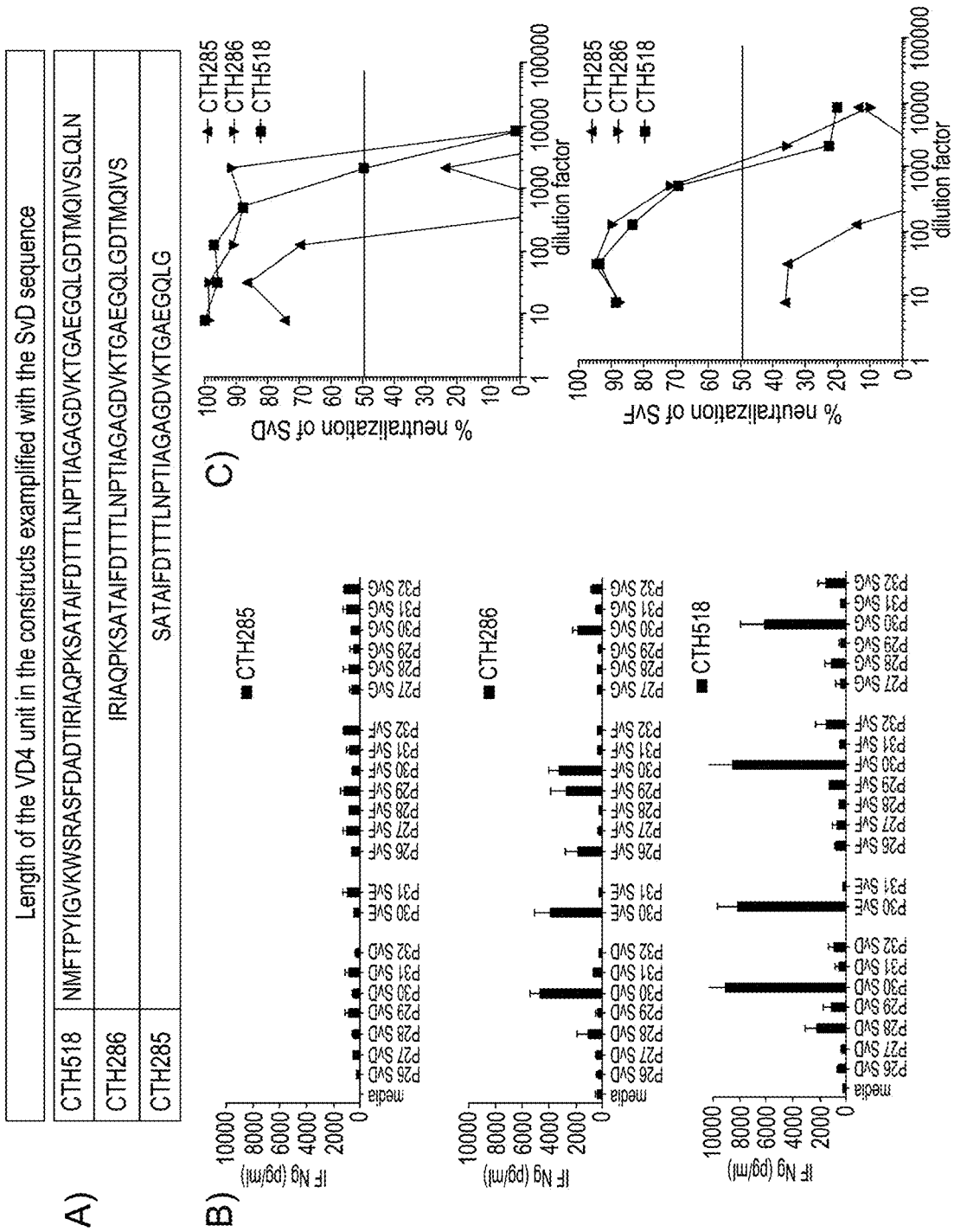
FIGS. 15A-15C. Vaccination with heterologous immuno-repeats composed of reduced length of the VD4$^{ext}$ regions from SvD, SvE, SvF and SvG. The CTH518 sequence shown is amino acids 1 through 68 of SEQ ID NO 53. The CTH286 sequence shown is amino acids 21 through 64 of SEQ ID NO 53. The CTH285 sequence shown is amino acids 28 through 57 of SEQ ID NO: 53.

Example 11: Vaccination with Heterologous Immuno-Repeats Composed of Reduced Length of the VD4$^{ext}$ Regions from SvD, SvE, SvF and SvG Introduction We next compared heterologous immuno-repeat constructs composed of reduced length of the VD4 region (CTH285 (SEQ ID NO: 69) and CTH286 (SEQ ID NO: 70)) compared to the CTH518 construct (CTH518 (SEQ ID NO: 53)) (FIG. 15A).
Results
4 mice/group were immunized 3 times with 14 days between immunizations. The vaccines were emulsified in CAF01 and administered simultaneously by the subcutaneous (sc, 5 µg) and intranasal (i.n, 5 µg) routes. Splenocytes from 4 mice/group were isolated and the T cell responses to overlapping peptides representing the VD4$^{ext}$ region (FIG. 15B) and the capacity of the serum to neutralize a serovar D and F infection (FIG. 15C) were investigated. Much reduced levels of VD4 T cell recognition, and neutralization was seen after vaccination with CTH285 where the VD4$^{ext}$ regions from the different serovars were reduced with 38 aa. CTH286 on the other hand (each VD4$^{ext}$ region reduced with 24 aa) induced similar levels of T cell responses and had the same capacity to neutralize a serovar D infection as CTH518.

Conclusion

We demonstrated that by reducing the length of the VD4$^{ext}$ regions with 38 aa we reduced both the T cell responses and the capacity to neutralize a serovar D and F infection.

Figure 16:
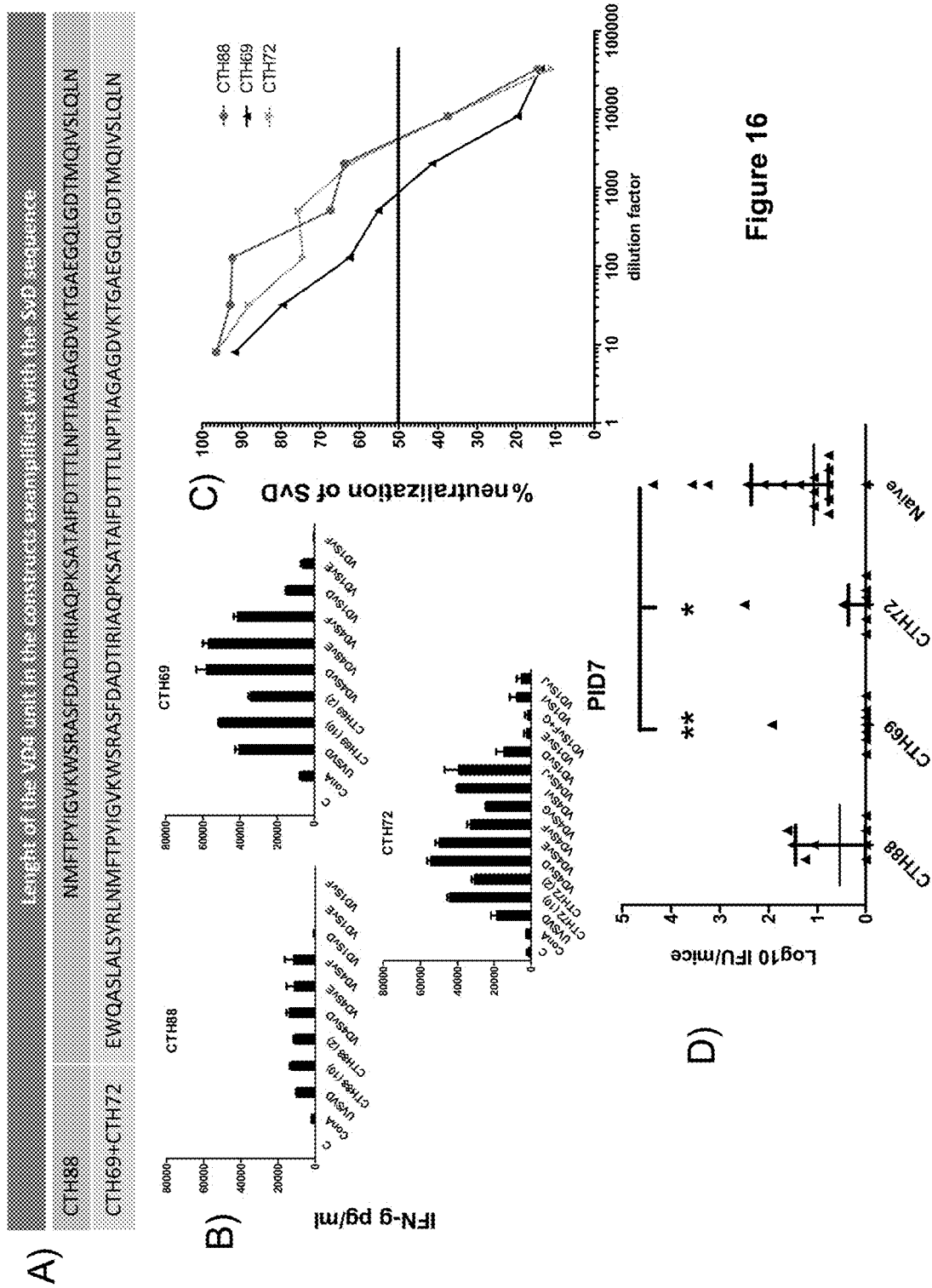
FIGS. 16A-16D. Vaccination with heterologous immuno-repeats composed of extended VD4$^{ext}$ regions from SvD, SvE, SvF, SvG, SvIa and SvJ. The CTH88 sequence shown is amino acids 60 through 127 of SEQ ID NO: 46. The CTH69+CTH72 sequence shown is SEQ ID NO: 255.

Example 12: Vaccination with Heterologous Immuno-Repeats Composed of Extended VD4$^{ext}$ Regions from SvD, SvE, SvF, SvG, SvIa and SvJ Introduction We next investigated if we by extending the length of the VD4$^{ext}$ region could enhance the T cell response to the immuno-repeat constructs. We designed two constructs CTH69 (SEQ ID NO: 47) and CTH72 (SEQ ID NO: 48) (FIG. 16A). CTH69 was similar to CTH88 but the VD4$^{ext}$ regions from SvD, SvE and SvF was extended by 12 aa N-terminally (FIG. 16B). CTH72 also contained VD1 and VD4$^{ext}$ regions from SvG, SvIa and SvJ.
Results Mice were immunized 3 times with 14 days between immunizations. The vaccines were emulsified in CAF01 and administered simultaneously by the subcutaneous (sc, 5 µg) and intranasal (i.n, 5 µg) routes. T cell responses to the antigen used for immunization and to peptide pools representing the VD1 and VD4 regions from the different serovars were investigated (FIGS. 16A-D). Extending the VD4$^{ext}$ regions induced a significant higher T cell response (>40.000 µg/ml) compared to the T cell response obtained with CTH88 (<20.000 µg/ml) (FIG. 16B). Importantly, both of the extended constructs were still able to neutralize a serovar D infection in vitro (FIG. 16C). Comparing the protective efficacy of the vaccines, CTH69 and CTH72 induced a significant level of protection at day 7 post infection which could possibly be explained by the stronger T cell response induced by these vaccines compared to CTH88 (FIG. 16D).

Conclusion

Extending the VD4$^{ext}$ region enhanced the T cell response compared to CTH88 which led to enhanced protection at day 7 post infection.

REFERENCES

1. WHO. Global Prevalence and Incidence of selected Curable Sexually Transmitted Infections: Overview and Estimates. World Health Organization, Geneva, Switzerland; 2001.
2. Paavonen J, Eggert-Kruse W. *Chlamydia trachomatis*: impact on human reproduction. *Hum Reprod Update* 1999, 5(5): 433-447.
3. Plummer F A, Simonsen J N, Cameron D W, Ndinya-Achola J O, Kreiss J K, Gakinya M N, et al. Cofactors in male-female sexual transmission of human immunodeficiency virus type 1. *J Infect Dis* 1991, 163(2): 233-239.
4. Anttila T, Saikku P, Koskela P, Bloigu A, Dillner J, Ikaheimo I, et al. Serotypes of *Chlamydia trachomatis* and risk for development of cervical squamous cell carcinoma. *Jama* 2001, 285(1): 47-51.
5. Golden M R, Schillinger J A, Markowitz L, St Louis M E. Duration of untreated genital infections with *Chlamydia trachomatis*: a review of the literature. *Sex Transm Dis* 2000, 27(6): 329-337.
6. Batteiger B E, Xu F, Johnson R E, Rekart M L. Protective immunity to *Chlamydia trachomatis* genital infection: evidence from human studies. *J Infect Dis,* 201 Suppl 2: S178-189.
7. Brunham R C, Rey-Ladino J. Immunology of *Chlamydia* infection: implications for a *Chlamydia trachomatis* vaccine. *Nat Rev Immunol* 2005, 5(2): 149-161.

8. Su H, Caldwell H D. CD4+ T cells play a significant role in adoptive immunity to *Chlamydia trachomatis* infection of the mouse genital tract. *Infect Immun* 1995, 63(9): 3302-3308.

9. Morrison S G, Su H, Caldwell H D, Morrison R P. Immunity to murine *Chlamydia trachomatis* genital tract reinfection involves B cells and CD4(+) T cells but not CD8(+) T cells. *Infect Immun* 2000, 68(12): 6979-6987.

10. Morrison R P, Caldwell H D. Immunity to murine chlamydial genital infection. *Infect Immun* 2002, 70(6): 2741-2751.

11. Rasmussen S J. *Chlamydia* immunology. *Curr Opin Infect Dis* 1998, 11(1): 37-41.

12. Rank R. In: *Chlamydia* Intracellular Biology, Pathogenesis and Immunity Washington D.C. ASM Press 1999: Pp. 239-296.

13. Morrison S G, Morrison R P. Resolution of secondary *Chlamydia trachomatis* genital tract infection in immune mice with depletion of both CD4+ and CD8+ T cells. *Infect Immun* 2001, 69(4): 2643-2649.

14. Moore T, Ekworomadu C O, Eko F O, MacMillan L, Ramey K, Ananaba G A, et al. Fc receptor-mediated antibody regulation of T cell immunity against intracellular pathogens. *J Infect Dis* 2003, 188(4): 617-624.

15. Pal S, Rangel J, Peterson E M, de la Maza L M. Immunogenic and protective ability of the two developmental forms of Chlamydiae in a mouse model of infertility. *Vaccine* 1999, 18(7-8): 752-761.

16. Darville T, Hiltke T J. Pathogenesis of genital tract disease due to *Chlamydia trachomatis*. *J Infect Dis* 2010, 201 Suppl 2: 5114-125.

17. Hansen J, Jensen K T, Follmann F, Agger E M, Theisen M, Andersen P. Liposome Delivery of *Chlamydia muridarum* Major Outer Membrane Protein Primes a Th1 Response That Protects against Genital Chlamydial Infection in a Mouse Model. *J Infect Dis* 2008, 198(5): 758-767.

18. Olsen A W, Theisen M, Christensen D, Follmann F, Andersen P. Protection against *Chlamydia* promoted by a subunit vaccine (CTH1) compared with a primary intranasal infection in a mouse genital challenge model. *PLoS One,* 5(5): e10768.

19. Li W, Murthy A K, Guentzel M N, Chambers J P, Forsthuber T G, Seshu J, et al. Immunization with a combination of integral chlamydial antigens and a defined secreted protein induces robust immunity against genital chlamydial challenge. *Infect Immun* 2010, 78(9): 3942-3949.

20. Olsen A W, Follmann F, Højrup P, Leah R, Sand C, Andersen P, et al. Identification of human T-cell targets recognized during the *Chlamydia trachomatis* genital infection. *J Infect Dis* 2007, 196: 1546-1552.

21. Olsen A W, Follmann F, Jensen K, Hojmp P, Leah R, Sorensen H, et al. Identification of CT521 as a frequent target of Th1 cells in patients with urogenital *Chlamydia trachomatis* infection. *J Infect Dis* 2006, 194(9): 1258-1266.

22. Follmann F, Olsen A W, Jensen K T, Hansen P R, Andersen P, Theisen M. Antigenic profiling of a *Chlamydia trachomatis* gene-expression library. *J Infect Dis* 2008, 197 897-905.

23. Sharma J, Zhong Y, Dong F, Piper J M, Wang G, Zhong G. Profiling of human antibody responses to *Chlamydia trachomatis* urogenital tract infection using microplates arrayed with 156 chlamydial fusion proteins. *Infect Immun* 2006, 74(3): 1490-1499.

24. Coler R N, Bhatia A, Maisonneuve J F, Probst P, Barth B, Ovendale P, et al. Identification and characterization of novel recombinant vaccine antigens for immunization against genital *Chlamydia trachomatis*. *FEMS Immunol Med Microbiol* 2009, 55(2): 258-270.

25. Karunakaran K P, Rey-Ladino J, Stoynov N, Berg K, Shen C, Jiang X, et al. Immunoproteomic discovery of novel T cell antigens from the obligate intracellular pathogen *Chlamydia*. *J Immunol* 2008, 180(4): 2459-2465.

26. Yu H, Jiang X, Shen C, Karunakaran K P, Brunham R C. Novel *Chlamydia muridarum* T cell antigens induce protective immunity against lung and genital tract infection in murine models. *J Immunol* 2009, 182(3): 1602-1608.

27. Molina D M, Pal S, Kayala M A, Teng A, Kim P J, Baldi P, et al. Identification of immunodominant antigens of *Chlamydia trachomatis* using proteome microarrays. *Vaccine* 2010, 28(17): 3014-3024.

28. Stephens R S, Kalman S, Lammel C, Fan J, Marathe R, Aravind L, et al. Genome sequence of an obligate intracellular pathogen of humans. *Chlamydia trachomatis. Science* 1998, 282(5389): 754-759.

29. Sette A, Rappuoli R. Reverse vaccinology: developing vaccines in the era of genomics. *Immunity* 2010, 33(4): 530-541.

30. Igietseme J U, Eko F O, Black C M. *Chlamydia* vaccines: recent developments and the role of adjuvants in future formulations. *Expert Rev Vaccines* 2011, 10(11): 1585-1596.

31. Rockey D D, Wang J, Lei L, Zhong G *Chlamydia* vaccine candidates and tools for chlamydial antigen discovery. *Expert Rev Vaccines* 2009, 8(10): 1365-1377.

32. Farris C M, Morrison R P. Vaccination against *Chlamydia* genital infection utilizing the murine *C. muridarum* model. *Infect Immun* 2011, 79(3): 986-996.

33. Kubo A, Stephens R S. Characterization and functional analysis of PorB, a *Chlamydia* porin and neutralizing target. *MolMicrobiol* 2000, 38(4): 772-780.

34. Kawa D E, Schachter J, Stephens R S. Immune response to the *Chlamydia trachomatis* outer membrane protein PorB. *Vaccine* 2004, 22(31-32): 4282-4286.

35. Crane D D, Carlson J H, Fischer E R, Bavoil P, Hsia R C, Tan C, et al. *Chlamydia trachomatis* polymorphic membrane protein D is a species-common pan-neutralizing antigen. *Proc Natl Acad Sci USA* 2006, 103(6): 1894-1899.

36. Baehr W, Zhang Y X, Joseph T, Su H, Nano F E, Everett K D, et al. Mapping antigenic domains expressed by *Chlamydia trachomatis* major outer membrane protein genes. *ProcNatlAcadSciUSA* 1988, 85(11): 4000-4004.

37. Bavoil P, Ohlin A, Schachter J. Role of disulfide bonding in outer membrane structure and permeability in *Chlamydia trachomatis*. *Infect Immun* 1984, 44(2): 479-485.

38. Hatch T P, Allan I, Pearce J H. Structural and polypeptide differences between envelopes of infective and reproductive life cycle forms of *Chlamydia* spp. *J Bactenol* 1984, 157(1): 13-20.

39. Stephens R S, Sanchez-Pescador R, Wagar E A, Inouye C, Urdea M S. Diversity of *Chlamydia trachomatis* major outer membrane protein genes. *J Bactenol* 1987, 169(9): 3879-3885.

40. Caldwell H D, Perry L J. Neutralization of *Chlamydia trachomatis* infectivity with antibodies to the major outer membrane protein. *Infect Immun* 1982, 38(2): 745-754.

41. Peeling R, Maclean I W, Brunham R C. In vitro neutralization of *Chlamydia trachomatis* with monoclonal antibody to an epitope on the major outer membrane protein. *Infect Immun* 1984, 46(2): 484-488.

42. Zhang Y X, Stewart S, Joseph T, Taylor H R, Caldwell H D. Protective monoclonal antibodies recognize epitopes located on the major outer membrane protein of *Chlamydia trachomatis*. *J Immunol* 1987, 138(2): 575-581.

43. Zhang Y X, Stewart S J, Caldwell H D. Protective monoclonal antibodies to *Chlamydia trachomatis* serovar- and serogroup-specific major outer membrane protein determinants. *Infect Immun* 1989, 57(2): 636-638.

44. Cotter T W, Meng Q, Shen Z L, Zhang Y X, Su H, Caldwell H D. Protective efficacy of major outer membrane protein-specific immunoglobulin A (IgA) and IgG monoclonal antibodies in a murine model of *Chlamydia trachomatis* genital tract infection. *InfectImmun* 1995, 63(12): 4704-4714.

45. Bandea C I, Debattista J, Joseph K, Igietseme J, Timms P, Black C M *Chlamydia trachomatis* serovars among strains isolated from members of rural indigenous communities and urban populations in Australia. *J Clin Microbiol* 2008, 46(1): 355-356.

46. Hsu M C, Tsai P Y, Chen K T, Li L H, Chiang C C, Tsai J J, et al. Genotyping of *Chlamydia trachomatis* from clinical specimens in Taiwan. *J Med Microbiol* 2006, 55(Pt 3): 301-308.

47. Jonsdottir K, Kristjansson M, Hjaltalin Olafsson J, Steingrimsson O. The molecular epidemiology of genital *Chlamydia trachomatis* in the greater Reykjavik area, Iceland. *Sex Transm Dis* 2003, 30(3): 249-256.

48. Lysen M, Osterlund A, Rubin C J, Persson T, Persson I, Hermann B. Characterization of ompA genotypes by sequence analysis of DNA from all detected cases of *Chlamydia trachomatis* infections during 1 year of contact tracing in a Swedish County. *J Clin Microbiol* 2004, 42(4): 1641-1647.

49. Millman K, Black C M, Johnson R E, Stamm W E, Jones R B, Hook E W, et al. Population-based genetic and evolutionary analysis of *Chlamydia trachomatis* urogenital strain variation in the United States. *J Bacteriol* 2004, 186(8): 2457-2465.

50. Millman K, Black C M, Stamm W E, Jones R B, Hook E W, 3rd, Martin D H, et al. Population-based genetic epidemiologic analysis of *Chlamydia trachomatis* serotypes and lack of association between ompA polymorphisms and clinical phenotypes. *Microbes Infect* 2006, 8(3): 604-611.

51. Su H, Parnell M, Caldwell H D. Protective efficacy of a parenterally administered MOMP-derived synthetic oligopeptide vaccine in a murine model of *Chlamydia trachomatis* genital tract infection: serum neutralizing IgG antibodies do not protect against chlamydial genital tract infection. *Vaccine* 1995, 13(11): 1023-1032.

52. Pal S, Barnhart K M, Wei Q, Abai A M, Peterson E M, de la Maza L M. Vaccination of mice with DNA plasmids coding for the *Chlamydia trachomatis* major outer membrane protein elicits an immune response but fails to protect against a genital challenge. *Vaccine* 1999, 17(5): 459-465.

53. Zhang D J, Yang X, Shen C, Brunham R C. Characterization of immune responses following intramuscular DNA immunization with the MOMP gene of *Chlamydia trachomatis* mouse pneumonitis strain. *Immunology* 1999, 96(2): 314-321.

54. Pal S, Theodor I, Peterson E M, de la Maza L M Immunization with the *Chlamydia trachomatis* mouse pneumonitis major outer membrane protein can elicit a protective immune response against a genital challenge. *Infect Immun* 2001, 69(10): 6240-6247.

55. Shaw J, Grund V, Durling L, Crane D, Caldwell H D. Dendritic cells pulsed with a recombinant chlamydial major outer membrane protein antigen elicit a CD4(+) type 2 rather than type 1 immune response that is not protective. *Infect Immun* 2002, 70(3): 1097-1105.

56. Kari L, Whitmire W M, Crane D D, Reveneau N, Carlson J H, Goheen M M, et al. *Chlamydia trachomatis* native major outer membrane protein induces partial protection in nonhuman primates: implication for a trachoma transmission-blocking vaccine. *J Immunol* 2009, 182(12): 8063-8070.

57. Carmichael J R, Pal S, Tifrea D, de la Maza L M. Induction of protection against vaginal shedding and infertility by a recombinant *Chlamydia* vaccine. *Vaccine* 2011, 29(32): 5276-5283.

58. Yen T Y, Pal S, de la Maza L M. Characterization of the disulfide bonds and free cysteine residues of the *Chlamydia trachomatis* mouse pneumonitis major outer membrane protein. *Biochemistry* 2005, 44(16): 6250-6256.

59. Stephens R S, Wagar E A, Schoolnik G K. High-resolution mapping of serovar-specific and common antigenic determinants of the major outer membrane protein of *Chlamydia trachomatis*. *J Exp Med* 1988, 167(3): 817-831.

60. Murdin A D, Su H, Klein M H, Caldwell H D. Poliovirus hybrids expressing neutralization epitopes from variable domains I and IV of the major outer membrane protein of *Chlamydia trachomatis* elicit broadly cross-reactive *C. trachomatis*-neutralizing antibodies. *Infect Immun* 1995, 63(3): 1116-1121.

61. Murdin A D, Su H, Maiming D S, Klein M H, Parnell M J, Caldwell H D. A poliovirus hybrid expressing a neutralization epitope from the major outer membrane protein of *Chlamydia trachomatis* is highly immunogenic. *Infect Immun* 1993, 61(10): 4406-4414.

62. Villeneuve A, Brossay L, Paradis G, Hebert J. Determination of neutralizing epitopes in variable domains I and IV of the major outer-membrane protein from *Chlamydia trachomatis* serovar K. *Microbiology* 1994, 140 (Pt 9): 2481-2487.

63. Villeneuve A, Brossay L, Paradis G, Hebert J. Characterization of the humoral response induced by a synthetic peptide of the major outer membrane protein of *Chlamydia trachomatis* serovar B. *Infect Immun* 1994, 62(8): 3547-3549.

64. Motin V L, de la Maza L M, Peterson E M Immunization with a peptide corresponding to chlamydial heat shock protein 60 increases the humoral immune response in C3H mice to a peptide representing variable domain 4 of the major outer membrane protein of *Chlamydia trachomatis*. *Clin Diagn Lab Immunol* 1999, 6(3): 356-363.

65. Su H, Caldwell H D. Immunogenicity of a synthetic oligopeptide corresponding to antigenically common T-helper and B-cell neutralizing epitopes of the major outer membrane protein of *Chlamydia trachomatis*. *Vaccine* 1993, 11(11): 1159-1166.

66. Toye B, Zhong G M, Peeling R, Brunham R C. Immunologic characterization of a cloned fragment containing the species-specific epitope from the major outer membrane protein of *Chlamydia trachomatis*. *Infect Immun* 1990, 58(12): 3909-3913.

67. Mygind P, Christiansen G, Persson K, Birkelund S. Detection of *Chlamydia trachomatis*-specific antibodies in human sera by recombinant major outer-membrane protein polyantigens. *J Med Microbiol* 2000, 49(5): 457-465.

68. Qu Z, Cheng X, de la Maza L M, Peterson E M. Analysis of the humoral response elicited in mice by a chimeric peptide representing variable segments I and IV of the major outer membrane protein of *Chlamydia trachomatis*. *Vaccine* 1994, 12(6): 557-564.
69. Peterson E M, Cheng X, Qu Z, de la Maza L M. The effect of orientation within a chimeric peptide on the immunogenicity of *Chlamydia trachomatis* epitopes. *Mol Immunol* 1996, 33(4-5): 335-339.
70. Caldwell H D, Kromhout J, Schachter J. Purification and partial characterization of the major outer membrane protein of *Chlamydia trachomatis*. *Infect Immun* 1981, 31(3): 1161-1176.
71. Ravn P, Demissie A, Eguale T, Wondwosson H, Lein D, Amoudy H A, et al Human T cell responses to the ESAT-6 antigen from *Mycobacterium tuberculosis*. *J Infect Dis* 1999, 179(3): 637-645.
72. Stiyhn A, Pedersen L O, Romme T, Holm C B, Holm A, Buus S. Peptide binding specificity of major histocompatibility complex class I resolved into an array of apparently independent subspecificities: quantitation by peptide libraries and improved prediction of binding *Eur J Immunol* 1996, 26(8): 1911-1918.
73. Harboe M, Oettinger T, Wiker H G, Rosenkrands I, Andersen P. Evidence for occurrence of the ESAT-6 protein in *Mycobacterium tuberculosis* and virulent *Mycobacterium bovis* and for its absence in *Mycobacterium bovis* BCG. *Infect Immun* 1996, 64(1): 16-22.
74. Volp K, Mathews S, Timms P, Hafner L. Peptide immunization of guinea pigs against *Chlamydia psittaci* (GPIC agent) infection induces good vaginal secretion antibody response, in vitro neutralization and partial protection against live challenge. *Immunol Cell Biol* 2001, 79(3): 245-250.
75. Hinton H J, Jegerlehner A, Bachmann M F. Pattern recognition by B cells: the role of antigen repetitiveness versus Toll-like receptors. *Current topics in microbiology and immunology* 2008, 319: 1-15.
76. Kim S K, DeMars R. Epitope clusters in the major outer membrane protein of *Chlamydia trachomatis*. *Curr Opin Immunol* 2001, 13(4): 429-436.
77. Findlay H E, McClafferly H, Ashley R H. Surface expression, single-channel analysis and membrane topology of recombinant *Chlamydia trachomatis* Major Outer Membrane Protein. *BMC Microbiol* 2005, 5: 5.
78. Cobbold S P, Jayasuriya A, Nash A, Prospero T D, Waldmann H Therapy with monoclonal antibodies by elimination of T-cell subsets in vivo. *Nature* 1984, 312 (5994): 548-551.
79. Qin S, Cobbold S, Tighe H, Benjamin R, Waldmann H CD4 monoclonal antibody pairs for immunosuppression and tolerance induction. *Eur J Immunol* 1987, 17(8): 1159-1165.

U.S. patent application Ser. No. 14/216,403, filed Mar. 17, 2014, U.S. Provisional Patent Application No. 61/802,907, filed Mar. 18, 2013, Danish Patent Application Nos. PA 2013 00155, filed Mar. 18, 2013, and PA 2013 00684, Dec. 11, 2013, including sequence listings, are incorporated herein by reference in their entireties.

SEQUENCE LISTING

```
<160> NUMBER OF SEQ ID NOS: 255

<210> SEQ ID NO 1
<211> LENGTH: 20
<212> TYPE: PRT
<213> ORGANISM: Chlamydia trachomatis

<400> SEQUENCE: 1

Ala Lys Pro Thr Thr Asp Thr Gly Asn Ser Ala Ala Pro Ser Thr Leu
1               5                   10                  15

Thr Ala Arg Glu
            20

<210> SEQ ID NO 2
<211> LENGTH: 20
<212> TYPE: PRT
<213> ORGANISM: Chlamydia trachomatis

<400> SEQUENCE: 2

Asp Lys Pro Thr Ser Thr Thr Gly Asn Ala Thr Ala Pro Thr Thr Leu
1               5                   10                  15

Thr Ala Arg Glu
            20

<210> SEQ ID NO 3
<211> LENGTH: 21
<212> TYPE: PRT
<213> ORGANISM: Chlamydia trachomatis

<400> SEQUENCE: 3

Glu Ala Leu Ala Gly Ala Ser Gly Asn Thr Thr Ser Thr Leu Ser Lys
1               5                   10                  15
```

Leu Val Glu Arg Thr
            20

<210> SEQ ID NO 4
<211> LENGTH: 21
<212> TYPE: PRT
<213> ORGANISM: Chlamydia trachomatis

<400> SEQUENCE: 4

Glu Ala Leu Ala Gly Ala Ser Gly Asn Thr Thr Ser Thr Leu Ser Lys
1               5                   10                  15

Leu Val Glu Arg Thr
            20

<210> SEQ ID NO 5
<211> LENGTH: 22
<212> TYPE: PRT
<213> ORGANISM: Chlamydia trachomatis

<400> SEQUENCE: 5

Ala Ala Pro Thr Thr Lys Asp Ile Ala Gly Leu Glu Asn Asp Pro Thr
1               5                   10                  15

Thr Asn Val Ala Arg Pro
            20

<210> SEQ ID NO 6
<211> LENGTH: 22
<212> TYPE: PRT
<213> ORGANISM: Chlamydia trachomatis

<400> SEQUENCE: 6

Ala Ala Pro Thr Thr Ser Asp Val Ala Gly Leu Gln Asn Asp Pro Thr
1               5                   10                  15

Thr Asn Val Ala Arg Pro
            20

<210> SEQ ID NO 7
<211> LENGTH: 30
<212> TYPE: PRT
<213> ORGANISM: Chlamydia trachomatis

<400> SEQUENCE: 7

Asp Ala Ile Ser Met Arg Val Gly Tyr Tyr Gly Asp Phe Val Phe Asp
1               5                   10                  15

Arg Val Leu Lys Thr Asp Val Asn Lys Glu Phe Gln Met Gly
            20                  25                  30

<210> SEQ ID NO 8
<211> LENGTH: 18
<212> TYPE: PRT
<213> ORGANISM: Chlamydia trachomatis

<400> SEQUENCE: 8

Asn Pro Ala Tyr Gly Arg His Met Gln Asp Ala Glu Met Phe Thr Asn
1               5                   10                  15

Ala Ala

<210> SEQ ID NO 9
<211> LENGTH: 59
<212> TYPE: PRT
<213> ORGANISM: Chlamydia trachomatis

<400> SEQUENCE: 9

-continued

Ala Ile Ser Met Arg Val Gly Tyr Tyr Gly Asp Phe Val Phe Asp Arg
1               5                   10                  15

Val Leu Lys Thr Asp Val Asn Lys Glu Phe Gln Met Gly Ala Lys Pro
            20                  25                  30

Thr Thr Asp Thr Gly Asn Ser Ala Ala Pro Ser Thr Leu Thr Ala Arg
        35                  40                  45

Glu Asn Pro Ala Tyr Gly Arg His Met Gln Asp
    50                  55

<210> SEQ ID NO 10
<211> LENGTH: 59
<212> TYPE: PRT
<213> ORGANISM: Chlamydia trachomatis

<400> SEQUENCE: 10

Ala Ile Ser Met Arg Met Gly Tyr Tyr Gly Asp Phe Val Phe Asp Arg
1               5                   10                  15

Val Leu Lys Thr Asp Val Asn Lys Glu Phe Gln Met Gly Asp Lys Pro
            20                  25                  30

Thr Ser Thr Thr Gly Asn Ala Thr Ala Pro Thr Thr Leu Thr Ala Arg
        35                  40                  45

Glu Asn Pro Ala Tyr Gly Arg His Met Gln Asp
    50                  55

<210> SEQ ID NO 11
<211> LENGTH: 60
<212> TYPE: PRT
<213> ORGANISM: Chlamydia trachomatis

<400> SEQUENCE: 11

Ala Ile Ser Met Arg Met Gly Tyr Tyr Gly Asp Phe Val Phe Asp Arg
1               5                   10                  15

Val Leu Lys Thr Asp Val Asn Lys Glu Phe Glu Met Gly Glu Ala Leu
            20                  25                  30

Ala Gly Ala Ser Gly Asn Thr Thr Ser Thr Leu Ser Lys Leu Val Glu
        35                  40                  45

Arg Thr Asn Pro Ala Tyr Gly Lys His Met Gln Asp
    50                  55                  60

<210> SEQ ID NO 12
<211> LENGTH: 60
<212> TYPE: PRT
<213> ORGANISM: Chlamydia trachomatis

<400> SEQUENCE: 12

Ala Ile Ser Met Arg Met Gly Tyr Tyr Gly Asp Phe Val Phe Asp Arg
1               5                   10                  15

Val Leu Lys Thr Asp Val Asn Lys Glu Phe Glu Met Gly Glu Ala Leu
            20                  25                  30

Ala Gly Ala Ser Gly Asn Thr Thr Ser Thr Leu Ser Lys Leu Val Glu
        35                  40                  45

Arg Thr Asn Pro Ala Tyr Gly Lys His Met Gln Asp
    50                  55                  60

<210> SEQ ID NO 13
<211> LENGTH: 61
<212> TYPE: PRT
<213> ORGANISM: Chlamydia trachomatis

```
<400> SEQUENCE: 13

Ala Ile Ser Met Arg Met Gly Tyr Tyr Gly Asp Phe Val Phe Asp Arg
1               5                   10                  15

Val Leu Lys Thr Asp Val Asn Lys Glu Phe Gln Met Gly Ala Ala Pro
            20                  25                  30

Thr Thr Lys Asp Ile Ala Gly Leu Glu Asn Asp Pro Thr Thr Asn Val
        35                  40                  45

Ala Arg Pro Asn Pro Ala Tyr Gly Lys His Met Gln Asp
    50                  55                  60

<210> SEQ ID NO 14
<211> LENGTH: 61
<212> TYPE: PRT
<213> ORGANISM: Chlamydia trachomatis

<400> SEQUENCE: 14

Ala Ile Ser Met Arg Met Gly Tyr Tyr Gly Asp Phe Val Phe Asp Arg
1               5                   10                  15

Val Leu Lys Thr Asp Val Asn Lys Glu Phe Gln Met Gly Ala Ala Pro
            20                  25                  30

Thr Thr Ser Asp Val Ala Gly Leu Gln Asn Asp Pro Thr Thr Asn Val
        35                  40                  45

Ala Arg Pro Asn Pro Ala Tyr Gly Lys His Met Gln Asp
    50                  55                  60

<210> SEQ ID NO 15
<211> LENGTH: 30
<212> TYPE: PRT
<213> ORGANISM: Chlamydia trachomatis

<400> SEQUENCE: 15

Ser Ala Thr Ala Ile Phe Asp Thr Thr Thr Leu Asn Pro Thr Ile Ala
1               5                   10                  15

Gly Ala Gly Asp Val Lys Thr Gly Ala Glu Gly Gln Leu Gly
            20                  25                  30

<210> SEQ ID NO 16
<211> LENGTH: 30
<212> TYPE: PRT
<213> ORGANISM: Chlamydia trachomatis

<400> SEQUENCE: 16

Ser Ala Thr Ala Ile Phe Asp Thr Thr Thr Leu Asn Pro Thr Ile Ala
1               5                   10                  15

Gly Ala Gly Asp Val Lys Ala Ser Ala Glu Gly Gln Leu Gly
            20                  25                  30

<210> SEQ ID NO 17
<211> LENGTH: 31
<212> TYPE: PRT
<213> ORGANISM: Chlamydia trachomatis

<400> SEQUENCE: 17

Leu Val Thr Pro Val Val Asp Ile Thr Thr Leu Asn Pro Thr Ile Ala
1               5                   10                  15

Gly Cys Gly Ser Val Ala Gly Ala Asn Thr Glu Gly Gln Ile Ser
            20                  25                  30

<210> SEQ ID NO 18
<211> LENGTH: 31
```

```
<212> TYPE: PRT
<213> ORGANISM: Chlamydia trachomatis

<400> SEQUENCE: 18

Leu Ala Lys Pro Val Val Asp Ile Thr Thr Leu Asn Pro Thr Ile Ala
1               5                   10                  15

Gly Cys Gly Ser Val Val Ala Ala Asn Ser Glu Gly Gln Ile Ser
            20                  25                  30

<210> SEQ ID NO 19
<211> LENGTH: 31
<212> TYPE: PRT
<213> ORGANISM: Chlamydia trachomatis

<400> SEQUENCE: 19

Leu Ala Glu Ala Ile Leu Asp Val Thr Thr Leu Asn Pro Thr Ile Ala
1               5                   10                  15

Gly Lys Gly Thr Val Val Ala Ser Gly Ser Asp Asn Asp Leu Ala
            20                  25                  30

<210> SEQ ID NO 20
<211> LENGTH: 31
<212> TYPE: PRT
<213> ORGANISM: Chlamydia trachomatis

<400> SEQUENCE: 20

Leu Ala Glu Ala Ile Leu Asp Val Thr Thr Leu Asn Pro Thr Ile Ala
1               5                   10                  15

Gly Lys Gly Thr Val Val Ala Ser Gly Ser Glu Asn Asp Leu Ala
            20                  25                  30

<210> SEQ ID NO 21
<211> LENGTH: 39
<212> TYPE: PRT
<213> ORGANISM: Chlamydia trachomatis

<400> SEQUENCE: 21

Glu Trp Gln Ala Ser Leu Ala Leu Ser Tyr Arg Leu Asn Met Phe Thr
1               5                   10                  15

Pro Tyr Ile Gly Val Lys Trp Ser Arg Ala Ser Phe Asp Ala Asp Thr
            20                  25                  30

Ile Arg Ile Ala Gln Pro Lys
        35

<210> SEQ ID NO 22
<211> LENGTH: 30
<212> TYPE: PRT
<213> ORGANISM: Chlamydia trachomatis

<400> SEQUENCE: 22

Asp Thr Met Gln Ile Val Ser Leu Gln Leu Asn Lys Met Lys Ser Arg
1               5                   10                  15

Lys Ser Cys Gly Ile Ala Val Gly Thr Thr Ile Val Asp Ala
            20                  25                  30

<210> SEQ ID NO 23
<211> LENGTH: 68
<212> TYPE: PRT
<213> ORGANISM: Chlamydia trachomatis

<400> SEQUENCE: 23

Asn Met Phe Thr Pro Tyr Ile Gly Val Lys Trp Ser Arg Ala Ser Phe
```

```
                1               5                   10                  15
Asp Ala Asp Thr Ile Arg Ile Ala Gln Pro Lys Ser Ala Thr Ala Ile
                20                  25                  30

Phe Asp Thr Thr Thr Leu Asn Pro Thr Ile Ala Gly Ala Gly Asp Val
                35                  40                  45

Lys Thr Gly Ala Glu Gly Gln Leu Gly Asp Thr Met Gln Ile Val Ser
            50                  55                  60

Leu Gln Leu Asn
65

<210> SEQ ID NO 24
<211> LENGTH: 68
<212> TYPE: PRT
<213> ORGANISM: Chlamydia trachomatis

<400> SEQUENCE: 24

Asn Met Phe Thr Pro Tyr Ile Gly Val Lys Trp Ser Arg Ala Ser Phe
1               5                   10                  15

Asp Ala Asp Thr Ile Arg Ile Ala Gln Pro Lys Ser Ala Thr Ala Ile
                20                  25                  30

Phe Asp Thr Thr Thr Leu Asn Pro Thr Ile Ala Gly Ala Gly Asp Val
                35                  40                  45

Lys Ala Ser Ala Glu Gly Gln Leu Gly Asp Thr Met Gln Ile Val Ser
            50                  55                  60

Leu Gln Leu Asn
65

<210> SEQ ID NO 25
<211> LENGTH: 69
<212> TYPE: PRT
<213> ORGANISM: Chlamydia trachomatis

<400> SEQUENCE: 25

Asn Met Phe Thr Pro Tyr Ile Gly Val Lys Trp Ser Arg Ala Ser Phe
1               5                   10                  15

Asp Ser Asp Thr Ile Arg Ile Ala Gln Pro Arg Leu Val Thr Pro Val
                20                  25                  30

Val Asp Ile Thr Thr Leu Asn Pro Thr Ile Ala Gly Cys Gly Ser Val
                35                  40                  45

Ala Gly Ala Asn Thr Glu Gly Gln Ile Ser Asp Thr Met Gln Ile Val
            50                  55                  60

Ser Leu Gln Leu Asn
65

<210> SEQ ID NO 26
<211> LENGTH: 69
<212> TYPE: PRT
<213> ORGANISM: Chlamydia trachomatis

<400> SEQUENCE: 26

Asn Met Phe Thr Pro Tyr Ile Gly Val Lys Trp Ser Arg Ala Ser Phe
1               5                   10                  15

Asp Ser Asn Thr Ile Arg Ile Ala Gln Pro Lys Leu Ala Lys Pro Val
                20                  25                  30

Val Asp Ile Thr Thr Leu Asn Pro Thr Ile Ala Gly Cys Gly Ser Val
                35                  40                  45

Val Ala Ala Asn Ser Glu Gly Gln Ile Ser Asp Thr Met Gln Ile Val
            50                  55                  60
```

```
Ser Leu Gln Leu Asn
65

<210> SEQ ID NO 27
<211> LENGTH: 69
<212> TYPE: PRT
<213> ORGANISM: Chlamydia trachomatis

<400> SEQUENCE: 27

Asn Met Phe Thr Pro Tyr Ile Gly Val Lys Trp Ser Arg Val Ser Phe
1               5                   10                  15

Asp Ala Asp Thr Ile Arg Ile Ala Gln Pro Lys Leu Ala Glu Ala Ile
            20                  25                  30

Leu Asp Val Thr Thr Leu Asn Pro Thr Ile Ala Gly Lys Gly Thr Val
        35                  40                  45

Val Ala Ser Gly Ser Asp Asn Asp Leu Ala Asp Thr Met Gln Ile Val
    50                  55                  60

Ser Leu Gln Leu Asn
65

<210> SEQ ID NO 28
<211> LENGTH: 69
<212> TYPE: PRT
<213> ORGANISM: Chlamydia trachomatis

<400> SEQUENCE: 28

Asn Met Phe Thr Pro Tyr Ile Gly Val Lys Trp Ser Arg Val Ser Phe
1               5                   10                  15

Asp Ala Asp Thr Ile Arg Ile Ala Gln Pro Lys Leu Ala Glu Ala Ile
            20                  25                  30

Leu Asp Val Thr Thr Leu Asn Pro Thr Ile Ala Gly Lys Gly Thr Val
        35                  40                  45

Val Ala Ser Gly Ser Glu Asn Asp Leu Ala Asp Thr Met Gln Ile Val
    50                  55                  60

Ser Leu Gln Leu Asn
65

<210> SEQ ID NO 29
<211> LENGTH: 21
<212> TYPE: PRT
<213> ORGANISM: Chlamydia trachomatis

<400> SEQUENCE: 29

Asp Asn Glu Asn Gln Lys Thr Val Lys Ala Glu Ser Val Pro Asn Met
1               5                   10                  15

Ser Phe Asp Gln Ser
            20

<210> SEQ ID NO 30
<211> LENGTH: 21
<212> TYPE: PRT
<213> ORGANISM: Chlamydia trachomatis

<400> SEQUENCE: 30

Asp Asn Glu Asn Gln Ser Thr Val Lys Thr Asn Ser Val Pro Asn Met
1               5                   10                  15

Ser Leu Asp Gln Ser
            20
```

```
<210> SEQ ID NO 31
<211> LENGTH: 21
<212> TYPE: PRT
<213> ORGANISM: Chlamydia trachomatis

<400> SEQUENCE: 31

Asp Gly Val Asn Ala Thr Lys Pro Ala Ala Asp Ser Ile Pro Asn Val
1               5                   10                  15

Gln Leu Asn Gln Ser
            20

<210> SEQ ID NO 32
<211> LENGTH: 21
<212> TYPE: PRT
<213> ORGANISM: Chlamydia trachomatis

<400> SEQUENCE: 32

Asp Ser Glu Asn Ala Thr Gln Pro Ala Ala Thr Ser Ile Pro Asn Val
1               5                   10                  15

Gln Leu Asn Gln Ser
            20

<210> SEQ ID NO 33
<211> LENGTH: 22
<212> TYPE: PRT
<213> ORGANISM: Chlamydia trachomatis

<400> SEQUENCE: 33

Thr Lys Thr Gln Ser Ser Asn Phe Asn Thr Ala Lys Leu Ile Pro Asn
1               5                   10                  15

Ala Ala Leu Asn Gln Ala
            20

<210> SEQ ID NO 34
<211> LENGTH: 22
<212> TYPE: PRT
<213> ORGANISM: Chlamydia trachomatis

<400> SEQUENCE: 34

Thr Lys Thr Gln Ala Ser Ser Phe Asn Thr Ala Asn Leu Phe Pro Asn
1               5                   10                  15

Thr Ala Leu Asn Gln Ala
            20

<210> SEQ ID NO 35
<211> LENGTH: 23
<212> TYPE: PRT
<213> ORGANISM: Chlamydia trachomatis

<400> SEQUENCE: 35

Thr Leu Gly Ala Thr Ser Gly Tyr Leu Lys Gly Asn Ser Ala Ser Phe
1               5                   10                  15

Asn Leu Val Gly Leu Phe Gly
            20

<210> SEQ ID NO 36
<211> LENGTH: 22
<212> TYPE: PRT
<213> ORGANISM: Chlamydia trachomatis

<400> SEQUENCE: 36

Val Val Glu Leu Tyr Thr Asp Thr Thr Phe Ala Trp Ser Val Gly Ala
1               5                   10                  15
```

Arg Ala Ala Leu Trp Glu
            20

<210> SEQ ID NO 37
<211> LENGTH: 14
<212> TYPE: PRT
<213> ORGANISM: Chlamydia trachomatis

<400> SEQUENCE: 37

Lys Glu Phe Pro Leu Asp Leu Thr Ala Gly Thr Asp Ala Ala
1               5                   10

<210> SEQ ID NO 38
<211> LENGTH: 14
<212> TYPE: PRT
<213> ORGANISM: Chlamydia trachomatis

<400> SEQUENCE: 38

Gln Glu Phe Pro Leu Ala Leu Ile Ala Gly Thr Asp Ala Ala
1               5                   10

<210> SEQ ID NO 39
<211> LENGTH: 14
<212> TYPE: PRT
<213> ORGANISM: Chlamydia trachomatis

<400> SEQUENCE: 39

Lys Glu Phe Pro Leu Asp Leu Thr Ala Gly Thr Asp Ala Ala
1               5                   10

<210> SEQ ID NO 40
<211> LENGTH: 14
<212> TYPE: PRT
<213> ORGANISM: Chlamydia trachomatis

<400> SEQUENCE: 40

Gln Glu Phe Pro Leu Ala Leu Thr Ala Gly Thr Asp Ala Ala
1               5                   10

<210> SEQ ID NO 41
<211> LENGTH: 14
<212> TYPE: PRT
<213> ORGANISM: Chlamydia trachomatis

<400> SEQUENCE: 41

Ala Glu Phe Pro Leu Asp Ile Thr Ala Gly Thr Glu Ala Ala
1               5                   10

<210> SEQ ID NO 42
<211> LENGTH: 14
<212> TYPE: PRT
<213> ORGANISM: Chlamydia trachomatis

<400> SEQUENCE: 42

Ala Glu Phe Pro Leu Asp Ile Thr Ala Gly Thr Glu Ala Ala
1               5                   10

<210> SEQ ID NO 43
<211> LENGTH: 38
<212> TYPE: PRT
<213> ORGANISM: Chlamydia trachomatis

<400> SEQUENCE: 43

Ala Thr Leu Gly Ala Ser Phe Gln Tyr Ala Gln Ser Lys Pro Lys Val

```
                1               5                  10                 15
            Glu Glu Leu Asn Val Leu Cys Asn Ala Ala Glu Phe Thr Ile Asn Lys
                            20                  25                 30

Pro Lys Gly Tyr Val Gly
                        35

<210> SEQ ID NO 44
<211> LENGTH: 35
<212> TYPE: PRT
<213> ORGANISM: Chlamydia trachomatis

<400> SEQUENCE: 44

Thr Gly Thr Lys Asp Ala Ser Ile Asp Tyr His Glu Trp Gln Ala Ser
1               5                   10                  15

Leu Ala Leu Ser Tyr Arg Leu Asn Met Phe Thr Pro Tyr Ile Gly Val
                20                  25                  30

Lys Trp Ser
        35

<210> SEQ ID NO 45
<211> LENGTH: 127
<212> TYPE: PRT
<213> ORGANISM: Chlamydia trachomatis

<400> SEQUENCE: 45

Ala Ile Ser Met Arg Val Gly Tyr Tyr Gly Asp Phe Val Phe Asp Arg
1               5                   10                  15

Val Leu Lys Thr Asp Val Asn Lys Glu Phe Gln Met Gly Ala Lys Pro
                20                  25                  30

Thr Thr Asp Thr Gly Asn Ser Ala Ala Pro Ser Thr Leu Thr Ala Arg
            35                  40                  45

Glu Asn Pro Ala Tyr Gly Arg His Met Gln Asp Asn Met Phe Thr Pro
        50                  55                  60

Tyr Ile Gly Val Lys Trp Ser Arg Ala Ser Phe Asp Ala Asp Thr Ile
65                  70                  75                  80

Arg Ile Ala Gln Pro Lys Ser Ala Thr Ala Ile Phe Asp Thr Thr Thr
                85                  90                  95

Leu Asn Pro Thr Ile Ala Gly Ala Gly Asp Val Lys Thr Gly Ala Glu
            100                 105                 110

Gly Gln Leu Gly Asp Thr Met Gln Ile Val Ser Leu Gln Leu Asn
        115                 120                 125

<210> SEQ ID NO 46
<211> LENGTH: 383
<212> TYPE: PRT
<213> ORGANISM: Chlamydia trachomatis

<400> SEQUENCE: 46

Ala Ile Ser Met Arg Val Gly Tyr Tyr Gly Asp Phe Val Phe Asp Arg
1               5                   10                  15

Val Leu Lys Thr Asp Val Asn Lys Glu Phe Gln Met Gly Ala Lys Pro
                20                  25                  30

Thr Thr Asp Thr Gly Asn Ser Ala Ala Pro Ser Thr Leu Thr Ala Arg
            35                  40                  45

Glu Asn Pro Ala Tyr Gly Arg His Met Gln Asp Asn Met Phe Thr Pro
        50                  55                  60

Tyr Ile Gly Val Lys Trp Ser Arg Ala Ser Phe Asp Ala Asp Thr Ile
65                  70                  75                  80
```

```
Arg Ile Ala Gln Pro Lys Ser Ala Thr Ala Ile Phe Asp Thr Thr Thr
                    85                  90                  95

Leu Asn Pro Thr Ile Ala Gly Ala Gly Asp Val Lys Thr Gly Ala Glu
                100                 105                 110

Gly Gln Leu Gly Asp Thr Met Gln Ile Val Ser Leu Gln Leu Asn Ala
            115                 120                 125

Ile Ser Met Arg Met Gly Tyr Tyr Gly Asp Phe Val Phe Asp Arg Val
        130                 135                 140

Leu Lys Thr Asp Val Asn Lys Glu Phe Gln Met Gly Asp Lys Pro Thr
145                 150                 155                 160

Ser Thr Thr Gly Asn Ala Thr Ala Pro Thr Thr Leu Thr Ala Arg Glu
                165                 170                 175

Asn Pro Ala Tyr Gly Arg His Met Gln Asp Asn Met Phe Thr Pro Tyr
                180                 185                 190

Ile Gly Val Lys Trp Ser Arg Ala Ser Phe Asp Ala Asp Thr Ile Arg
                195                 200                 205

Ile Ala Gln Pro Lys Ser Ala Thr Ala Ile Phe Asp Thr Thr Thr Leu
        210                 215                 220

Asn Pro Thr Ile Ala Gly Ala Gly Asp Val Lys Ala Ser Ala Glu Gly
225                 230                 235                 240

Gln Leu Gly Asp Thr Met Gln Ile Val Ser Leu Gln Leu Asn Ala Ile
                245                 250                 255

Ser Met Arg Met Gly Tyr Tyr Gly Asp Phe Val Phe Asp Arg Val Leu
                260                 265                 270

Lys Thr Asp Val Asn Lys Glu Phe Glu Met Gly Glu Ala Leu Ala Gly
                275                 280                 285

Ala Ser Gly Asn Thr Thr Ser Thr Leu Ser Lys Leu Val Glu Arg Thr
        290                 295                 300

Asn Pro Ala Tyr Gly Lys His Met Gln Asp Asn Met Phe Thr Pro Tyr
305                 310                 315                 320

Ile Gly Val Lys Trp Ser Arg Ala Ser Phe Asp Ser Asp Thr Ile Arg
                325                 330                 335

Ile Ala Gln Pro Arg Leu Val Thr Pro Val Val Asp Ile Thr Thr Leu
        340                 345                 350

Asn Pro Thr Ile Ala Gly Ser Gly Ser Val Ala Gly Ala Asn Thr Glu
                355                 360                 365

Gly Gln Ile Ser Asp Thr Met Gln Ile Val Ser Leu Gln Leu Asn
            370                 375                 380

<210> SEQ ID NO 47
<211> LENGTH: 419
<212> TYPE: PRT
<213> ORGANISM: Chlamydia trachomatis

<400> SEQUENCE: 47

Ala Ile Ser Met Arg Val Gly Tyr Tyr Gly Asp Phe Val Phe Asp Arg
1               5                   10                  15

Val Leu Lys Thr Asp Val Asn Lys Glu Phe Gln Met Gly Ala Lys Pro
                20                  25                  30

Thr Thr Asp Thr Gly Asn Ser Ala Ala Pro Ser Thr Leu Thr Ala Arg
            35                  40                  45

Glu Asn Pro Ala Tyr Gly Arg His Met Gln Asp Glu Trp Gln Ala Ser
        50                  55                  60

Leu Ala Leu Ser Tyr Arg Leu Asn Met Phe Thr Pro Tyr Ile Gly Val
```

```
65                  70                  75                  80

Lys Trp Ser Arg Ala Ser Phe Asp Ala Asp Thr Ile Arg Ile Ala Gln
                85                  90                  95

Pro Lys Ser Ala Thr Ala Ile Phe Asp Thr Thr Thr Leu Asn Pro Thr
            100                 105                 110

Ile Ala Gly Ala Gly Asp Val Lys Thr Gly Ala Glu Gly Gln Leu Gly
        115                 120                 125

Asp Thr Met Gln Ile Val Ser Leu Gln Leu Asn Ala Ile Ser Met Arg
    130                 135                 140

Met Gly Tyr Tyr Gly Asp Phe Val Phe Asp Arg Val Leu Lys Thr Asp
145                 150                 155                 160

Val Asn Lys Glu Phe Gln Met Gly Asp Lys Pro Thr Ser Thr Thr Gly
                165                 170                 175

Asn Ala Thr Ala Pro Thr Thr Leu Thr Ala Arg Glu Asn Pro Ala Tyr
            180                 185                 190

Gly Arg His Met Gln Asp Glu Trp Gln Ala Ser Leu Ala Leu Ser Tyr
        195                 200                 205

Arg Leu Asn Met Phe Thr Pro Tyr Ile Gly Val Lys Trp Ser Arg Ala
    210                 215                 220

Ser Phe Asp Ala Asp Thr Ile Arg Ile Ala Gln Pro Lys Ser Ala Thr
225                 230                 235                 240

Ala Ile Phe Asp Thr Thr Thr Leu Asn Pro Thr Ile Ala Gly Ala Gly
                245                 250                 255

Asp Val Lys Ala Ser Ala Glu Gly Gln Leu Gly Asp Thr Met Gln Ile
            260                 265                 270

Val Ser Leu Gln Leu Asn Ala Ile Ser Met Arg Met Gly Tyr Tyr Gly
        275                 280                 285

Asp Phe Val Phe Asp Arg Val Leu Lys Thr Asp Val Asn Lys Glu Phe
    290                 295                 300

Glu Met Gly Glu Ala Leu Ala Gly Ala Ser Gly Asn Thr Thr Ser Thr
305                 310                 315                 320

Leu Ser Lys Leu Val Glu Arg Thr Asn Pro Ala Tyr Gly Lys His Met
                325                 330                 335

Gln Asp Glu Trp Gln Ala Ser Leu Ser Leu Ser Tyr Arg Leu Asn Met
            340                 345                 350

Phe Thr Pro Tyr Ile Gly Val Lys Trp Ser Arg Ala Ser Phe Asp Ser
        355                 360                 365

Asp Thr Ile Arg Ile Ala Gln Pro Arg Leu Val Thr Pro Val Val Asp
    370                 375                 380

Ile Thr Thr Leu Asn Pro Thr Ile Ala Gly Ser Gly Ser Val Ala Gly
385                 390                 395                 400

Ala Asn Thr Glu Gly Gln Ile Ser Asp Thr Met Gln Ile Val Ser Leu
                405                 410                 415

Gln Leu Asn

<210> SEQ ID NO 48
<211> LENGTH: 844
<212> TYPE: PRT
<213> ORGANISM: Chlamydia trachomatis

<400> SEQUENCE: 48

Ala Ile Ser Met Arg Val Gly Tyr Tyr Gly Asp Phe Val Phe Asp Arg
1               5                   10                  15

Val Leu Lys Thr Asp Val Asn Lys Glu Phe Gln Met Gly Ala Lys Pro

-continued

```
                20                  25                  30
Thr Thr Asp Thr Gly Asn Ser Ala Ala Pro Ser Thr Leu Thr Ala Arg
            35                  40                  45
Glu Asn Pro Ala Tyr Gly Arg His Met Gln Asp Glu Trp Gln Ala Ser
        50                  55                  60
Leu Ala Leu Ser Tyr Arg Leu Asn Met Phe Thr Pro Tyr Ile Gly Val
65                  70                  75                  80
Lys Trp Ser Arg Ala Ser Phe Asp Ala Asp Thr Ile Arg Ile Ala Gln
                85                  90                  95
Pro Lys Ser Ala Thr Ala Ile Phe Asp Thr Thr Thr Leu Asn Pro Thr
            100                 105                 110
Ile Ala Gly Ala Gly Asp Val Lys Thr Gly Ala Glu Gly Gln Leu Gly
        115                 120                 125
Asp Thr Met Gln Ile Val Ser Leu Gln Leu Asn Ala Ile Ser Met Arg
        130                 135                 140
Met Gly Tyr Tyr Gly Asp Phe Val Phe Asp Arg Val Leu Lys Thr Asp
145                 150                 155                 160
Val Asn Lys Glu Phe Gln Met Gly Asp Lys Pro Thr Ser Thr Thr Gly
                165                 170                 175
Asn Ala Thr Ala Pro Thr Thr Leu Thr Ala Arg Glu Asn Pro Ala Tyr
            180                 185                 190
Gly Arg His Met Gln Asp Glu Trp Gln Ala Ser Leu Ala Leu Ser Tyr
        195                 200                 205
Arg Leu Asn Met Phe Thr Pro Tyr Ile Gly Val Lys Trp Ser Arg Ala
        210                 215                 220
Ser Phe Asp Ala Asp Thr Ile Arg Ile Ala Gln Pro Lys Ser Ala Thr
225                 230                 235                 240
Ala Ile Phe Asp Thr Thr Thr Leu Asn Pro Thr Ile Ala Gly Ala Gly
                245                 250                 255
Asp Val Lys Ala Ser Ala Glu Gly Gln Leu Gly Asp Thr Met Gln Ile
            260                 265                 270
Val Ser Leu Gln Leu Asn Ala Ile Ser Met Arg Met Gly Tyr Tyr Gly
        275                 280                 285
Asp Phe Val Phe Asp Arg Val Leu Lys Thr Asp Val Asn Lys Glu Phe
        290                 295                 300
Glu Met Gly Glu Ala Leu Ala Gly Ala Ser Gly Asn Thr Thr Ser Thr
305                 310                 315                 320
Leu Ser Lys Leu Val Glu Arg Thr Asn Pro Ala Tyr Gly Lys His Met
                325                 330                 335
Gln Asp Glu Trp Gln Ala Ser Leu Ser Leu Ser Tyr Arg Leu Asn Met
            340                 345                 350
Phe Thr Pro Tyr Ile Gly Val Lys Trp Ser Arg Ala Ser Phe Asp Ser
        355                 360                 365
Asp Thr Ile Arg Ile Ala Gln Pro Arg Leu Val Thr Pro Val Val Asp
        370                 375                 380
Ile Thr Thr Leu Asn Pro Thr Ile Ala Gly Ser Gly Ser Val Ala Gly
385                 390                 395                 400
Ala Asn Thr Glu Gly Gln Ile Ser Asp Thr Met Gln Ile Val Ser Leu
                405                 410                 415
Gln Leu Asn Ala Ile Ser Met Arg Met Gly Tyr Tyr Gly Asp Phe Val
            420                 425                 430
Phe Asp Arg Val Leu Lys Thr Asp Val Asn Lys Glu Phe Glu Met Gly
        435                 440                 445
```

Glu Ala Leu Ala Gly Ala Ser Gly Asn Thr Thr Ser Thr Leu Ser Lys
450                 455                 460

Leu Val Glu Arg Thr Asn Pro Ala Tyr Gly Lys His Met Gln Asp Glu
465                 470                 475                 480

Trp Gln Ala Ser Leu Ser Leu Ser Tyr Arg Leu Asn Met Phe Thr Pro
            485                 490                 495

Tyr Ile Gly Val Lys Trp Ser Arg Ala Ser Phe Asp Ser Asn Thr Ile
            500                 505                 510

Arg Ile Ala Gln Pro Lys Leu Ala Lys Pro Val Val Asp Ile Thr Thr
            515                 520                 525

Leu Asn Pro Thr Ile Ala Gly Ser Gly Ser Val Val Ala Ala Asn Ser
530                 535                 540

Glu Gly Gln Ile Ser Asp Thr Met Gln Ile Val Ser Leu Gln Leu Asn
545                 550                 555                 560

Ala Ile Ser Met Arg Met Gly Tyr Tyr Gly Asp Phe Val Phe Asp Arg
                565                 570                 575

Val Leu Lys Thr Asp Val Asn Lys Glu Phe Gln Met Gly Ala Ala Pro
            580                 585                 590

Thr Thr Lys Asp Ile Ala Gly Leu Glu Asn Asp Pro Thr Thr Asn Val
            595                 600                 605

Ala Arg Pro Asn Pro Ala Tyr Gly Lys His Met Gln Asp Glu Trp Gln
610                 615                 620

Ala Ser Leu Ala Leu Ser Tyr Arg Leu Asn Met Phe Thr Pro Tyr Ile
625                 630                 635                 640

Gly Val Lys Trp Ser Arg Val Ser Phe Asp Ala Asp Thr Ile Arg Ile
                645                 650                 655

Ala Gln Pro Lys Leu Ala Glu Ala Ile Leu Asp Val Thr Thr Leu Asn
            660                 665                 670

Pro Thr Ile Ala Gly Lys Gly Thr Val Val Ala Ser Gly Ser Asp Asn
            675                 680                 685

Asp Leu Ala Asp Thr Met Gln Ile Val Ser Leu Gln Leu Asn Ala Ile
690                 695                 700

Ser Met Arg Met Gly Tyr Tyr Gly Asp Phe Val Phe Asp Arg Val Leu
705                 710                 715                 720

Lys Thr Asp Val Asn Lys Glu Phe Gln Met Gly Ala Ala Pro Thr Thr
                725                 730                 735

Ser Asp Val Ala Gly Leu Gln Asn Asp Pro Thr Thr Asn Val Ala Arg
            740                 745                 750

Pro Asn Pro Ala Tyr Gly Lys His Met Gln Asp Glu Trp Gln Ala Ser
            755                 760                 765

Leu Ala Leu Ser Tyr Arg Leu Asn Met Phe Thr Pro Tyr Ile Gly Val
770                 775                 780

Lys Trp Ser Arg Val Ser Phe Asp Ala Asp Thr Ile Arg Ile Ala Gln
785                 790                 795                 800

Pro Lys Leu Ala Glu Ala Ile Leu Asp Val Thr Thr Leu Asn Pro Thr
                805                 810                 815

Ile Ala Gly Lys Gly Thr Val Val Ala Ser Gly Ser Glu Asn Asp Leu
            820                 825                 830

Ala Asp Thr Met Gln Ile Val Ser Leu Gln Leu Asn
            835                 840

<210> SEQ ID NO 49
<211> LENGTH: 205

```
<212> TYPE: PRT
<213> ORGANISM: Chlamydia trachomatis

<400> SEQUENCE: 49

Asn Met Phe Thr Pro Tyr Ile Gly Val Lys Trp Ser Arg Ala Ser Phe
1               5                   10                  15

Asp Ala Asp Thr Ile Arg Ile Ala Gln Pro Lys Ser Ala Thr Ala Ile
            20                  25                  30

Phe Asp Thr Thr Thr Leu Asn Pro Thr Ile Ala Gly Ala Gly Asp Val
        35                  40                  45

Lys Thr Gly Ala Glu Gly Gln Leu Gly Asp Thr Met Gln Ile Val Ser
50                  55                  60

Leu Gln Leu Asn Asn Met Phe Thr Pro Tyr Ile Gly Val Lys Trp Ser
65                  70                  75                  80

Arg Ala Ser Phe Asp Ala Asp Thr Ile Arg Ile Ala Gln Pro Lys Ser
                85                  90                  95

Ala Thr Ala Ile Phe Asp Thr Thr Thr Leu Asn Pro Thr Ile Ala Gly
            100                 105                 110

Ala Gly Asp Val Lys Ala Ser Ala Glu Gly Gln Leu Gly Asp Thr Met
        115                 120                 125

Gln Ile Val Ser Leu Gln Leu Asn Asn Met Phe Thr Pro Tyr Ile Gly
    130                 135                 140

Val Lys Trp Ser Arg Ala Ser Phe Asp Ser Asp Thr Ile Arg Ile Ala
145                 150                 155                 160

Gln Pro Arg Leu Val Thr Pro Val Val Asp Ile Thr Thr Leu Asn Pro
                165                 170                 175

Thr Ile Ala Gly Ser Gly Ser Val Ala Gly Ala Asn Thr Glu Gly Gln
            180                 185                 190

Ile Ser Asp Thr Met Gln Ile Val Ser Leu Gln Leu Asn
        195                 200                 205

<210> SEQ ID NO 50
<211> LENGTH: 75
<212> TYPE: PRT
<213> ORGANISM: Chlamydia trachomatis

<400> SEQUENCE: 50

Met His His His His His His Asn Met Phe Thr Pro Tyr Ile Gly Val
1               5                   10                  15

Lys Trp Ser Arg Ala Ser Phe Asp Ala Asp Thr Ile Arg Ile Ala Gln
            20                  25                  30

Pro Lys Ser Ala Thr Ala Ile Phe Asp Thr Thr Thr Leu Asn Pro Thr
        35                  40                  45

Ile Ala Gly Ala Gly Asp Val Lys Ala Ser Ala Glu Gly Gln Leu Gly
    50                  55                  60

Asp Thr Met Gln Ile Val Ser Leu Gln Leu Asn
65                  70                  75

<210> SEQ ID NO 51
<211> LENGTH: 69
<212> TYPE: PRT
<213> ORGANISM: Chlamydia trachomatis

<400> SEQUENCE: 51

Asn Met Phe Thr Pro Tyr Ile Gly Val Lys Trp Ser Arg Ala Ser Phe
1               5                   10                  15

Asp Ser Asp Thr Ile Arg Ile Ala Gln Pro Arg Leu Val Thr Pro Val
```

```
            20                  25                  30
Val Asp Ile Thr Thr Leu Asn Pro Thr Ile Ala Gly Cys Gly Ser Val
            35                  40                  45

Ala Gly Ala Asn Thr Glu Gly Gln Ile Ser Asp Thr Met Gln Ile Val
        50                  55                  60

Ser Leu Gln Leu Asn
65

<210> SEQ ID NO 52
<211> LENGTH: 76
<212> TYPE: PRT
<213> ORGANISM: Chlamydia trachomatis

<400> SEQUENCE: 52

Met His His His His His His Asn Met Phe Thr Pro Tyr Ile Gly Val
1               5                   10                  15

Lys Trp Ser Arg Ala Ser Phe Asp Ser Asp Thr Ile Arg Ile Ala Gln
            20                  25                  30

Pro Arg Leu Val Thr Pro Val Val Asp Ile Thr Thr Leu Asn Pro Thr
        35                  40                  45

Ile Ala Gly Cys Gly Ser Val Ala Gly Ala Asn Thr Glu Gly Gln Ile
    50                  55                  60

Ser Asp Thr Met Gln Ile Val Ser Leu Gln Leu Asn
65                  70                  75

<210> SEQ ID NO 53
<211> LENGTH: 274
<212> TYPE: PRT
<213> ORGANISM: Chlamydia trachomatis

<400> SEQUENCE: 53

Asn Met Phe Thr Pro Tyr Ile Gly Val Lys Trp Ser Arg Ala Ser Phe
1               5                   10                  15

Asp Ala Asp Thr Ile Arg Ile Ala Gln Pro Lys Ser Ala Thr Ala Ile
            20                  25                  30

Phe Asp Thr Thr Thr Leu Asn Pro Thr Ile Ala Gly Ala Gly Asp Val
        35                  40                  45

Lys Thr Gly Ala Glu Gly Gln Leu Gly Asp Thr Met Gln Ile Val Ser
    50                  55                  60

Leu Gln Leu Asn Asn Met Phe Thr Pro Tyr Ile Gly Val Lys Trp Ser
65                  70                  75                  80

Arg Ala Ser Phe Asp Ala Asp Thr Ile Arg Ile Ala Gln Pro Lys Ser
            85                  90                  95

Ala Thr Ala Ile Phe Asp Thr Thr Thr Leu Asn Pro Thr Ile Ala Gly
            100                 105                 110

Ala Gly Asp Val Lys Ala Ser Ala Glu Gly Gln Leu Gly Asp Thr Met
        115                 120                 125

Gln Ile Val Ser Leu Gln Leu Asn Asn Met Phe Thr Pro Tyr Ile Gly
    130                 135                 140

Val Lys Trp Ser Arg Ala Ser Phe Asp Ser Asp Thr Ile Arg Ile Ala
145                 150                 155                 160

Gln Pro Arg Leu Val Thr Pro Val Val Asp Ile Thr Thr Leu Asn Pro
                165                 170                 175

Thr Ile Ala Gly Ser Gly Ser Val Ala Gly Ala Asn Thr Glu Gly Gln
            180                 185                 190

Ile Ser Asp Thr Met Gln Ile Val Ser Leu Gln Leu Asn Asn Met Phe
```

```
            195                 200                 205
Thr Pro Tyr Ile Gly Val Lys Trp Ser Arg Ala Ser Phe Asp Ser Asn
    210                 215                 220

Thr Ile Arg Ile Ala Gln Pro Lys Leu Ala Lys Pro Val Val Asp Ile
225                 230                 235                 240

Thr Thr Leu Asn Pro Thr Ile Ala Gly Ser Gly Ser Val Val Ala Ala
                245                 250                 255

Asn Ser Glu Gly Gln Ile Ser Asp Thr Met Gln Ile Val Ser Leu Gln
                260                 265                 270

Leu Asn

<210> SEQ ID NO 54
<211> LENGTH: 322
<212> TYPE: PRT
<213> ORGANISM: Chlamydia trachomatis

<400> SEQUENCE: 54

Glu Trp Gln Ala Ser Leu Ala Leu Ser Tyr Arg Leu Asn Met Phe Thr
1               5                   10                  15

Pro Tyr Ile Gly Val Lys Trp Ser Arg Ala Ser Phe Asp Ala Asp Thr
                20                  25                  30

Ile Arg Ile Ala Gln Pro Lys Ser Ala Thr Ala Ile Phe Asp Thr Thr
            35                  40                  45

Thr Leu Asn Pro Thr Ile Ala Gly Ala Gly Asp Val Lys Thr Gly Ala
        50                  55                  60

Glu Gly Gln Leu Gly Asp Thr Met Gln Ile Val Ser Leu Gln Leu Asn
65                  70                  75                  80

Glu Trp Gln Ala Ser Leu Ala Leu Ser Tyr Arg Leu Asn Met Phe Thr
                85                  90                  95

Pro Tyr Ile Gly Val Lys Trp Ser Arg Ala Ser Phe Asp Ala Asp Thr
                100                 105                 110

Ile Arg Ile Ala Gln Pro Lys Ser Ala Thr Ala Ile Phe Asp Thr Thr
            115                 120                 125

Thr Leu Asn Pro Thr Ile Ala Gly Ala Gly Asp Val Lys Ala Ser Ala
        130                 135                 140

Glu Gly Gln Leu Gly Asp Thr Met Gln Ile Val Ser Leu Gln Leu Asn
145                 150                 155                 160

Glu Trp Gln Ala Ser Leu Ser Leu Ser Tyr Arg Leu Asn Met Phe Thr
                165                 170                 175

Pro Tyr Ile Gly Val Lys Trp Ser Arg Ala Ser Phe Asp Ser Asp Thr
                180                 185                 190

Ile Arg Ile Ala Gln Pro Arg Leu Val Thr Pro Val Val Asp Ile Thr
            195                 200                 205

Thr Leu Asn Pro Thr Ile Ala Gly Ser Gly Ser Val Ala Gly Ala Asn
        210                 215                 220

Thr Glu Gly Gln Ile Ser Asp Thr Met Gln Ile Val Ser Leu Gln Leu
225                 230                 235                 240

Asn Glu Trp Gln Ala Ser Leu Ser Leu Ser Tyr Arg Leu Asn Met Phe
                245                 250                 255

Thr Pro Tyr Ile Gly Val Lys Trp Ser Arg Ala Ser Phe Asp Ser Asn
                260                 265                 270

Thr Ile Arg Ile Ala Gln Pro Lys Leu Ala Lys Pro Val Val Asp Ile
            275                 280                 285

Thr Thr Leu Asn Pro Thr Ile Ala Gly Ser Gly Ser Val Val Ala Ala
```

```
              290                 295                 300
Asn Ser Glu Gly Gln Ile Ser Asp Thr Met Gln Ile Val Ser Leu Gln
305                 310                 315                 320

Leu Asn

<210> SEQ ID NO 55
<211> LENGTH: 484
<212> TYPE: PRT
<213> ORGANISM: Chlamydia trachomatis

<400> SEQUENCE: 55

Glu Trp Gln Ala Ser Leu Ala Leu Ser Tyr Arg Leu Asn Met Phe Thr
1               5                  10                  15

Pro Tyr Ile Gly Val Lys Trp Ser Arg Ala Ser Phe Asp Ala Asp Thr
            20                  25                  30

Ile Arg Ile Ala Gln Pro Lys Ser Ala Thr Ala Ile Phe Asp Thr Thr
        35                  40                  45

Thr Leu Asn Pro Thr Ile Ala Gly Ala Gly Asp Val Lys Thr Gly Ala
    50                  55                  60

Glu Gly Gln Leu Gly Asp Thr Met Gln Ile Val Ser Leu Gln Leu Asn
65                  70                  75                  80

Glu Trp Gln Ala Ser Leu Ala Leu Ser Tyr Arg Leu Asn Met Phe Thr
                85                  90                  95

Pro Tyr Ile Gly Val Lys Trp Ser Arg Ala Ser Phe Asp Ala Asp Thr
            100                 105                 110

Ile Arg Ile Ala Gln Pro Lys Ser Ala Thr Ala Ile Phe Asp Thr Thr
        115                 120                 125

Thr Leu Asn Pro Thr Ile Ala Gly Ala Gly Asp Val Lys Ala Ser Ala
    130                 135                 140

Glu Gly Gln Leu Gly Asp Thr Met Gln Ile Val Ser Leu Gln Leu Asn
145                 150                 155                 160

Glu Trp Gln Ala Ser Leu Ser Leu Ser Tyr Arg Leu Asn Met Phe Thr
                165                 170                 175

Pro Tyr Ile Gly Val Lys Trp Ser Arg Ala Ser Phe Asp Ser Asp Thr
            180                 185                 190

Ile Arg Ile Ala Gln Pro Arg Leu Val Thr Pro Val Asp Ile Thr
        195                 200                 205

Thr Leu Asn Pro Thr Ile Ala Gly Ser Gly Ser Val Ala Gly Ala Asn
    210                 215                 220

Thr Glu Gly Gln Ile Ser Asp Thr Met Gln Ile Val Ser Leu Gln Leu
225                 230                 235                 240

Asn Glu Trp Gln Ala Ser Leu Ser Leu Ser Tyr Arg Leu Asn Met Phe
                245                 250                 255

Thr Pro Tyr Ile Gly Val Lys Trp Ser Arg Ala Ser Phe Asp Ser Asn
            260                 265                 270

Thr Ile Arg Ile Ala Gln Pro Lys Leu Ala Lys Pro Val Val Asp Ile
        275                 280                 285

Thr Thr Leu Asn Pro Thr Ile Ala Gly Ser Gly Ser Val Val Ala Ala
    290                 295                 300

Asn Ser Glu Gly Gln Ile Ser Asp Thr Met Gln Ile Val Ser Leu Gln
305                 310                 315                 320

Leu Asn Glu Trp Gln Ala Ser Leu Ala Leu Ser Tyr Arg Leu Asn Met
                325                 330                 335

Phe Thr Pro Tyr Ile Gly Val Lys Trp Ser Arg Val Ser Phe Asp Ala
```

```
                  340                 345                 350
Asp Thr Ile Arg Ile Ala Gln Pro Lys Leu Ala Glu Ala Ile Leu Asp
                355                 360                 365

Val Thr Thr Leu Asn Pro Thr Ile Ala Gly Lys Gly Thr Val Val Ala
        370                 375                 380

Ser Gly Ser Asp Asn Asp Leu Ala Asp Thr Met Gln Ile Val Ser Leu
385                 390                 395                 400

Gln Leu Asn Glu Trp Gln Ala Ser Leu Ala Leu Ser Tyr Arg Leu Asn
                405                 410                 415

Met Phe Thr Pro Tyr Ile Gly Val Lys Trp Ser Arg Val Ser Phe Asp
                420                 425                 430

Ala Asp Thr Ile Arg Ile Ala Gln Pro Lys Leu Ala Glu Ala Ile Leu
                435                 440                 445

Asp Val Thr Thr Leu Asn Pro Thr Ile Ala Gly Lys Gly Thr Val Val
        450                 455                 460

Ala Ser Gly Ser Glu Asn Asp Leu Ala Asp Thr Met Gln Ile Val Ser
465                 470                 475                 480

Leu Gln Leu Asn

<210> SEQ ID NO 56
<211> LENGTH: 276
<212> TYPE: PRT
<213> ORGANISM: Chlamydia trachomatis

<400> SEQUENCE: 56

Asn Met Phe Thr Pro Tyr Ile Gly Val Lys Trp Ser Arg Ala Ser Phe
1               5                   10                  15

Asp Ser Asp Thr Ile Arg Ile Ala Gln Pro Arg Leu Val Thr Pro Val
                20                  25                  30

Val Asp Ile Thr Thr Leu Asn Pro Thr Ile Ala Gly Ser Gly Ser Val
        35                  40                  45

Ala Gly Ala Asn Thr Glu Gly Gln Ile Ser Asp Thr Met Gln Ile Val
    50                  55                  60

Ser Leu Gln Leu Asn Asn Met Phe Thr Pro Tyr Ile Gly Val Lys Trp
65                  70                  75                  80

Ser Arg Ala Ser Phe Asp Ser Asp Thr Ile Arg Ile Ala Gln Pro Arg
                85                  90                  95

Leu Val Thr Pro Val Val Asp Ile Thr Thr Leu Asn Pro Thr Ile Ala
                100                 105                 110

Gly Ser Gly Ser Val Ala Gly Ala Asn Thr Glu Gly Gln Ile Ser Asp
                115                 120                 125

Thr Met Gln Ile Val Ser Leu Gln Leu Asn Asn Met Phe Thr Pro Tyr
130                 135                 140

Ile Gly Val Lys Trp Ser Arg Ala Ser Phe Asp Ser Asp Thr Ile Arg
145                 150                 155                 160

Ile Ala Gln Pro Arg Leu Val Thr Pro Val Val Asp Ile Thr Thr Leu
                165                 170                 175

Asn Pro Thr Ile Ala Gly Ser Gly Ser Val Ala Gly Ala Asn Thr Glu
                180                 185                 190

Gly Gln Ile Ser Asp Thr Met Gln Ile Val Ser Leu Gln Leu Asn Asn
                195                 200                 205

Met Phe Thr Pro Tyr Ile Gly Val Lys Trp Ser Arg Ala Ser Phe Asp
                210                 215                 220

Ser Asp Thr Ile Arg Ile Ala Gln Pro Arg Leu Val Thr Pro Val Val
```

```
                    225                 230                 235                 240
Asp Ile Thr Thr Leu Asn Pro Thr Ile Ala Gly Ser Gly Ser Val Ala
                245                 250                 255

Gly Ala Asn Thr Glu Gly Gln Ile Ser Asp Thr Met Gln Ile Val Ser
            260                 265                 270

Leu Gln Leu Asn
        275

<210> SEQ ID NO 57
<211> LENGTH: 544
<212> TYPE: PRT
<213> ORGANISM: Chlamydia trachomatis

<400> SEQUENCE: 57

Asn Met Phe Thr Pro Tyr Ile Gly Val Lys Trp Ser Arg Ala Ser Phe
1               5                   10                  15

Asp Ala Asp Thr Ile Arg Ile Ala Gln Pro Lys Ser Ala Thr Ala Ile
            20                  25                  30

Phe Asp Thr Thr Thr Leu Asn Pro Thr Ile Ala Gly Ala Gly Asp Val
        35                  40                  45

Lys Ala Ser Ala Glu Gly Gln Leu Gly Asp Thr Met Gln Ile Val Ser
50                  55                  60

Leu Gln Leu Asn Asn Met Phe Thr Pro Tyr Ile Gly Val Lys Trp Ser
65                  70                  75                  80

Arg Ala Ser Phe Asp Ala Asp Thr Ile Arg Ile Ala Gln Pro Lys Ser
                85                  90                  95

Ala Thr Ala Ile Phe Asp Thr Thr Thr Leu Asn Pro Thr Ile Ala Gly
            100                 105                 110

Ala Gly Asp Val Lys Ala Ser Ala Glu Gly Gln Leu Gly Asp Thr Met
        115                 120                 125

Gln Ile Val Ser Leu Gln Leu Asn Asn Met Phe Thr Pro Tyr Ile Gly
    130                 135                 140

Val Lys Trp Ser Arg Ala Ser Phe Asp Ala Asp Thr Ile Arg Ile Ala
145                 150                 155                 160

Gln Pro Lys Ser Ala Thr Ala Ile Phe Asp Thr Thr Thr Leu Asn Pro
                165                 170                 175

Thr Ile Ala Gly Ala Gly Asp Val Lys Ala Ser Ala Glu Gly Gln Leu
            180                 185                 190

Gly Asp Thr Met Gln Ile Val Ser Leu Gln Leu Asn Asn Met Phe Thr
        195                 200                 205

Pro Tyr Ile Gly Val Lys Trp Ser Arg Ala Ser Phe Asp Ala Asp Thr
    210                 215                 220

Ile Arg Ile Ala Gln Pro Lys Ser Ala Thr Ala Ile Phe Asp Thr Thr
225                 230                 235                 240

Thr Leu Asn Pro Thr Ile Ala Gly Ala Gly Asp Val Lys Ala Ser Ala
                245                 250                 255

Glu Gly Gln Leu Gly Asp Thr Met Gln Ile Val Ser Leu Gln Leu Asn
            260                 265                 270

Asn Met Phe Thr Pro Tyr Ile Gly Val Lys Trp Ser Arg Ala Ser Phe
        275                 280                 285

Asp Ala Asp Thr Ile Arg Ile Ala Gln Pro Lys Ser Ala Thr Ala Ile
    290                 295                 300

Phe Asp Thr Thr Thr Leu Asn Pro Thr Ile Ala Gly Ala Gly Asp Val
305                 310                 315                 320
```

```
Lys Ala Ser Ala Glu Gly Gln Leu Gly Asp Thr Met Gln Ile Val Ser
                325                 330                 335

Leu Gln Leu Asn Asn Met Phe Thr Pro Tyr Ile Gly Val Lys Trp Ser
            340                 345                 350

Arg Ala Ser Phe Asp Ala Asp Thr Ile Arg Ile Ala Gln Pro Lys Ser
        355                 360                 365

Ala Thr Ala Ile Phe Asp Thr Thr Leu Asn Pro Thr Ile Ala Gly
    370                 375                 380

Ala Gly Asp Val Lys Ala Ser Ala Glu Gly Gln Leu Gly Asp Thr Met
385                 390                 395                 400

Gln Ile Val Ser Leu Gln Leu Asn Asn Met Phe Thr Pro Tyr Ile Gly
                405                 410                 415

Val Lys Trp Ser Arg Ala Ser Phe Asp Ala Asp Thr Ile Arg Ile Ala
            420                 425                 430

Gln Pro Lys Ser Ala Thr Ala Ile Phe Asp Thr Thr Leu Asn Pro
        435                 440                 445

Thr Ile Ala Gly Ala Gly Asp Val Lys Ala Ser Ala Glu Gly Gln Leu
    450                 455                 460

Gly Asp Thr Met Gln Ile Val Ser Leu Gln Leu Asn Asn Met Phe Thr
465                 470                 475                 480

Pro Tyr Ile Gly Val Lys Trp Ser Arg Ala Ser Phe Asp Ala Asp Thr
                485                 490                 495

Ile Arg Ile Ala Gln Pro Lys Ser Ala Thr Ala Ile Phe Asp Thr Thr
            500                 505                 510

Thr Leu Asn Pro Thr Ile Ala Gly Ala Gly Asp Val Lys Ala Ser Ala
        515                 520                 525

Glu Gly Gln Leu Gly Asp Thr Met Gln Ile Val Ser Leu Gln Leu Asn
    530                 535                 540

<210> SEQ ID NO 58
<211> LENGTH: 272
<212> TYPE: PRT
<213> ORGANISM: Chlamydia trachomatis

<400> SEQUENCE: 58

Asn Met Phe Thr Pro Tyr Ile Gly Val Lys Trp Ser Arg Ala Ser Phe
1               5                   10                  15

Asp Ala Asp Thr Ile Arg Ile Ala Gln Pro Lys Ser Ala Thr Ala Ile
            20                  25                  30

Phe Asp Thr Thr Thr Leu Asn Pro Thr Ile Ala Gly Ala Gly Asp Val
        35                  40                  45

Lys Ala Ser Ala Glu Gly Gln Leu Gly Asp Thr Met Gln Ile Val Ser
    50                  55                  60

Leu Gln Leu Asn Asn Met Phe Thr Pro Tyr Ile Gly Val Lys Trp Ser
65                  70                  75                  80

Arg Ala Ser Phe Asp Ala Asp Thr Ile Arg Ile Ala Gln Pro Lys Ser
                85                  90                  95

Ala Thr Ala Ile Phe Asp Thr Thr Leu Asn Pro Thr Ile Ala Gly
            100                 105                 110

Ala Gly Asp Val Lys Ala Ser Ala Glu Gly Gln Leu Gly Asp Thr Met
        115                 120                 125

Gln Ile Val Ser Leu Gln Leu Asn Asn Met Phe Thr Pro Tyr Ile Gly
    130                 135                 140

Val Lys Trp Ser Arg Ala Ser Phe Asp Ala Asp Thr Ile Arg Ile Ala
145                 150                 155                 160
```

```
Gln Pro Lys Ser Ala Thr Ala Ile Phe Asp Thr Thr Leu Asn Pro
                165                 170                 175

Thr Ile Ala Gly Ala Gly Asp Val Lys Ala Ser Ala Glu Gly Gln Leu
            180                 185                 190

Gly Asp Thr Met Gln Ile Val Ser Leu Gln Leu Asn Asn Met Phe Thr
            195                 200                 205

Pro Tyr Ile Gly Val Lys Trp Ser Arg Ala Ser Phe Asp Ala Asp Thr
        210                 215                 220

Ile Arg Ile Ala Gln Pro Lys Ser Ala Thr Ala Ile Phe Asp Thr Thr
225                 230                 235                 240

Thr Leu Asn Pro Thr Ile Ala Gly Ala Gly Asp Val Lys Ala Ser Ala
            245                 250                 255

Glu Gly Gln Leu Gly Asp Thr Met Gln Ile Val Ser Leu Gln Leu Asn
        260                 265                 270
```

<210> SEQ ID NO 59
<211> LENGTH: 276
<212> TYPE: PRT
<213> ORGANISM: Chlamydia trachomatis

<400> SEQUENCE: 59

```
Asn Met Phe Thr Pro Tyr Ile Gly Val Lys Trp Ser Arg Ala Ser Phe
1               5                   10                  15

Asp Ser Asp Thr Ile Arg Ile Ala Gln Pro Arg Leu Val Thr Pro Val
            20                  25                  30

Val Asp Ile Thr Thr Leu Asn Pro Thr Ile Ala Gly Cys Gly Ser Val
        35                  40                  45

Ala Gly Ala Asn Thr Glu Gly Gln Ile Ser Asp Thr Met Gln Ile Val
    50                  55                  60

Ser Leu Gln Leu Asn Asn Met Phe Thr Pro Tyr Ile Gly Val Lys Trp
65                  70                  75                  80

Ser Arg Ala Ser Phe Asp Ser Asp Thr Ile Arg Ile Ala Gln Pro Arg
                85                  90                  95

Leu Val Thr Pro Val Val Asp Ile Thr Thr Leu Asn Pro Thr Ile Ala
            100                 105                 110

Gly Cys Gly Ser Val Ala Gly Ala Asn Thr Glu Gly Gln Ile Ser Asp
        115                 120                 125

Thr Met Gln Ile Val Ser Leu Gln Leu Asn Asn Met Phe Thr Pro Tyr
    130                 135                 140

Ile Gly Val Lys Trp Ser Arg Ala Ser Phe Asp Ser Asp Thr Ile Arg
145                 150                 155                 160

Ile Ala Gln Pro Arg Leu Val Thr Pro Val Val Asp Ile Thr Thr Leu
                165                 170                 175

Asn Pro Thr Ile Ala Gly Cys Gly Ser Val Ala Gly Ala Asn Thr Glu
            180                 185                 190

Gly Gln Ile Ser Asp Thr Met Gln Ile Val Ser Leu Gln Leu Asn Asn
        195                 200                 205

Met Phe Thr Pro Tyr Ile Gly Val Lys Trp Ser Arg Ala Ser Phe Asp
    210                 215                 220

Ser Asp Thr Ile Arg Ile Ala Gln Pro Arg Leu Val Thr Pro Val Val
225                 230                 235                 240

Asp Ile Thr Thr Leu Asn Pro Thr Ile Ala Gly Cys Gly Ser Val Ala
                245                 250                 255

Gly Ala Asn Thr Glu Gly Gln Ile Ser Asp Thr Met Gln Ile Val Ser
```

```
                            260                 265                 270

Leu Gln Leu Asn
        275

<210> SEQ ID NO 60
<211> LENGTH: 785
<212> TYPE: PRT
<213> ORGANISM: Chlamydia trachomatis

<400> SEQUENCE: 60

Ser Arg Gln Asn Ala Glu Glu Asn Leu Lys Asn Phe Ala Lys Glu Leu
1               5                   10                  15

Lys Leu Pro Asp Val Ala Phe Asp Gln Asn Asn Thr Cys Ile Leu Phe
            20                  25                  30

Val Asp Gly Glu Phe Ser Leu His Leu Thr Tyr Glu Glu His Ser Asp
        35                  40                  45

Arg Leu Tyr Val Tyr Ala Pro Leu Leu Asp Gly Leu Pro Asp Asn Pro
    50                  55                  60

Gln Arg Arg Leu Ala Leu Tyr Glu Lys Leu Leu Glu Gly Ser Met Leu
65                  70                  75                  80

Gly Gly Gln Met Ala Gly Gly Val Gly Val Ala Thr Lys Glu Gln
                85                  90                  95

Leu Ile Leu Met His Cys Val Leu Asp Met Lys Tyr Ala Glu Thr Asn
            100                 105                 110

Leu Leu Lys Ala Phe Ala Gln Leu Phe Ile Glu Thr Val Val Lys Trp
        115                 120                 125

Arg Thr Val Cys Ser Asp Ile Ser Ala Gly Arg Glu Pro Thr Val Asp
    130                 135                 140

Thr Met Pro Gln Met Pro Gln Gly Gly Gly Gly Ile Gln Pro Pro
145                 150                 155                 160

Pro Ala Gly Ile Arg Ala Thr Val Lys Ala Ile Val Glu Ser Thr Pro
                165                 170                 175

Glu Ala Pro Glu Glu Ile Pro Pro Val Glu Gly Glu Ser Thr Ala
            180                 185                 190

Thr Glu Asp Pro Asn Ser Asn Thr Glu Gly Ser Ser Ala Asn Thr Asn
        195                 200                 205

Leu Glu Gly Ser Gln Gly Asp Thr Ala Asp Thr Gly Thr Gly Asp Val
    210                 215                 220

Asn Asn Glu Ser Gln Asp Thr Ser Asp Thr Gly Asn Ala Glu Ser Glu
225                 230                 235                 240

Glu Gln Leu Gln Asp Ser Thr Gln Ser Asn Glu Asn Thr Leu Pro
                245                 250                 255

Asn Ser Asn Ile Asp Gln Ser Asn Glu Asn Thr Asp Glu Ser Ser Asp
            260                 265                 270

Ser His Thr Glu Glu Ile Thr Asp Glu Ser Val Ser Ser Ser Ser Glu
        275                 280                 285

Ser Gly Ser Ser Thr Pro Gln Asp Gly Gly Ala Ala Ser Ser Gly Ala
    290                 295                 300

Pro Ser Gly Asp Gln Ser Ile Ser Ala Asn Ala Cys Leu Ala Lys Ser
305                 310                 315                 320

Tyr Ala Ala Ser Thr Asp Ser Ser Pro Val Ser Asn Ser Ser Gly Ser
                325                 330                 335

Glu Glu Pro Val Thr Ser Ser Ser Asp Ser Asp Val Thr Ala Ser Ser
            340                 345                 350
```

```
Asp Asn Pro Asp Ser Ser Ser Gly Asp Ser Ala Gly Asp Ser Glu
        355                 360                 365

Glu Pro Thr Glu Pro Glu Ala Gly Ser Thr Thr Glu Thr Leu Thr Leu
    370                 375                 380

Ile Gly Gly Gly Ala Ile Tyr Gly Glu Thr Val Lys Ile Glu Asn Phe
385                 390                 395                 400

Ser Gly Ala Ile Ser Met Arg Val Gly Tyr Tyr Gly Asp Phe Val Phe
                405                 410                 415

Asp Arg Val Leu Lys Thr Asp Val Asn Lys Glu Phe Gln Met Gly Ala
            420                 425                 430

Lys Pro Thr Thr Asp Thr Gly Asn Ser Ala Ala Pro Ser Thr Leu Thr
        435                 440                 445

Ala Arg Glu Asn Pro Ala Tyr Gly Arg His Met Gln Asp Asn Met Phe
    450                 455                 460

Thr Pro Tyr Ile Gly Val Lys Trp Ser Arg Ala Ser Phe Asp Ala Asp
465                 470                 475                 480

Thr Ile Arg Ile Ala Gln Pro Lys Ser Ala Thr Ala Ile Phe Asp Thr
                485                 490                 495

Thr Thr Leu Asn Pro Thr Ile Ala Gly Ala Gly Asp Val Lys Thr Gly
            500                 505                 510

Ala Glu Gly Gln Leu Gly Asp Thr Met Gln Ile Val Ser Leu Gln Leu
        515                 520                 525

Asn Ala Ile Ser Met Arg Met Gly Tyr Tyr Gly Asp Phe Val Phe Asp
    530                 535                 540

Arg Val Leu Lys Thr Asp Val Asn Lys Glu Phe Gln Met Gly Asp Lys
545                 550                 555                 560

Pro Thr Ser Thr Thr Gly Asn Ala Thr Ala Pro Thr Thr Leu Thr Ala
                565                 570                 575

Arg Glu Asn Pro Ala Tyr Gly Arg His Met Gln Asp Asn Met Phe Thr
            580                 585                 590

Pro Tyr Ile Gly Val Lys Trp Ser Arg Ala Ser Phe Asp Ala Asp Thr
        595                 600                 605

Ile Arg Ile Ala Gln Pro Lys Ser Ala Thr Ala Ile Phe Asp Thr Thr
    610                 615                 620

Thr Leu Asn Pro Thr Ile Ala Gly Ala Gly Asp Val Lys Ala Ser Ala
625                 630                 635                 640

Glu Gly Gln Leu Gly Asp Thr Met Gln Ile Val Ser Leu Gln Leu Asn
                645                 650                 655

Ala Ile Ser Met Arg Met Gly Tyr Tyr Gly Asp Phe Val Phe Asp Arg
            660                 665                 670

Val Leu Lys Thr Asp Val Asn Lys Glu Phe Glu Met Gly Glu Ala Leu
        675                 680                 685

Ala Gly Ala Ser Gly Asn Thr Thr Ser Thr Leu Ser Lys Leu Val Glu
    690                 695                 700

Arg Thr Asn Pro Ala Tyr Gly Lys His Met Gln Asp Asn Met Phe Thr
705                 710                 715                 720

Pro Tyr Ile Gly Val Lys Trp Ser Arg Ala Ser Phe Asp Ser Asp Thr
                725                 730                 735

Ile Arg Ile Ala Gln Pro Arg Leu Val Thr Pro Val Val Asp Ile Thr
            740                 745                 750

Thr Leu Asn Pro Thr Ile Ala Gly Ser Gly Ser Val Ala Gly Ala Asn
        755                 760                 765

Thr Glu Gly Gln Ile Ser Asp Thr Met Gln Ile Val Ser Leu Gln Leu
```

```
                        770                 775                 780
Asn
785
```

<210> SEQ ID NO 61
<211> LENGTH: 740
<212> TYPE: PRT
<213> ORGANISM: Chlamydia trachomatis

<400> SEQUENCE: 61

```
Ser Arg Gln Asn Ala Glu Glu Asn Leu Lys Asn Phe Ala Lys Glu Leu
1               5                   10                  15

Lys Leu Pro Asp Val Ala Phe Asp Gln Asn Asn Thr Cys Ile Leu Phe
            20                  25                  30

Val Asp Gly Glu Phe Ser Leu His Leu Thr Tyr Glu Glu His Ser Asp
        35                  40                  45

Arg Leu Tyr Val Tyr Ala Pro Leu Leu Asp Gly Leu Pro Asp Asn Pro
    50                  55                  60

Gln Arg Arg Leu Ala Leu Tyr Glu Lys Leu Leu Glu Gly Ser Met Leu
65                  70                  75                  80

Gly Gly Gln Met Ala Gly Gly Val Gly Val Ala Thr Lys Glu Gln
                85                  90                  95

Leu Ile Leu Met His Cys Val Leu Asp Met Lys Tyr Ala Glu Thr Asn
            100                 105                 110

Leu Leu Lys Ala Phe Ala Gln Leu Phe Ile Glu Thr Val Val Lys Trp
        115                 120                 125

Arg Thr Val Cys Ser Asp Ile Ser Ala Gly Arg Glu Pro Thr Val Asp
    130                 135                 140

Thr Met Pro Gln Met Pro Gln Gly Gly Gly Gly Ile Gln Pro Pro
145                 150                 155                 160

Pro Ala Gly Ile Arg Ala Thr Val Lys Ala Ile Val Glu Ser Thr Pro
                165                 170                 175

Glu Ala Pro Glu Glu Ile Pro Pro Val Glu Gly Glu Ser Thr Ala
            180                 185                 190

Thr Glu Asp Pro Asn Ser Asn Thr Glu Gly Ser Ser Ala Asn Thr Asn
        195                 200                 205

Leu Glu Gly Ser Gln Gly Asp Thr Ala Asp Thr Gly Thr Gly Asp Val
    210                 215                 220

Asn Asn Glu Ser Gln Asp Thr Ser Asp Thr Gly Asn Ala Glu Ser Glu
225                 230                 235                 240

Glu Gln Leu Gln Asp Ser Thr Gln Ser Asn Glu Asn Thr Leu Pro
                245                 250                 255

Asn Ser Asn Ile Asp Gln Ser Asn Glu Asn Thr Asp Glu Ser Ser Asp
            260                 265                 270

Ser His Thr Glu Glu Ile Thr Asp Glu Ser Val Ser Ser Ser Ser Glu
        275                 280                 285

Ser Gly Ser Ser Thr Pro Gln Asp Gly Gly Ala Ala Ser Ser Gly Ala
    290                 295                 300

Pro Ser Gly Asp Gln Ser Ile Ser Ala Asn Ala Cys Leu Ala Lys Ser
305                 310                 315                 320

Tyr Ala Ala Ser Thr Asp Ser Ser Pro Val Ser Asn Ser Ser Gly Ser
                325                 330                 335

Glu Glu Pro Val Thr Ser Ser Ser Asp Ser Asp Val Thr Ala Ser Ser
            340                 345                 350
```

Asp Asn Pro Asp Ser Ser Ser Gly Asp Ser Ala Gly Asp Ser Glu
            355                 360                 365

Glu Pro Thr Glu Pro Glu Ala Gly Ser Thr Thr Glu Thr Leu Thr Leu
    370                 375                 380

Ile Gly Gly Gly Ala Ile Tyr Gly Glu Thr Val Lys Ile Glu Asn Phe
385                 390                 395                 400

Ser Gly Asp Ala Ile Ser Met Arg Val Gly Tyr Tyr Gly Asp Phe Val
                405                 410                 415

Phe Asp Arg Val Leu Lys Thr Asp Val Asn Lys Glu Phe Gln Met Gly
            420                 425                 430

Ala Lys Pro Thr Thr Asp Thr Gly Asn Ser Ala Ala Pro Ser Thr Leu
        435                 440                 445

Thr Ala Arg Glu Asn Pro Ala Tyr Gly Arg His Met Gln Asp Ala Glu
    450                 455                 460

Met Phe Thr Asn Ala Ala Ser Met Ala Leu Asn Ile Trp Asp Arg Phe
465                 470                 475                 480

Asp Val Phe Ser Thr Leu Gly Ala Thr Ser Gly Tyr Leu Lys Gly Asn
                485                 490                 495

Ser Ala Ser Phe Asn Leu Val Gly Leu Phe Gly Asp Asn Glu Asn Gln
            500                 505                 510

Lys Thr Val Lys Ala Glu Ser Val Pro Asn Met Ser Phe Asp Gln Ser
        515                 520                 525

Val Val Glu Leu Tyr Thr Asp Thr Thr Phe Ala Trp Ser Val Gly Ala
    530                 535                 540

Arg Ala Ala Leu Trp Glu Ser Gly Ser Ala Thr Leu Gly Ala Ser Phe
545                 550                 555                 560

Gln Tyr Ala Gln Ser Lys Pro Lys Val Glu Glu Leu Asn Val Leu Ser
                565                 570                 575

Asn Ala Ala Glu Phe Thr Ile Asn Lys Pro Lys Gly Tyr Val Gly Lys
            580                 585                 590

Glu Phe Pro Leu Asp Leu Thr Ala Gly Thr Asp Ala Ala Thr Gly Thr
        595                 600                 605

Lys Asp Ala Ser Ile Asp Tyr His Glu Trp Gln Ala Ser Leu Ala Leu
    610                 615                 620

Ser Tyr Arg Leu Asn Met Phe Thr Pro Tyr Ile Gly Val Lys Trp Ser
625                 630                 635                 640

Arg Ala Ser Phe Asp Ala Asp Thr Ile Arg Ile Ala Gln Pro Lys Ser
                645                 650                 655

Ala Thr Ala Ile Phe Asp Thr Thr Thr Leu Asn Pro Thr Ile Ala Gly
            660                 665                 670

Ala Gly Asp Val Lys Thr Gly Ala Glu Gly Gln Leu Gly Asp Thr Met
        675                 680                 685

Gln Ile Val Ser Leu Gln Leu Asn Lys Met Lys Ser Arg Lys Ser Ser
    690                 695                 700

Gly Ile Ala Val Gly Thr Thr Ile Val Asp Ala Asp Lys Tyr Ala Val
705                 710                 715                 720

Thr Val Glu Thr Arg Leu Ile Asp Glu Arg Ala Ala His Val Asn Ala
                725                 730                 735

Gln Phe Arg Phe
            740

<210> SEQ ID NO 62
<211> LENGTH: 294
<212> TYPE: PRT

<213> ORGANISM: Chlamydia trachomatis

<400> SEQUENCE: 62

Asp Ala Ile Ser Met Arg Val Gly Tyr Tyr Gly Asp Phe Val Phe Asp
1 5 10 15

Arg Val Leu Lys Thr Asp Val Asn Lys Glu Phe Gln Met Gly Ala Lys
20 25 30

Pro Thr Thr Asp Thr Gly Asn Ser Ala Ala Pro Ser Thr Leu Thr Ala
35 40 45

Arg Glu Asn Pro Ala Tyr Gly Arg His Met Gln Asp Ala Glu Met Phe
50 55 60

Thr Asn Ala Ala Cys Met Ala Leu Asn Ile Trp Asp Arg Phe Asp Val
65 70 75 80

Phe Cys Thr Leu Gly Ala Thr Ser Gly Tyr Leu Lys Gly Asn Ser Ala
85 90 95

Ser Phe Asn Leu Val Gly Leu Phe Gly Asp Asn Glu Asn Gln Lys Thr
100 105 110

Val Lys Ala Glu Ser Val Pro Asn Met Ser Phe Asp Gln Ser Val Val
115 120 125

Glu Leu Tyr Thr Asp Thr Thr Phe Ala Trp Ser Val Gly Ala Arg Ala
130 135 140

Ala Leu Trp Glu Cys Gly Cys Ala Thr Leu Gly Ala Ser Phe Gln Tyr
145 150 155 160

Ala Gln Ser Lys Pro Lys Val Glu Glu Leu Asn Val Leu Cys Asn Ala
165 170 175

Ala Glu Phe Thr Ile Asn Lys Pro Lys Gly Tyr Val Gly Lys Glu Phe
180 185 190

Pro Leu Asp Leu Thr Ala Gly Thr Asp Ala Ala Thr Gly Thr Lys Asp
195 200 205

Ala Ser Ile Asp Tyr His Glu Trp Gln Ala Ser Leu Ala Leu Ser Tyr
210 215 220

Arg Leu Asn Met Phe Thr Pro Tyr Ile Gly Val Lys Trp Ser Arg Ala
225 230 235 240

Ser Phe Asp Ala Asp Thr Ile Arg Ile Ala Gln Pro Lys Ser Ala Thr
245 250 255

Ala Ile Phe Asp Thr Thr Thr Leu Asn Pro Thr Ile Ala Gly Ala Gly
260 265 270

Asp Val Lys Thr Gly Ala Glu Gly Gln Leu Gly Asp Thr Met Gln Ile
275 280 285

Val Ser Leu Gln Leu Asn
290

<210> SEQ ID NO 63
<211> LENGTH: 294
<212> TYPE: PRT
<213> ORGANISM: Chlamydia trachomatis

<400> SEQUENCE: 63

Asp Ala Ile Ser Met Arg Val Gly Tyr Tyr Gly Asp Phe Val Phe Asp
1 5 10 15

Arg Val Leu Lys Thr Asp Val Asn Lys Glu Phe Gln Met Gly Ala Lys
20 25 30

Pro Thr Thr Asp Thr Gly Asn Ser Ala Ala Pro Ser Thr Leu Thr Ala
35 40 45

Arg Glu Asn Pro Ala Tyr Gly Arg His Met Gln Asp Ala Glu Met Phe

```
            50                  55                  60
Thr Asn Ala Ala Ser Met Ala Leu Asn Ile Trp Asp Arg Phe Asp Val
 65                  70                  75                  80

Phe Ser Thr Leu Gly Ala Thr Ser Gly Tyr Leu Lys Gly Asn Ser Ala
                     85                  90                  95

Ser Phe Asn Leu Val Gly Leu Phe Gly Asp Asn Glu Asn Gln Lys Thr
                    100                 105                 110

Val Lys Ala Glu Ser Val Pro Asn Met Ser Phe Asp Gln Ser Val Val
                115                 120                 125

Glu Leu Tyr Thr Asp Thr Thr Phe Ala Trp Ser Val Gly Ala Arg Ala
            130                 135                 140

Ala Leu Trp Glu Ser Gly Ser Ala Thr Leu Gly Ala Ser Phe Gln Tyr
145                 150                 155                 160

Ala Gln Ser Lys Pro Lys Val Glu Glu Leu Asn Val Leu Ser Asn Ala
                165                 170                 175

Ala Glu Phe Thr Ile Asn Lys Pro Lys Gly Tyr Val Gly Lys Glu Phe
            180                 185                 190

Pro Leu Asp Leu Thr Ala Gly Thr Asp Ala Ala Thr Gly Thr Lys Asp
        195                 200                 205

Ala Ser Ile Asp Tyr His Glu Trp Gln Ala Ser Leu Ala Leu Ser Tyr
    210                 215                 220

Arg Leu Asn Met Phe Thr Pro Tyr Ile Gly Val Lys Trp Ser Arg Ala
225                 230                 235                 240

Ser Phe Asp Ala Asp Thr Ile Arg Ile Ala Gln Pro Lys Ser Ala Thr
                245                 250                 255

Ala Ile Phe Asp Thr Thr Thr Leu Asn Pro Thr Ile Ala Gly Ala Gly
            260                 265                 270

Asp Val Lys Thr Gly Ala Glu Gly Gln Leu Gly Asp Thr Met Gln Ile
        275                 280                 285

Val Ser Leu Gln Leu Asn
    290
```

<210> SEQ ID NO 64
<211> LENGTH: 500
<212> TYPE: PRT
<213> ORGANISM: Chlamydia trachomatis

<400> SEQUENCE: 64

```
Asp Ala Ile Ser Met Arg Val Gly Tyr Tyr Gly Asp Phe Val Phe Asp
  1               5                  10                  15

Arg Val Leu Lys Thr Asp Val Asn Lys Glu Phe Gln Met Gly Ala Lys
                 20                  25                  30

Pro Thr Thr Asp Thr Gly Asn Ser Ala Ala Pro Ser Thr Leu Thr Ala
             35                  40                  45

Arg Glu Asn Pro Ala Tyr Gly Arg His Met Gln Asp Ala Glu Met Phe
     50                  55                  60

Thr Asn Ala Ala Ser Met Ala Leu Asn Ile Trp Asp Arg Phe Asp Val
 65                  70                  75                  80

Phe Ser Thr Leu Gly Ala Thr Ser Gly Tyr Leu Lys Gly Asn Ser Ala
                     85                  90                  95

Ser Phe Asn Leu Val Gly Leu Phe Gly Asp Asn Glu Asn Gln Lys Thr
                    100                 105                 110

Val Lys Ala Glu Ser Val Pro Asn Met Ser Phe Asp Gln Ser Val Val
                115                 120                 125
```

```
Glu Leu Tyr Thr Asp Thr Thr Phe Ala Trp Ser Val Gly Ala Arg Ala
            130                 135                 140

Ala Leu Trp Glu Ser Gly Ser Ala Thr Leu Gly Ala Ser Phe Gln Tyr
145                 150                 155                 160

Ala Gln Ser Lys Pro Lys Val Glu Leu Asn Val Leu Ser Asn Ala
                165                 170                 175

Ala Glu Phe Thr Ile Asn Lys Pro Lys Gly Tyr Val Gly Lys Glu Phe
            180                 185                 190

Pro Leu Asp Leu Thr Ala Gly Thr Asp Ala Ala Thr Gly Thr Lys Asp
            195                 200                 205

Ala Ser Ile Asp Tyr His Glu Trp Gln Ala Ser Leu Ala Leu Ser Tyr
        210                 215                 220

Arg Leu Asn Met Phe Thr Pro Tyr Ile Gly Val Lys Trp Ser Arg Ala
225                 230                 235                 240

Ser Phe Asp Ala Asp Thr Ile Arg Ile Ala Gln Pro Lys Ser Ala Thr
                245                 250                 255

Ala Ile Phe Asp Thr Thr Thr Leu Asn Pro Thr Ile Ala Gly Ala Gly
            260                 265                 270

Asp Val Lys Thr Gly Ala Glu Gly Gln Leu Gly Asp Thr Met Gln Ile
            275                 280                 285

Val Ser Leu Gln Leu Asn Asn Met Phe Thr Pro Tyr Ile Gly Val Lys
290                 295                 300

Trp Ser Arg Ala Ser Phe Asp Ala Asp Thr Ile Arg Ile Ala Gln Pro
305                 310                 315                 320

Lys Ser Ala Thr Ala Ile Phe Asp Thr Thr Thr Leu Asn Pro Thr Ile
                325                 330                 335

Ala Gly Ala Gly Asp Val Lys Ala Ser Ala Glu Gly Gln Leu Gly Asp
            340                 345                 350

Thr Met Gln Ile Val Ser Leu Gln Leu Asn Asn Met Phe Thr Pro Tyr
            355                 360                 365

Ile Gly Val Lys Trp Ser Arg Ala Ser Phe Asp Ser Asp Thr Ile Arg
        370                 375                 380

Ile Ala Gln Pro Arg Leu Val Thr Pro Val Val Asp Ile Thr Thr Leu
385                 390                 395                 400

Asn Pro Thr Ile Ala Gly Ser Gly Ser Val Ala Gly Ala Asn Thr Glu
                405                 410                 415

Gly Gln Ile Ser Asp Thr Met Gln Ile Val Ser Leu Gln Leu Asn Asn
            420                 425                 430

Met Phe Thr Pro Tyr Ile Gly Val Lys Trp Ser Arg Ala Ser Phe Asp
            435                 440                 445

Ser Asn Thr Ile Arg Ile Ala Gln Pro Lys Leu Ala Lys Pro Val Val
        450                 455                 460

Asp Ile Thr Thr Leu Asn Pro Thr Ile Ala Gly Ser Gly Ser Val Val
465                 470                 475                 480

Ala Ala Asn Ser Glu Gly Gln Ile Ser Asp Thr Met Gln Ile Val Ser
                485                 490                 495

Leu Gln Leu Asn
            500

<210> SEQ ID NO 65
<211> LENGTH: 1068
<212> TYPE: PRT
<213> ORGANISM: Chlamydia trachomatis

<400> SEQUENCE: 65
```

```
Thr Val Lys Ala Ile Val Glu Ser Thr Pro Glu Ala Pro Glu Glu Ile
1               5                   10                  15

Pro Pro Val Glu Gly Glu Ser Thr Ala Thr Glu Asp Pro Asn Ser
            20                  25                  30

Asn Thr Glu Gly Ser Ser Ala Asn Thr Asn Leu Glu Gly Ser Gln Gly
        35                  40                  45

Asp Thr Ala Asp Thr Gly Thr Gly Asp Val Asn Asn Glu Ser Gln Asp
    50                  55                  60

Thr Ser Asp Thr Gly Asn Ala Glu Ser Glu Glu Gln Leu Gln Asp Ser
65                  70                  75                  80

Thr Gln Ser Asn Glu Glu Asn Thr Leu Pro Asn Ser Asn Ile Asp Gln
                85                  90                  95

Ser Asn Glu Asn Thr Asp Glu Ser Ser Asp Ser His Thr Glu Glu Ile
                100                 105                 110

Thr Asp Glu Ser Val Ser Ser Ser Glu Ser Gly Ser Ser Thr Pro
            115                 120                 125

Gln Asp Gly Gly Ala Ala Ser Ser Gly Ala Pro Ser Gly Asp Gln Ser
    130                 135                 140

Ile Ser Ala Asn Ala Cys Leu Ala Lys Ser Tyr Ala Ala Ser Thr Asp
145                 150                 155                 160

Ser Ser Pro Val Ser Asn Ser Ser Gly Ser Glu Glu Pro Val Thr Ser
                165                 170                 175

Ser Ser Asp Ser Asp Val Thr Ala Ser Ser Asp Asn Pro Asp Ser Ser
            180                 185                 190

Ser Ser Gly Asp Ser Ala Gly Asp Ser Glu Glu Pro Thr Glu Pro Glu
        195                 200                 205

Ala Gly Ser Thr Thr Glu Thr Leu Thr Leu Ile Gly Gly Ala Ile
    210                 215                 220

Tyr Gly Glu Thr Val Lys Ile Glu Asn Phe Ser Gly Ser Arg Gln Asn
225                 230                 235                 240

Ala Glu Glu Asn Leu Lys Asn Phe Ala Lys Glu Leu Lys Leu Pro Asp
            245                 250                 255

Val Ala Phe Asp Gln Asn Asn Thr Cys Ile Leu Phe Val Asp Gly Glu
            260                 265                 270

Phe Ser Leu His Leu Thr Tyr Glu Glu His Ser Asp Arg Leu Tyr Val
        275                 280                 285

Tyr Ala Pro Leu Leu Asp Gly Leu Pro Asp Asn Pro Gln Arg Arg Leu
    290                 295                 300

Ala Leu Tyr Glu Lys Leu Leu Glu Gly Ser Met Leu Gly Gly Gln Met
305                 310                 315                 320

Ala Gly Gly Gly Val Gly Val Ala Thr Lys Glu Gln Leu Ile Leu Met
                325                 330                 335

His Cys Val Leu Asp Met Lys Tyr Ala Glu Thr Asn Leu Leu Lys Ala
            340                 345                 350

Phe Ala Gln Leu Phe Ile Glu Thr Val Val Lys Trp Arg Thr Val Cys
        355                 360                 365

Ser Asp Ile Ser Ala Gly Arg Glu Pro Thr Val Asp Thr Met Pro Gln
    370                 375                 380

Met Pro Gln Gly Gly Gly Gly Gly Ile Gln Pro Pro Ala Gly Ile
385                 390                 395                 400

Arg Ala Ser Arg Gln Asn Ala Glu Glu Asn Leu Lys Asn Phe Ala Lys
                405                 410                 415
```

```
Glu Leu Lys Leu Pro Asp Val Ala Phe Asp Gln Asn Asn Thr Cys Ile
            420                 425                 430
Leu Phe Val Asp Gly Glu Phe Ser Leu His Leu Thr Tyr Glu Glu His
        435                 440                 445
Ser Asp Arg Leu Tyr Val Tyr Ala Pro Leu Leu Asp Gly Leu Pro Asp
450                 455                 460
Asn Pro Gln Arg Arg Leu Ala Leu Tyr Glu Lys Leu Leu Glu Gly Ser
465                 470                 475                 480
Met Leu Gly Gly Gln Met Ala Gly Gly Val Gly Val Ala Thr Lys
                485                 490                 495
Glu Gln Leu Ile Leu Met His Cys Val Leu Asp Met Lys Tyr Ala Glu
            500                 505                 510
Thr Asn Leu Leu Lys Ala Phe Ala Gln Leu Phe Ile Glu Thr Val Val
        515                 520                 525
Lys Trp Arg Thr Val Cys Ser Asp Ile Ser Ala Gly Arg Glu Pro Thr
        530                 535                 540
Val Asp Thr Met Pro Gln Met Pro Gln Gly Gly Gly Gly Ile Gln
545                 550                 555                 560
Pro Pro Pro Ala Gly Ile Arg Ala Asp Ala Ile Ser Met Arg Val Gly
                565                 570                 575
Tyr Tyr Gly Asp Phe Val Phe Asp Arg Val Leu Lys Thr Asp Val Asn
                580                 585                 590
Lys Glu Phe Gln Met Gly Ala Lys Pro Thr Thr Asp Thr Gly Asn Ser
        595                 600                 605
Ala Ala Pro Ser Thr Leu Thr Ala Arg Glu Asn Pro Ala Tyr Gly Arg
610                 615                 620
His Met Gln Asp Ala Glu Met Phe Thr Asn Ala Ala Ser Met Ala Leu
625                 630                 635                 640
Asn Ile Trp Asp Arg Phe Asp Val Phe Ser Thr Leu Gly Ala Thr Ser
                645                 650                 655
Gly Tyr Leu Lys Gly Asn Ser Ala Ser Phe Asn Leu Val Gly Leu Phe
            660                 665                 670
Gly Asp Asn Glu Asn Gln Lys Thr Val Lys Ala Glu Ser Val Pro Asn
        675                 680                 685
Met Ser Phe Asp Gln Ser Val Val Glu Leu Tyr Thr Asp Thr Thr Phe
        690                 695                 700
Ala Trp Ser Val Gly Ala Arg Ala Leu Trp Glu Ser Gly Ser Ala
705                 710                 715                 720
Thr Leu Gly Ala Ser Phe Gln Tyr Ala Gln Ser Lys Pro Lys Val Glu
                725                 730                 735
Glu Leu Asn Val Leu Ser Asn Ala Ala Glu Phe Thr Ile Asn Lys Pro
            740                 745                 750
Lys Gly Tyr Val Gly Lys Glu Phe Pro Leu Asp Leu Thr Ala Gly Thr
        755                 760                 765
Asp Ala Ala Thr Gly Thr Lys Asp Ala Ser Ile Asp Tyr His Glu Trp
770                 775                 780
Gln Ala Ser Leu Ala Leu Ser Tyr Arg Leu Asn Met Phe Thr Pro Tyr
785                 790                 795                 800
Ile Gly Val Lys Trp Ser Arg Ala Ser Phe Asp Ala Asp Thr Ile Arg
                805                 810                 815
Ile Ala Gln Pro Lys Ser Ala Thr Ala Ile Phe Asp Thr Thr Thr Leu
            820                 825                 830
Asn Pro Thr Ile Ala Gly Ala Gly Asp Val Lys Thr Gly Ala Glu Gly
```

```
                    835                 840                 845
Gln Leu Gly Asp Thr Met Gln Ile Val Ser Leu Gln Leu Asn Asn Met
    850                 855                 860

Phe Thr Pro Tyr Ile Gly Val Lys Trp Ser Arg Ala Ser Phe Asp Ala
865                 870                 875                 880

Asp Thr Ile Arg Ile Ala Gln Pro Lys Ser Ala Thr Ala Ile Phe Asp
                885                 890                 895

Thr Thr Thr Leu Asn Pro Thr Ile Ala Gly Ala Gly Asp Val Lys Ala
            900                 905                 910

Ser Ala Glu Gly Gln Leu Gly Asp Thr Met Gln Ile Val Ser Leu Gln
        915                 920                 925

Leu Asn Asn Met Phe Thr Pro Tyr Ile Gly Val Lys Trp Ser Arg Ala
    930                 935                 940

Ser Phe Asp Ser Asp Thr Ile Arg Ile Ala Gln Pro Arg Leu Val Thr
945                 950                 955                 960

Pro Val Val Asp Ile Thr Thr Leu Asn Pro Thr Ile Ala Gly Ser Gly
                965                 970                 975

Ser Val Ala Gly Ala Asn Thr Glu Gly Gln Ile Ser Asp Thr Met Gln
            980                 985                 990

Ile Val Ser Leu Gln Leu Asn Asn Met Phe Thr Pro Tyr Ile Gly Val
        995                 1000                1005

Lys Trp Ser Arg Ala Ser Phe Asp Ser Asn Thr Ile Arg Ile Ala
    1010                1015                1020

Gln Pro Lys Leu Ala Lys Pro Val Val Asp Ile Thr Thr Leu Asn
    1025                1030                1035

Pro Thr Ile Ala Gly Ser Gly Ser Val Ala Ala Asn Ser Glu
    1040                1045                1050

Gly Gln Ile Ser Asp Thr Met Gln Ile Val Ser Leu Gln Leu Asn
    1055                1060                1065

<210> SEQ ID NO 66
<211> LENGTH: 606
<212> TYPE: PRT
<213> ORGANISM: Chlamydia trachomatis

<400> SEQUENCE: 66

Ser Arg Gln Asn Ala Glu Glu Asn Leu Lys Asn Phe Ala Lys Glu Leu
1               5                   10                  15

Lys Leu Pro Asp Val Ala Phe Asp Gln Asn Asn Thr Cys Ile Leu Phe
            20                  25                  30

Val Asp Gly Glu Phe Ser Leu His Leu Thr Tyr Glu Glu His Ser Asp
        35                  40                  45

Arg Leu Tyr Val Tyr Ala Pro Leu Leu Asp Gly Leu Pro Asp Asn Pro
    50                  55                  60

Gln Arg Arg Leu Ala Leu Tyr Glu Lys Leu Leu Glu Gly Ser Met Leu
65                  70                  75                  80

Gly Gly Gln Met Ala Gly Gly Gly Val Gly Val Ala Thr Lys Glu Gln
            85                  90                  95

Leu Ile Leu Met His Cys Val Leu Asp Met Lys Tyr Ala Glu Thr Asn
            100                 105                 110

Leu Leu Lys Ala Phe Ala Gln Leu Phe Ile Glu Thr Val Val Lys Trp
        115                 120                 125

Arg Thr Val Cys Ser Asp Ile Ser Ala Gly Arg Glu Pro Thr Val Asp
    130                 135                 140
```

```
Thr Met Pro Gln Met Pro Gln Gly Gly Gly Gly Ile Gln Pro Pro
145                 150                 155                 160

Pro Ala Gly Ile Arg Ala Ser Arg Gln Asn Ala Glu Glu Asn Leu Lys
            165                 170                 175

Asn Phe Ala Lys Glu Leu Lys Leu Pro Asp Val Ala Phe Asp Gln Asn
                180                 185                 190

Asn Thr Cys Ile Leu Phe Val Asp Gly Glu Phe Ser Leu His Leu Thr
        195                 200                 205

Tyr Glu Glu His Ser Asp Arg Leu Tyr Val Tyr Ala Pro Leu Leu Asp
    210                 215                 220

Gly Leu Pro Asp Asn Pro Gln Arg Arg Leu Ala Leu Tyr Glu Lys Leu
225                 230                 235                 240

Leu Glu Gly Ser Met Leu Gly Gly Gln Met Ala Gly Gly Val Gly
                245                 250                 255

Val Ala Thr Lys Glu Gln Leu Ile Leu Met His Cys Val Leu Asp Met
                260                 265                 270

Lys Tyr Ala Glu Thr Asn Leu Leu Lys Ala Phe Ala Gln Leu Phe Ile
            275                 280                 285

Glu Thr Val Val Lys Trp Arg Thr Val Cys Ser Asp Ile Ser Ala Gly
        290                 295                 300

Arg Glu Pro Thr Val Asp Thr Met Pro Gln Met Pro Gln Gly Gly Gly
305                 310                 315                 320

Gly Gly Ile Gln Pro Pro Ala Gly Ile Arg Ala Asn Met Phe Thr
                325                 330                 335

Pro Tyr Ile Gly Val Lys Trp Ser Arg Ala Ser Phe Asp Ala Asp Thr
            340                 345                 350

Ile Arg Ile Ala Gln Pro Lys Ser Ala Thr Ala Ile Phe Asp Thr Thr
        355                 360                 365

Thr Leu Asn Pro Thr Ile Ala Gly Ala Gly Asp Val Lys Thr Gly Ala
    370                 375                 380

Glu Gly Gln Leu Gly Asp Thr Met Gln Ile Val Ser Leu Gln Leu Asn
385                 390                 395                 400

Asn Met Phe Thr Pro Tyr Ile Gly Val Lys Trp Ser Arg Ala Ser Phe
                405                 410                 415

Asp Ala Asp Thr Ile Arg Ile Ala Gln Pro Lys Ser Ala Thr Ala Ile
            420                 425                 430

Phe Asp Thr Thr Thr Leu Asn Pro Thr Ile Ala Gly Ala Gly Asp Val
        435                 440                 445

Lys Ala Ser Ala Glu Gly Gln Leu Gly Asp Thr Met Gln Ile Val Ser
    450                 455                 460

Leu Gln Leu Asn Asn Met Phe Thr Pro Tyr Ile Gly Val Lys Trp Ser
465                 470                 475                 480

Arg Ala Ser Phe Asp Ser Asp Thr Ile Arg Ile Ala Gln Pro Arg Leu
                485                 490                 495

Val Thr Pro Val Val Asp Ile Thr Thr Leu Asn Pro Thr Ile Ala Gly
            500                 505                 510

Ser Gly Ser Val Ala Gly Ala Asn Thr Glu Gly Gln Ile Ser Asp Thr
        515                 520                 525

Met Gln Ile Val Ser Leu Gln Leu Asn Asn Met Phe Thr Pro Tyr Ile
    530                 535                 540

Gly Val Lys Trp Ser Arg Ala Ser Phe Asp Ser Asn Thr Ile Arg Ile
545                 550                 555                 560

Ala Gln Pro Lys Leu Ala Lys Pro Val Val Asp Ile Thr Thr Leu Asn
```

```
                        565                 570                 575
Pro Thr Ile Ala Gly Ser Gly Ser Val Val Ala Ala Asn Ser Glu Gly
                    580                 585                 590
Gln Ile Ser Asp Thr Met Gln Ile Val Ser Leu Gln Leu Asn
                595                 600                 605

<210> SEQ ID NO 67
<211> LENGTH: 1093
<212> TYPE: PRT
<213> ORGANISM: Chlamydia trachomatis

<400> SEQUENCE: 67

Ser Arg Gln Asn Ala Glu Glu Asn Leu Lys Asn Phe Ala Lys Glu Leu
1               5                   10                  15
Lys Leu Pro Asp Val Ala Phe Asp Gln Asn Asn Thr Cys Ile Leu Phe
                20                  25                  30
Val Asp Gly Glu Phe Ser Leu His Leu Thr Tyr Glu Glu His Ser Asp
            35                  40                  45
Arg Leu Tyr Val Tyr Ala Pro Leu Leu Asp Gly Leu Pro Asp Asn Pro
        50                  55                  60
Gln Arg Arg Leu Ala Leu Tyr Glu Lys Leu Leu Glu Gly Ser Met Leu
65                  70                  75                  80
Gly Gly Gln Met Ala Gly Gly Val Gly Val Ala Thr Lys Glu Gln
                85                  90                  95
Leu Ile Leu Met His Cys Val Leu Asp Met Lys Tyr Ala Glu Thr Asn
            100                 105                 110
Leu Leu Lys Ala Phe Ala Gln Leu Phe Ile Glu Thr Val Val Lys Trp
        115                 120                 125
Arg Thr Val Cys Ser Asp Ile Ser Ala Gly Arg Glu Pro Thr Val Asp
130                 135                 140
Thr Met Pro Gln Met Pro Gln Gly Gly Gly Gly Ile Gln Pro Pro
145                 150                 155                 160
Pro Ala Gly Ile Arg Ala Ser Arg Gln Asn Ala Glu Asn Leu Lys
                165                 170                 175
Asn Phe Ala Lys Glu Leu Lys Leu Pro Asp Val Ala Phe Asp Gln Asn
            180                 185                 190
Asn Thr Cys Ile Leu Phe Val Asp Gly Glu Phe Ser Leu His Leu Thr
        195                 200                 205
Tyr Glu Glu His Ser Asp Arg Leu Tyr Val Tyr Ala Pro Leu Leu Asp
    210                 215                 220
Gly Leu Pro Asp Asn Pro Gln Arg Arg Leu Ala Leu Tyr Glu Lys Leu
225                 230                 235                 240
Leu Glu Gly Ser Met Leu Gly Gly Gln Met Ala Gly Gly Val Gly
                245                 250                 255
Val Ala Thr Lys Glu Gln Leu Ile Leu Met His Cys Val Leu Asp Met
            260                 265                 270
Lys Tyr Ala Glu Thr Asn Leu Leu Lys Ala Phe Ala Gln Leu Phe Ile
        275                 280                 285
Glu Thr Val Val Lys Trp Arg Thr Val Cys Ser Asp Ile Ser Ala Gly
    290                 295                 300
Arg Glu Pro Thr Val Asp Thr Met Pro Gln Met Pro Gln Gly Gly Gly
305                 310                 315                 320
Gly Gly Ile Gln Pro Pro Pro Ala Gly Ile Arg Ala Gly Ile Ala His
                325                 330                 335
```

-continued

```
Thr Glu Trp Glu Ser Val Ile Gly Leu Glu Val His Val Glu Leu Asn
                340                 345                 350
Thr Glu Ser Lys Leu Phe Ser Pro Ala Arg Asn His Phe Gly Asp Glu
            355                 360                 365
Pro Asn Thr Asn Ile Ser Pro Val Cys Thr Gly Met Pro Gly Ser Leu
        370                 375                 380
Pro Val Leu Asn Lys Asp Ala Val Arg Lys Ala Val Leu Phe Gly Cys
385                 390                 395                 400
Ala Val Glu Gly Asp Val Ala Leu Phe Ser Arg Phe Asp Arg Lys Ser
                405                 410                 415
Tyr Phe Tyr Pro Asp Ser Pro Arg Asn Phe Gln Ile Thr Gln Tyr Glu
            420                 425                 430
His Pro Ile Val Arg Gly Gly Cys Ile Arg Ala Val Glu Gly Glu
        435                 440                 445
Glu Lys Thr Phe Glu Leu Ala Gln Thr His Leu Glu Asp Asp Ala Gly
                450                 455                 460
Met Leu Lys His Phe Gly Asp Phe Ala Gly Val Asp Tyr Asn Arg Ala
465                 470                 475                 480
Gly Val Pro Leu Ile Glu Ile Val Ser Lys Pro Cys Met Phe Ser Ala
                485                 490                 495
Glu Asp Ala Val Ala Tyr Ala Asn Ala Leu Val Ser Ile Leu Gly Tyr
            500                 505                 510
Ile Gly Ile Ser Asp Cys Asn Met Glu Glu Gly Ser Ile Arg Phe Asp
        515                 520                 525
Val Asn Ile Ser Val Arg Pro Arg Gly Ser Arg Glu Leu Arg Asn Lys
530                 535                 540
Val Glu Ile Lys Asn Met Asn Ser Phe Thr Phe Met Ala Gln Ala Leu
545                 550                 555                 560
Glu Ala Glu Lys Arg Arg Gln Ile Glu Glu Tyr Leu Ser Tyr Pro Asn
                565                 570                 575
Glu Asp Pro Lys Lys Val Val Pro Ala Ala Thr Tyr Arg Trp Asp Pro
            580                 585                 590
Glu Lys Lys Lys Thr Val Leu Met Arg Leu Lys Glu Arg Ala Glu Asp
        595                 600                 605
Tyr Met Tyr Phe Val Glu Pro Asp Leu Pro Val Leu Gln Ile Thr Glu
610                 615                 620
Thr Tyr Ile Asp Glu Val Arg Gln Thr Leu Pro Glu Leu Pro His Ser
625                 630                 635                 640
Lys Tyr Met Arg Tyr Ile Thr Asp Phe Asp Ile Ala Glu Asp Leu Ala
                645                 650                 655
Met Ile Leu Val Gly Asp Arg His Thr Ala His Phe Phe Glu Thr Ala
            660                 665                 670
Thr Met Ser Cys Lys Asn Tyr Arg Ala Leu Ser Asn Trp Ile Thr Val
        675                 680                 685
Glu Phe Ala Gly Arg Cys Lys Ala Arg Gly Lys Thr Leu Pro Phe Thr
690                 695                 700
Gly Ile Leu Pro Glu Trp Val Ala Gln Leu Val Asn Phe Ile Asp Arg
705                 710                 715                 720
Gly Val Ile Thr Gly Lys Ile Ala Lys Glu Ile Ala Asp Arg Met Val
                725                 730                 735
Ser Ser Phe Gly Glu Ser Pro Glu Asp Ile Leu Arg Arg His Pro Ser
            740                 745                 750
Leu Leu Pro Met Thr Asp Asp His Ala Leu Arg Ala Ile Val Lys Glu
```

-continued

```
                 755                 760                 765

Val Val Ala Gln Asn Thr Ala Ser Val Ala Asp Tyr Lys Asn Gly Lys
        770                 775                 780

Ala Lys Ala Leu Gly Phe Leu Val Gly Gln Ile Met Lys Arg Thr Glu
        785                 790                 795                 800

Gly Lys Ala Pro Pro Lys Arg Val Asn Glu Leu Leu Leu Ala Ala Met
                        805                 810                 815

Arg Asp Met Asn Met Phe Thr Pro Tyr Ile Gly Val Lys Trp Ser Arg
                        820                 825                 830

Ala Ser Phe Asp Ala Asp Thr Ile Arg Ile Ala Gln Pro Lys Ser Ala
                        835                 840                 845

Thr Ala Ile Phe Asp Thr Thr Thr Leu Asn Pro Thr Ile Ala Gly Ala
                        850                 855                 860

Gly Asp Val Lys Thr Gly Ala Glu Gly Gln Leu Gly Asp Thr Met Gln
        865                 870                 875                 880

Ile Val Ser Leu Gln Leu Asn Asn Met Phe Thr Pro Tyr Ile Gly Val
                        885                 890                 895

Lys Trp Ser Arg Ala Ser Phe Asp Ala Asp Thr Ile Arg Ile Ala Gln
                        900                 905                 910

Pro Lys Ser Ala Thr Ala Ile Phe Asp Thr Thr Thr Leu Asn Pro Thr
                        915                 920                 925

Ile Ala Gly Ala Gly Asp Val Lys Ala Ser Ala Glu Gly Gln Leu Gly
        930                 935                 940

Asp Thr Met Gln Ile Val Ser Leu Gln Leu Asn Asn Met Phe Thr Pro
        945                 950                 955                 960

Tyr Ile Gly Val Lys Trp Ser Arg Ala Ser Phe Asp Ser Asp Thr Ile
                        965                 970                 975

Arg Ile Ala Gln Pro Arg Leu Val Thr Pro Val Val Asp Ile Thr Thr
                        980                 985                 990

Leu Asn Pro Thr Ile Ala Gly Ser Gly Ser Val Ala Gly Ala Asn Thr
                        995                1000                1005

Glu Gly Gln Ile Ser Asp Thr Met Gln Ile Val Ser Leu Gln Leu
                       1010                1015                1020

Asn Asn Met Phe Thr Pro Tyr Ile Gly Val Lys Trp Ser Arg Ala
                       1025                1030                1035

Ser Phe Asp Ser Asn Thr Ile Arg Ile Ala Gln Pro Lys Leu Ala
                       1040                1045                1050

Lys Pro Val Val Asp Ile Thr Thr Leu Asn Pro Thr Ile Ala Gly
                       1055                1060                1065

Ser Gly Ser Val Val Ala Asn Ser Glu Gly Gln Ile Ser Asp
                       1070                1075                1080

Thr Met Gln Ile Val Ser Leu Gln Leu Asn
                       1085                1090

<210> SEQ ID NO 68
<211> LENGTH: 393
<212> TYPE: PRT
<213> ORGANISM: Chlamydia trachomatis

<400> SEQUENCE: 68

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30
```

```
Leu Met Ile Asp Gly Ile Leu Trp Glu Gly Phe Gly Asp Pro Cys
         35                  40                  45

Asp Pro Cys Ala Thr Trp Cys Asp Ala Ile Ser Met Arg Val Gly Tyr
 50                  55                  60

Tyr Gly Asp Phe Val Phe Asp Arg Val Leu Lys Thr Asp Val Asn Lys
 65                  70                  75                  80

Glu Phe Gln Met Gly Ala Lys Pro Thr Thr Asp Thr Gly Asn Ser Ala
                 85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390

<210> SEQ ID NO 69
<211> LENGTH: 122
<212> TYPE: PRT
<213> ORGANISM: Chlamydia trachomatis

<400> SEQUENCE: 69

Ser Ala Thr Ala Ile Phe Asp Thr Thr Thr Leu Asn Pro Thr Ile Ala
 1               5                  10                  15
```

-continued

Gly Ala Gly Asp Val Lys Thr Gly Ala Glu Gly Gln Leu Gly Ser Ala
            20                  25                  30

Thr Ala Ile Phe Asp Thr Thr Leu Asn Pro Thr Ile Ala Gly Ala
        35                  40                  45

Gly Asp Val Lys Ala Ser Ala Glu Gly Gln Leu Gly Leu Val Thr Pro
50                  55                  60

Val Val Asp Ile Thr Thr Leu Asn Pro Thr Ile Ala Gly Ser Gly Ser
65                  70                  75                  80

Val Ala Gly Ala Asn Thr Glu Gly Gln Ile Ser Leu Ala Lys Pro Val
                85                  90                  95

Val Asp Ile Thr Thr Leu Asn Pro Thr Ile Ala Gly Ser Gly Ser Val
            100                 105                 110

Val Ala Ala Asn Ser Glu Gly Gln Ile Ser
            115                 120

<210> SEQ ID NO 70
<211> LENGTH: 178
<212> TYPE: PRT
<213> ORGANISM: Chlamydia trachomatis

<400> SEQUENCE: 70

Ile Arg Ile Ala Gln Pro Lys Ser Ala Thr Ala Ile Phe Asp Thr Thr
1               5                   10                  15

Thr Leu Asn Pro Thr Ile Ala Gly Ala Gly Asp Val Lys Thr Gly Ala
            20                  25                  30

Glu Gly Gln Leu Gly Asp Thr Met Gln Ile Val Ser Ile Arg Ile Ala
        35                  40                  45

Gln Pro Lys Ser Ala Thr Ala Ile Phe Asp Thr Thr Thr Leu Asn Pro
50                  55                  60

Thr Ile Ala Gly Ala Gly Asp Val Lys Ala Ser Ala Glu Gly Gln Leu
65                  70                  75                  80

Gly Asp Thr Met Gln Ile Val Ser Ile Arg Ile Ala Gln Pro Arg Leu
                85                  90                  95

Val Thr Pro Val Val Asp Ile Thr Thr Leu Asn Pro Thr Ile Ala Gly
            100                 105                 110

Ser Gly Ser Val Ala Gly Ala Asn Thr Glu Gly Gln Ile Ser Asp Thr
        115                 120                 125

Met Gln Ile Val Ser Ile Arg Ile Ala Gln Pro Lys Leu Ala Lys Pro
    130                 135                 140

Val Val Asp Ile Thr Thr Leu Asn Pro Thr Ile Ala Gly Ser Gly Ser
145                 150                 155                 160

Val Val Ala Ala Asn Ser Glu Gly Gln Ile Ser Asp Thr Met Gln Ile
                165                 170                 175

Val Ser

<210> SEQ ID NO 71
<211> LENGTH: 393
<212> TYPE: PRT
<213> ORGANISM: Chlamydia trachomatis

<400> SEQUENCE: 71

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
         35                  40                  45

Asp Pro Cys Thr Thr Trp Cys Asp Ala Ile Ser Met Arg Met Gly Tyr
 50                  55                  60

Tyr Gly Asp Phe Val Phe Asp Arg Val Leu Lys Thr Asp Val Asn Lys
 65                  70                  75                  80

Glu Phe Gln Met Gly Asp Lys Pro Thr Ser Thr Thr Gly Asn Ala Thr
                 85                  90                  95

Ala Pro Thr Thr Leu Thr Ala Arg Glu Asn Pro Ala Tyr Gly Arg His
             100                 105                 110

Met Gln Asp Ala Glu Met Phe Thr Asn Ala Ala Cys Met Ala Leu Asn
         115                 120                 125

Ile Trp Asp Arg Phe Asp Val Phe Cys Thr Leu Gly Ala Ser Ser Gly
     130                 135                 140

Tyr Leu Lys Gly Asn Ser Ala Ser Phe Asn Leu Val Gly Leu Phe Gly
145                 150                 155                 160

Asp Asn Glu Asn Gln Ser Thr Val Lys Thr Asn Ser Val Pro Asn Met
                165                 170                 175

Ser Leu Asp Gln Ser Val Val Glu Leu Tyr Thr Asp Thr Ala Phe Ser
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Gln Glu Phe Pro Leu Ala Leu Ile Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Leu Asn
305                 310                 315                 320

Pro Thr Ile Ala Gly Ala Gly Asp Val Lys Ala Ser Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390

<210> SEQ ID NO 72
<211> LENGTH: 395
<212> TYPE: PRT
<213> ORGANISM: Chlamydia trachomatis

<400> SEQUENCE: 72

Met Lys Lys Leu Leu Lys Ser Val Leu Val Phe Ala Ala Leu Ser Ser
 1               5                  10                  15

Ala Ser Ser Leu Gln Ala Leu Pro Val Gly Asn Pro Ala Glu Pro Ser
             20                  25                  30

Leu Met Ile Asp Gly Ile Leu Trp Glu Gly Phe Gly Asp Pro Cys
         35                  40                  45

Asp Pro Cys Thr Thr Trp Cys Asp Ala Ile Ser Met Arg Met Gly Tyr
 50                  55                  60

Tyr Gly Asp Phe Val Phe Asp Arg Val Leu Lys Thr Asp Val Asn Lys
 65                  70                  75                  80

Glu Phe Glu Met Gly Glu Ala Leu Ala Gly Ala Ser Gly Asn Thr Thr
                 85                  90                  95

Ser Thr Leu Ser Lys Leu Val Glu Arg Thr Asn Pro Ala Tyr Gly Lys
                100                 105                 110

His Met Gln Asp Ala Glu Met Phe Thr Asn Ala Ala Cys Met Thr Leu
                115                 120                 125

Asn Ile Trp Asp Arg Phe Asp Val Phe Cys Thr Leu Gly Ala Thr Ser
        130                 135                 140

Gly Tyr Leu Lys Gly Asn Ser Ala Ser Phe Asn Leu Val Gly Leu Phe
145                 150                 155                 160

Gly Asp Gly Val Asn Ala Thr Lys Pro Ala Ala Asp Ser Ile Pro Asn
                165                 170                 175

Val Gln Leu Asn Gln Ser Val Val Glu Leu Tyr Thr Asp Thr Thr Phe
                180                 185                 190

Ala Trp Ser Val Gly Ala Arg Ala Leu Trp Glu Cys Gly Cys Ala
                195                 200                 205

Thr Leu Gly Ala Ser Phe Gln Tyr Ala Gln Ser Lys Pro Lys Ile Glu
                210                 215                 220

Glu Leu Asn Val Leu Cys Asn Ala Ala Glu Phe Thr Ile Asn Lys Pro
225                 230                 235                 240

Lys Gly Tyr Val Gly Lys Glu Phe Pro Leu Asp Leu Thr Ala Gly Thr
                245                 250                 255

Asp Ala Ala Thr Gly Thr Lys Asp Ala Ser Ile Asp Tyr His Glu Trp
                260                 265                 270

Gln Ala Ser Leu Ser Leu Ser Tyr Arg Leu Asn Met Phe Thr Pro Tyr
                275                 280                 285

Ile Gly Val Lys Trp Ser Arg Ala Ser Phe Asp Ser Asp Thr Ile Arg
                290                 295                 300

Ile Ala Gln Pro Arg Leu Val Thr Pro Val Val Asp Ile Thr Thr Leu
305                 310                 315                 320

Asn Pro Thr Ile Ala Gly Cys Gly Ser Val Ala Gly Ala Asn Thr Glu
                325                 330                 335

Gly Gln Ile Ser Asp Thr Met Gln Ile Val Ser Leu Gln Leu Asn Lys
                340                 345                 350

Met Lys Ser Arg Lys Ser Cys Gly Ile Ala Val Gly Thr Thr Ile Val
                355                 360                 365

Asp Ala Asp Lys Tyr Ala Val Thr Val Glu Thr Arg Leu Ile Asp Glu
                370                 375                 380

Arg Ala Ala His Val Asn Ala Gln Phe Arg Phe
385                 390                 395

<210> SEQ ID NO 73
<211> LENGTH: 393
<212> TYPE: PRT
<213> ORGANISM: Chlamydia trachomatis

<400> SEQUENCE: 73

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Glu Met Gly Glu Ala Leu Ala Gly Ala Ser Gly Asn Thr Thr
                85                  90                  95

Ser Thr Leu Ser Lys Leu Val Glu Arg Thr Asn Pro Ala Tyr Gly Lys
            100                 105                 110

His Met Gln Asp Ala Glu Met Phe Thr Asn Ala Ala Cys Met Ala Leu
        115                 120                 125

Asn Ile Trp Asp Arg Phe Asp Val Phe Cys Thr Leu Gly Ala Thr Ser
    130                 135                 140

Gly Tyr Leu Arg Gly Asn Ser Ala Ser Phe Asn Leu Val Gly Leu Phe
145                 150                 155                 160

Gly Asp Ser Glu Asn Ala Thr Gln Pro Ala Ala Thr Ser Ile Pro Asn
                165                 170                 175

Val Gln Leu Asn Gln Ser Val Val Glu Leu Tyr Thr Asp Thr Ala Phe
            180                 185                 190

Ala Trp Ser Val Gly Ala Arg Ala Ala Leu Trp Glu Cys Gly Cys Ala
        195                 200                 205

Thr Leu Gly Ala Ser Phe Gln Tyr Ala Gln Ser Lys Pro Lys Val Glu
    210                 215                 220

Glu Leu Asn Val Leu Cys Asn Ala Ala Glu Phe Thr Ile Asn Lys Pro
225                 230                 235                 240

Lys Gly Tyr Val Gly Gln Glu Phe Pro Leu Ala Leu Thr Ala Gly Thr
                245                 250                 255

Asp Ala Ala Thr Gly Thr Lys Asp Ala Ser Ile Asp Tyr His Glu Trp
            260                 265                 270

Gln Ala Ser Leu Ser Leu Ser Tyr Arg Leu Asn Met Phe Thr Pro Tyr
        275                 280                 285

Ile Gly Val Lys Trp Ser Arg Ala Ser Phe Asp Ser Asn Thr Ile Arg
    290                 295                 300

Ile Ala Gln Pro Lys Leu Ala Lys Pro Val Val Asp Ile Thr Thr Leu
305                 310                 315                 320

Asn Pro Thr Ile Ala Gly Cys Gly Ser Val Val Ala Ala Asn Ser Glu
                325                 330                 335

Gly Gln Ile Ser Asp Thr Met Gln Ile Val Ser Leu Gln Leu Asn Lys
            340                 345                 350

Met Lys Ser Arg Lys Ser Cys Gly Ile Ala Val Gly Thr Thr Ile Val
        355                 360                 365

Asp Ala Asp Lys Tyr Ala Val Thr Val Glu Thr Arg Leu Ile Asp Glu
    370                 375                 380

Arg Ala Ala His Val Asn Ala Gln Phe
385                 390

<210> SEQ ID NO 74

```
<211> LENGTH: 389
<212> TYPE: PRT
<213> ORGANISM: Chlamydia trachomatis

<400> SEQUENCE: 74

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Lys Asp Ile Ala Gly Leu
                85                  90                  95

Glu Asn Asp Pro Thr Thr Asn Val Ala Arg Pro Asn Pro Ala Tyr Gly
            100                 105                 110

Lys His Met Gln Asp Ala Glu Met Phe Thr Asn Ala Ala Tyr Met Ala
        115                 120                 125

Leu Asn Ile Trp Asp Arg Phe Asp Val Phe Cys Thr Leu Gly Ala Thr
    130                 135                 140

Thr Gly Tyr Leu Lys Gly Asn Ser Ala Ser Phe Asn Leu Val Gly Leu
145                 150                 155                 160

Phe Gly Thr Lys Thr Gln Ser Ser Asn Phe Asn Thr Ala Lys Leu Ile
                165                 170                 175

Pro Asn Ala Ala Leu Asn Gln Ala Val Val Glu Leu Tyr Thr Asp Thr
            180                 185                 190

Thr Phe Ala Trp Ser Val Gly Ala Arg Ala Ala Leu Trp Glu Cys Gly
        195                 200                 205

Cys Ala Thr Leu Gly Ala Ser Phe Gln Tyr Ala Gln Ser Lys Pro Lys
    210                 215                 220

Val Glu Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asp Ile Thr Ala
                245                 250                 255

Gly Thr Glu Ala Ala Thr Gly Thr Lys Asp Ala Ser Ile Asp Tyr His
            260                 265                 270

Glu Trp Gln Ala Ser Leu Ala Leu Ser Tyr Arg Leu Asn Met Phe Thr
        275                 280                 285

Pro Tyr Ile Gly Val Lys Trp Ser Arg Val Ser Phe Asp Ala Asp Thr
    290                 295                 300

Ile Arg Ile Ala Gln Pro Lys Leu Ala Glu Ala Ile Leu Asp Val Thr
305                 310                 315                 320

Thr Leu Asn Pro Thr Ile Ala Gly Lys Gly Thr Val Val Ala Ser Gly
                325                 330                 335

Ser Asp Asn Asp Leu Ala Asp Thr Met Gln Ile Val Ser Leu Gln Leu
            340                 345                 350

Asn Lys Met Lys Ser Arg Lys Ser Cys Gly Ile Ala Val Gly Thr Thr
        355                 360                 365

Ile Val Asp Ala Asp Lys Tyr Ala Val Thr Val Glu Thr Arg Leu Ile
370                 375                 380

Asp Glu Arg Ala Ala
```

385

<210> SEQ ID NO 75
<211> LENGTH: 397
<212> TYPE: PRT
<213> ORGANISM: Chlamydia trachomatis

<400> SEQUENCE: 75

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Ser Asp Val Ala Gly Leu
                85                  90                  95

Gln Asn Asp Pro Thr Thr Asn Val Ala Arg Pro Asn Pro Ala Tyr Gly
            100                 105                 110

Lys His Met Gln Asp Ala Glu Met Phe Thr Asn Ala Ala Tyr Met Ala
        115                 120                 125

Leu Asn Ile Trp Asp Arg Phe Asp Val Phe Cys Thr Leu Gly Ala Thr
    130                 135                 140

Thr Gly Tyr Leu Lys Gly Asn Ser Ala Ser Phe Asn Leu Val Gly Leu
145                 150                 155                 160

Phe Gly Thr Lys Thr Gln Ala Ser Ser Phe Asn Thr Ala Asn Leu Phe
                165                 170                 175

Pro Asn Thr Ala Leu Asn Gln Ala Val Val Glu Leu Tyr Thr Asp Thr
            180                 185                 190

Thr Phe Ala Trp Ser Val Gly Ala Arg Ala Ala Leu Trp Glu Cys Gly
        195                 200                 205

Cys Ala Thr Leu Gly Ala Ser Phe Gln Tyr Ala Gln Ser Lys Pro Lys
    210                 215                 220

Val Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asp Ile Thr Ala
                245                 250                 255

Gly Thr Glu Ala Ala Thr Gly Thr Lys Asp Ala Ser Ile Asp Tyr His
            260                 265                 270

Glu Trp Gln Ala Ser Leu Ala Leu Ser Tyr Arg Leu Asn Met Phe Thr
        275                 280                 285

Pro Tyr Ile Gly Val Lys Trp Ser Arg Val Ser Phe Asp Ala Asp Thr
    290                 295                 300

Ile Arg Ile Ala Gln Pro Lys Leu Ala Glu Ala Ile Leu Asp Val Thr
305                 310                 315                 320

Thr Leu Asn Pro Thr Ile Ala Gly Lys Gly Thr Val Val Ala Ser Gly
                325                 330                 335

Ser Glu Asn Asp Leu Ala Asp Thr Met Gln Ile Val Ser Leu Gln Leu
            340                 345                 350

Asn Lys Met Lys Ser Arg Lys Ser Cys Gly Ile Ala Val Gly Thr Thr
        355                 360                 365

```
Ile Val Asp Ala Asp Lys Tyr Ala Val Thr Val Glu Thr Arg Leu Ile
        370                 375                 380
Asp Glu Arg Ala Ala His Val Asn Ala Gln Phe Arg Phe
385                 390                 395

<210> SEQ ID NO 76
<211> LENGTH: 9
<212> TYPE: PRT
<213> ORGANISM: Chlamydia trachomatis

<400> SEQUENCE: 76

Thr Thr Leu Asn Pro Thr Ile Ala Gly
1               5

<210> SEQ ID NO 77
<211> LENGTH: 27
<212> TYPE: PRT
<213> ORGANISM: Chlamydia trachomatis

<400> SEQUENCE: 77

Ser Met Arg Val Gly Tyr Tyr Gly Asp Phe Val Phe Asp Arg Val Leu
1               5                   10                  15
Lys Thr Asp Val Asn Lys Glu Phe Gln Met Gly
            20                  25

<210> SEQ ID NO 78
<211> LENGTH: 26
<212> TYPE: PRT
<213> ORGANISM: Chlamydia trachomatis

<400> SEQUENCE: 78

Asn Pro Ala Tyr Gly Arg His Met Gln Asp Ala Glu Met Phe Thr Asn
1               5                   10                  15
Ala Ala Cys Met Ala Leu Asn Ile Trp Asp
            20                  25

<210> SEQ ID NO 79
<211> LENGTH: 8
<212> TYPE: PRT
<213> ORGANISM: Chlamydia trachomatis

<400> SEQUENCE: 79

Ser Ala Thr Ala Ile Phe Asp Thr
1               5

<210> SEQ ID NO 80
<211> LENGTH: 8
<212> TYPE: PRT
<213> ORGANISM: Chlamydia trachomatis

<400> SEQUENCE: 80

Leu Val Thr Pro Val Val Asp Ile
1               5

<210> SEQ ID NO 81
<211> LENGTH: 8
<212> TYPE: PRT
<213> ORGANISM: Chlamydia trachomatis

<400> SEQUENCE: 81

Leu Ala Lys Pro Val Val Asp Ile
1               5
```

```
<210> SEQ ID NO 82
<211> LENGTH: 8
<212> TYPE: PRT
<213> ORGANISM: Chlamydia trachomatis

<400> SEQUENCE: 82

Leu Ala Glu Ala Ile Leu Asp Val
1               5

<210> SEQ ID NO 83
<211> LENGTH: 13
<212> TYPE: PRT
<213> ORGANISM: Chlamydia trachomatis

<400> SEQUENCE: 83

Ala Gly Asp Val Lys Thr Gly Ala Glu Gly Gln Leu Gly
1               5                   10

<210> SEQ ID NO 84
<211> LENGTH: 13
<212> TYPE: PRT
<213> ORGANISM: Chlamydia trachomatis

<400> SEQUENCE: 84

Ala Gly Asp Val Lys Ala Ser Ala Glu Gly Gln Leu Gly
1               5                   10

<210> SEQ ID NO 85
<211> LENGTH: 14
<212> TYPE: PRT
<213> ORGANISM: Chlamydia trachomatis

<400> SEQUENCE: 85

Cys Gly Ser Val Ala Gly Ala Asn Thr Glu Gly Gln Ile Ser
1               5                   10

<210> SEQ ID NO 86
<211> LENGTH: 14
<212> TYPE: PRT
<213> ORGANISM: Chlamydia trachomatis

<400> SEQUENCE: 86

Cys Gly Ser Val Val Ala Ala Asn Ser Glu Gly Gln Ile Ser
1               5                   10

<210> SEQ ID NO 87
<211> LENGTH: 13
<212> TYPE: PRT
<213> ORGANISM: Chlamydia trachomatis

<400> SEQUENCE: 87

Lys Gly Thr Val Val Ser Ser Ala Glu Asn Glu Leu Ala
1               5                   10

<210> SEQ ID NO 88
<211> LENGTH: 14
<212> TYPE: PRT
<213> ORGANISM: Chlamydia trachomatis

<400> SEQUENCE: 88

Lys Gly Thr Val Val Ala Ser Gly Ser Glu Asn Asp Leu Ala
1               5                   10

<210> SEQ ID NO 89
<211> LENGTH: 20
```

-continued

```
<212> TYPE: PRT
<213> ORGANISM: Chlamydia trachomatis

<400> SEQUENCE: 89

Asp Ala Ser Ile Asp Tyr His Glu Trp Gln Ala Ser Leu Ala Leu Ser
1               5                   10                  15

Tyr Arg Leu Asn
            20

<210> SEQ ID NO 90
<211> LENGTH: 20
<212> TYPE: PRT
<213> ORGANISM: Chlamydia trachomatis

<400> SEQUENCE: 90

Ala Ser Leu Ala Leu Ser Tyr Arg Leu Asn Met Phe Thr Pro Tyr Ile
1               5                   10                  15

Gly Val Lys Trp
            20

<210> SEQ ID NO 91
<211> LENGTH: 20
<212> TYPE: PRT
<213> ORGANISM: Chlamydia trachomatis

<400> SEQUENCE: 91

Met Phe Thr Pro Tyr Ile Gly Val Lys Trp Ser Arg Ala Ser Phe Asp
1               5                   10                  15

Ala Asp Thr Ile
            20

<210> SEQ ID NO 92
<211> LENGTH: 20
<212> TYPE: PRT
<213> ORGANISM: Chlamydia trachomatis

<400> SEQUENCE: 92

Ser Arg Ala Ser Phe Asp Ala Asp Thr Ile Arg Ile Ala Gln Pro Lys
1               5                   10                  15

Ser Ala Thr Ala
            20

<210> SEQ ID NO 93
<211> LENGTH: 20
<212> TYPE: PRT
<213> ORGANISM: Chlamydia trachomatis

<400> SEQUENCE: 93

Arg Ile Ala Gln Pro Lys Ser Ala Thr Ala Ile Phe Asp Thr Thr Thr
1               5                   10                  15

Leu Asn Pro Thr
            20

<210> SEQ ID NO 94
<211> LENGTH: 20
<212> TYPE: PRT
<213> ORGANISM: Chlamydia trachomatis

<400> SEQUENCE: 94

Ile Phe Asp Thr Thr Thr Leu Asn Pro Thr Ile Ala Gly Ala Gly Asp
1               5                   10                  15

Val Lys Ala Ser
```

-continued

<210> SEQ ID NO 95
<211> LENGTH: 20
<212> TYPE: PRT
<213> ORGANISM: Chlamydia trachomatis

<400> SEQUENCE: 95

Ile Ala Gly Ala Gly Asp Val Lys Ala Ser Ala Glu Gly Gln Leu Gly
1               5                   10                  15

Asp Thr Met Gln
            20

<210> SEQ ID NO 96
<211> LENGTH: 20
<212> TYPE: PRT
<213> ORGANISM: Chlamydia trachomatis

<400> SEQUENCE: 96

Ala Glu Gly Gln Leu Gly Asp Thr Met Gln Ile Val Ser Leu Gln Leu
1               5                   10                  15

Asn Lys Met Lys
            20

<210> SEQ ID NO 97
<211> LENGTH: 20
<212> TYPE: PRT
<213> ORGANISM: Chlamydia trachomatis

<400> SEQUENCE: 97

Asp Ala Ser Ile Asp Tyr His Glu Trp Gln Ala Ser Leu Ser Leu Ser
1               5                   10                  15

Tyr Arg Leu Asn
            20

<210> SEQ ID NO 98
<211> LENGTH: 20
<212> TYPE: PRT
<213> ORGANISM: Chlamydia trachomatis

<400> SEQUENCE: 98

Ala Ser Leu Ser Leu Ser Tyr Arg Leu Asn Met Phe Thr Pro Tyr Ile
1               5                   10                  15

Gly Val Lys Trp
            20

<210> SEQ ID NO 99
<211> LENGTH: 20
<212> TYPE: PRT
<213> ORGANISM: Chlamydia trachomatis

<400> SEQUENCE: 99

Met Phe Thr Pro Tyr Ile Gly Val Lys Trp Ser Arg Ala Ser Phe Asp
1               5                   10                  15

Ser Asp Thr Ile
            20

<210> SEQ ID NO 100
<211> LENGTH: 20
<212> TYPE: PRT
<213> ORGANISM: Chlamydia trachomatis

<400> SEQUENCE: 100

-continued

Ser Arg Ala Ser Phe Asp Ser Asp Thr Ile Arg Ile Ala Gln Pro Arg
1               5                   10                  15

Leu Val Thr Pro
            20

<210> SEQ ID NO 101
<211> LENGTH: 20
<212> TYPE: PRT
<213> ORGANISM: Chlamydia trachomatis

<400> SEQUENCE: 101

Arg Ile Ala Gln Pro Arg Leu Val Thr Pro Val Val Asp Ile Thr Thr
1               5                   10                  15

Leu Asn Pro Thr
            20

<210> SEQ ID NO 102
<211> LENGTH: 20
<212> TYPE: PRT
<213> ORGANISM: Chlamydia trachomatis

<400> SEQUENCE: 102

Val Val Asp Ile Thr Thr Leu Asn Pro Thr Ile Ala Gly Cys Gly Ser
1               5                   10                  15

Val Ala Gly Ala
            20

<210> SEQ ID NO 103
<211> LENGTH: 21
<212> TYPE: PRT
<213> ORGANISM: Chlamydia trachomatis

<400> SEQUENCE: 103

Ile Ala Gly Cys Gly Ser Val Ala Gly Ala Asn Thr Glu Gly Gln Ile
1               5                   10                  15

Ser Asp Thr Met Gln
            20

<210> SEQ ID NO 104
<211> LENGTH: 20
<212> TYPE: PRT
<213> ORGANISM: Chlamydia trachomatis

<400> SEQUENCE: 104

Thr Glu Gly Gln Ile Ser Asp Thr Met Gln Ile Val Ser Leu Gln Leu
1               5                   10                  15

Asn Lys Met Lys
            20

<210> SEQ ID NO 105
<211> LENGTH: 9
<212> TYPE: PRT
<213> ORGANISM: Chlamydia trachomatis

<400> SEQUENCE: 105

Ser Arg Ala Ser Phe Asp Ala Asp Thr
1               5

<210> SEQ ID NO 106
<211> LENGTH: 9
<212> TYPE: PRT
<213> ORGANISM: Chlamydia trachomatis

```
<400> SEQUENCE: 106

Arg Ala Ser Phe Asp Ala Asp Thr Ile
1               5

<210> SEQ ID NO 107
<211> LENGTH: 9
<212> TYPE: PRT
<213> ORGANISM: Chlamydia trachomatis

<400> SEQUENCE: 107

Ala Ser Phe Asp Ala Asp Thr Ile Arg
1               5

<210> SEQ ID NO 108
<211> LENGTH: 9
<212> TYPE: PRT
<213> ORGANISM: Chlamydia trachomatis

<400> SEQUENCE: 108

Ser Phe Asp Ala Asp Thr Ile Arg Ile
1               5

<210> SEQ ID NO 109
<211> LENGTH: 9
<212> TYPE: PRT
<213> ORGANISM: Chlamydia trachomatis

<400> SEQUENCE: 109

Phe Asp Ala Asp Thr Ile Arg Ile Ala
1               5

<210> SEQ ID NO 110
<211> LENGTH: 9
<212> TYPE: PRT
<213> ORGANISM: Chlamydia trachomatis

<400> SEQUENCE: 110

Asp Ala Asp Thr Ile Arg Ile Ala Gln
1               5

<210> SEQ ID NO 111
<211> LENGTH: 9
<212> TYPE: PRT
<213> ORGANISM: Chlamydia trachomatis

<400> SEQUENCE: 111

Ala Asp Thr Ile Arg Ile Ala Gln Pro
1               5

<210> SEQ ID NO 112
<211> LENGTH: 9
<212> TYPE: PRT
<213> ORGANISM: Chlamydia trachomatis

<400> SEQUENCE: 112

Asp Thr Ile Arg Ile Ala Gln Pro Lys
1               5

<210> SEQ ID NO 113
<211> LENGTH: 9
<212> TYPE: PRT
<213> ORGANISM: Chlamydia trachomatis

<400> SEQUENCE: 113
```

```
Thr Ile Arg Ile Ala Gln Pro Lys Ser
1               5

<210> SEQ ID NO 114
<211> LENGTH: 9
<212> TYPE: PRT
<213> ORGANISM: Chlamydia trachomatis

<400> SEQUENCE: 114

Ile Arg Ile Ala Gln Pro Lys Ser Ala
1               5

<210> SEQ ID NO 115
<211> LENGTH: 9
<212> TYPE: PRT
<213> ORGANISM: Chlamydia trachomatis

<400> SEQUENCE: 115

Arg Ile Ala Gln Pro Lys Ser Ala Thr
1               5

<210> SEQ ID NO 116
<211> LENGTH: 9
<212> TYPE: PRT
<213> ORGANISM: Chlamydia trachomatis

<400> SEQUENCE: 116

Ile Ala Gln Pro Lys Ser Ala Thr Ala
1               5

<210> SEQ ID NO 117
<211> LENGTH: 9
<212> TYPE: PRT
<213> ORGANISM: Chlamydia trachomatis

<400> SEQUENCE: 117

Ala Gln Pro Lys Ser Ala Thr Ala Ile
1               5

<210> SEQ ID NO 118
<211> LENGTH: 9
<212> TYPE: PRT
<213> ORGANISM: Chlamydia trachomatis

<400> SEQUENCE: 118

Gln Pro Lys Ser Ala Thr Ala Ile Phe
1               5

<210> SEQ ID NO 119
<211> LENGTH: 9
<212> TYPE: PRT
<213> ORGANISM: Chlamydia trachomatis

<400> SEQUENCE: 119

Pro Lys Ser Ala Thr Ala Ile Phe Asp
1               5

<210> SEQ ID NO 120
<211> LENGTH: 9
<212> TYPE: PRT
<213> ORGANISM: Chlamydia trachomatis

<400> SEQUENCE: 120

Lys Ser Ala Thr Ala Ile Phe Asp Thr
```

```
1               5
```

<210> SEQ ID NO 121
<211> LENGTH: 9
<212> TYPE: PRT
<213> ORGANISM: Chlamydia trachomatis

<400> SEQUENCE: 121

```
Ser Ala Thr Ala Ile Phe Asp Thr Thr
1               5
```

<210> SEQ ID NO 122
<211> LENGTH: 9
<212> TYPE: PRT
<213> ORGANISM: Chlamydia trachomatis

<400> SEQUENCE: 122

```
Ala Thr Ala Ile Phe Asp Thr Thr Thr
1               5
```

<210> SEQ ID NO 123
<211> LENGTH: 9
<212> TYPE: PRT
<213> ORGANISM: Chlamydia trachomatis

<400> SEQUENCE: 123

```
Thr Ala Ile Phe Asp Thr Thr Thr Leu
1               5
```

<210> SEQ ID NO 124
<211> LENGTH: 9
<212> TYPE: PRT
<213> ORGANISM: Chlamydia trachomatis

<400> SEQUENCE: 124

```
Ala Ile Phe Asp Thr Thr Thr Leu Asn
1               5
```

<210> SEQ ID NO 125
<211> LENGTH: 9
<212> TYPE: PRT
<213> ORGANISM: Chlamydia trachomatis

<400> SEQUENCE: 125

```
Ile Phe Asp Thr Thr Thr Leu Asn Pro
1               5
```

<210> SEQ ID NO 126
<211> LENGTH: 9
<212> TYPE: PRT
<213> ORGANISM: Chlamydia trachomatis

<400> SEQUENCE: 126

```
Phe Asp Thr Thr Thr Leu Asn Pro Thr
1               5
```

<210> SEQ ID NO 127
<211> LENGTH: 9
<212> TYPE: PRT
<213> ORGANISM: Chlamydia trachomatis

<400> SEQUENCE: 127

```
Asp Thr Thr Thr Leu Asn Pro Thr Ile
1               5
```

```
<210> SEQ ID NO 128
<211> LENGTH: 9
<212> TYPE: PRT
<213> ORGANISM: Chlamydia trachomatis

<400> SEQUENCE: 128

Thr Thr Thr Leu Asn Pro Thr Ile Ala
1               5

<210> SEQ ID NO 129
<211> LENGTH: 9
<212> TYPE: PRT
<213> ORGANISM: Chlamydia trachomatis

<400> SEQUENCE: 129

Thr Leu Asn Pro Thr Ile Ala Gly Ala
1               5

<210> SEQ ID NO 130
<211> LENGTH: 9
<212> TYPE: PRT
<213> ORGANISM: Chlamydia trachomatis

<400> SEQUENCE: 130

Leu Asn Pro Thr Ile Ala Gly Ala Gly
1               5

<210> SEQ ID NO 131
<211> LENGTH: 9
<212> TYPE: PRT
<213> ORGANISM: Chlamydia trachomatis

<400> SEQUENCE: 131

Asn Pro Thr Ile Ala Gly Ala Gly Asp
1               5

<210> SEQ ID NO 132
<211> LENGTH: 9
<212> TYPE: PRT
<213> ORGANISM: Chlamydia trachomatis

<400> SEQUENCE: 132

Pro Thr Ile Ala Gly Ala Gly Asp Val
1               5

<210> SEQ ID NO 133
<211> LENGTH: 9
<212> TYPE: PRT
<213> ORGANISM: Chlamydia trachomatis

<400> SEQUENCE: 133

Thr Ile Ala Gly Ala Gly Asp Val Lys
1               5

<210> SEQ ID NO 134
<211> LENGTH: 9
<212> TYPE: PRT
<213> ORGANISM: Chlamydia trachomatis

<400> SEQUENCE: 134

Ile Ala Gly Ala Gly Asp Val Lys Thr
1               5

<210> SEQ ID NO 135
```

```
<211> LENGTH: 9
<212> TYPE: PRT
<213> ORGANISM: Chlamydia trachomatis

<400> SEQUENCE: 135

Ala Gly Ala Gly Asp Val Lys Thr Gly
1               5

<210> SEQ ID NO 136
<211> LENGTH: 9
<212> TYPE: PRT
<213> ORGANISM: Chlamydia trachomatis

<400> SEQUENCE: 136

Gly Ala Gly Asp Val Lys Thr Gly Ala
1               5

<210> SEQ ID NO 137
<211> LENGTH: 9
<212> TYPE: PRT
<213> ORGANISM: Chlamydia trachomatis

<400> SEQUENCE: 137

Ala Gly Asp Val Lys Thr Gly Ala Glu
1               5

<210> SEQ ID NO 138
<211> LENGTH: 9
<212> TYPE: PRT
<213> ORGANISM: Chlamydia trachomatis

<400> SEQUENCE: 138

Gly Asp Val Lys Thr Gly Ala Glu Gly
1               5

<210> SEQ ID NO 139
<211> LENGTH: 9
<212> TYPE: PRT
<213> ORGANISM: Chlamydia trachomatis

<400> SEQUENCE: 139

Asp Val Lys Thr Gly Ala Glu Gly Gln
1               5

<210> SEQ ID NO 140
<211> LENGTH: 9
<212> TYPE: PRT
<213> ORGANISM: Chlamydia trachomatis

<400> SEQUENCE: 140

Val Lys Thr Gly Ala Glu Gly Gln Leu
1               5

<210> SEQ ID NO 141
<211> LENGTH: 9
<212> TYPE: PRT
<213> ORGANISM: Chlamydia trachomatis

<400> SEQUENCE: 141

Lys Thr Gly Ala Glu Gly Gln Leu Gly
1               5

<210> SEQ ID NO 142
<211> LENGTH: 9
<212> TYPE: PRT
```

<213> ORGANISM: Chlamydia trachomatis

<400> SEQUENCE: 142

Thr Gly Ala Glu Gly Gln Leu Gly Asp
1               5

<210> SEQ ID NO 143
<211> LENGTH: 9
<212> TYPE: PRT
<213> ORGANISM: Chlamydia trachomatis

<400> SEQUENCE: 143

Gly Ala Glu Gly Gln Leu Gly Asp Thr
1               5

<210> SEQ ID NO 144
<211> LENGTH: 9
<212> TYPE: PRT
<213> ORGANISM: Chlamydia trachomatis

<400> SEQUENCE: 144

Ala Glu Gly Gln Leu Gly Asp Thr Met
1               5

<210> SEQ ID NO 145
<211> LENGTH: 9
<212> TYPE: PRT
<213> ORGANISM: Chlamydia trachomatis

<400> SEQUENCE: 145

Glu Gly Gln Leu Gly Asp Thr Met Gln
1               5

<210> SEQ ID NO 146
<211> LENGTH: 9
<212> TYPE: PRT
<213> ORGANISM: Chlamydia trachomatis

<400> SEQUENCE: 146

Gly Gln Leu Gly Asp Thr Met Gln Ile
1               5

<210> SEQ ID NO 147
<211> LENGTH: 9
<212> TYPE: PRT
<213> ORGANISM: Chlamydia trachomatis

<400> SEQUENCE: 147

Gln Leu Gly Asp Thr Met Gln Ile Val
1               5

<210> SEQ ID NO 148
<211> LENGTH: 9
<212> TYPE: PRT
<213> ORGANISM: Chlamydia trachomatis

<400> SEQUENCE: 148

Leu Gly Asp Thr Met Gln Ile Val Ser
1               5

<210> SEQ ID NO 149
<211> LENGTH: 9
<212> TYPE: PRT
<213> ORGANISM: Chlamydia trachomatis

```
<400> SEQUENCE: 149

Ser Arg Ala Ser Phe Asp Ser Asp Thr
1               5

<210> SEQ ID NO 150
<211> LENGTH: 9
<212> TYPE: PRT
<213> ORGANISM: Chlamydia trachomatis

<400> SEQUENCE: 150

Arg Ala Ser Phe Asp Ser Asp Thr Ile
1               5

<210> SEQ ID NO 151
<211> LENGTH: 9
<212> TYPE: PRT
<213> ORGANISM: Chlamydia trachomatis

<400> SEQUENCE: 151

Ala Ser Phe Asp Ser Asp Thr Ile Arg
1               5

<210> SEQ ID NO 152
<211> LENGTH: 9
<212> TYPE: PRT
<213> ORGANISM: Chlamydia trachomatis

<400> SEQUENCE: 152

Ser Phe Asp Ser Asp Thr Ile Arg Ile
1               5

<210> SEQ ID NO 153
<211> LENGTH: 9
<212> TYPE: PRT
<213> ORGANISM: Chlamydia trachomatis

<400> SEQUENCE: 153

Phe Asp Ser Asp Thr Ile Arg Ile Ala
1               5

<210> SEQ ID NO 154
<211> LENGTH: 9
<212> TYPE: PRT
<213> ORGANISM: Chlamydia trachomatis

<400> SEQUENCE: 154

Asp Ser Asp Thr Ile Arg Ile Ala Gln
1               5

<210> SEQ ID NO 155
<211> LENGTH: 9
<212> TYPE: PRT
<213> ORGANISM: Chlamydia trachomatis

<400> SEQUENCE: 155

Ser Asp Thr Ile Arg Ile Ala Gln Pro
1               5

<210> SEQ ID NO 156
<211> LENGTH: 9
<212> TYPE: PRT
<213> ORGANISM: Chlamydia trachomatis

<400> SEQUENCE: 156
```

Asp Thr Ile Arg Ile Ala Gln Pro Arg
1               5

<210> SEQ ID NO 157
<211> LENGTH: 9
<212> TYPE: PRT
<213> ORGANISM: Chlamydia trachomatis

<400> SEQUENCE: 157

Thr Ile Arg Ile Ala Gln Pro Arg Leu
1               5

<210> SEQ ID NO 158
<211> LENGTH: 9
<212> TYPE: PRT
<213> ORGANISM: Chlamydia trachomatis

<400> SEQUENCE: 158

Ile Arg Ile Ala Gln Pro Arg Leu Val
1               5

<210> SEQ ID NO 159
<211> LENGTH: 9
<212> TYPE: PRT
<213> ORGANISM: Chlamydia trachomatis

<400> SEQUENCE: 159

Arg Ile Ala Gln Pro Arg Leu Val Thr
1               5

<210> SEQ ID NO 160
<211> LENGTH: 9
<212> TYPE: PRT
<213> ORGANISM: Chlamydia trachomatis

<400> SEQUENCE: 160

Ile Ala Gln Pro Arg Leu Val Thr Pro
1               5

<210> SEQ ID NO 161
<211> LENGTH: 9
<212> TYPE: PRT
<213> ORGANISM: Chlamydia trachomatis

<400> SEQUENCE: 161

Ala Gln Pro Arg Leu Val Thr Pro Val
1               5

<210> SEQ ID NO 162
<211> LENGTH: 9
<212> TYPE: PRT
<213> ORGANISM: Chlamydia trachomatis

<400> SEQUENCE: 162

Gln Pro Arg Leu Val Thr Pro Val Val
1               5

<210> SEQ ID NO 163
<211> LENGTH: 9
<212> TYPE: PRT
<213> ORGANISM: Chlamydia trachomatis

<400> SEQUENCE: 163

Pro Arg Leu Val Thr Pro Val Val Asp
1               5

```
<210> SEQ ID NO 164
<211> LENGTH: 9
<212> TYPE: PRT
<213> ORGANISM: Chlamydia trachomatis

<400> SEQUENCE: 164

Arg Leu Val Thr Pro Val Val Asp Ile
1               5

<210> SEQ ID NO 165
<211> LENGTH: 9
<212> TYPE: PRT
<213> ORGANISM: Chlamydia trachomatis

<400> SEQUENCE: 165

Leu Val Thr Pro Val Val Asp Ile Thr
1               5

<210> SEQ ID NO 166
<211> LENGTH: 9
<212> TYPE: PRT
<213> ORGANISM: Chlamydia trachomatis

<400> SEQUENCE: 166

Val Thr Pro Val Val Asp Ile Thr Thr
1               5

<210> SEQ ID NO 167
<211> LENGTH: 9
<212> TYPE: PRT
<213> ORGANISM: Chlamydia trachomatis

<400> SEQUENCE: 167

Thr Pro Val Val Asp Ile Thr Thr Leu
1               5

<210> SEQ ID NO 168
<211> LENGTH: 9
<212> TYPE: PRT
<213> ORGANISM: Chlamydia trachomatis

<400> SEQUENCE: 168

Pro Val Val Asp Ile Thr Thr Leu Asn
1               5

<210> SEQ ID NO 169
<211> LENGTH: 9
<212> TYPE: PRT
<213> ORGANISM: Chlamydia trachomatis

<400> SEQUENCE: 169

Val Val Asp Ile Thr Thr Leu Asn Pro
1               5

<210> SEQ ID NO 170
<211> LENGTH: 9
<212> TYPE: PRT
<213> ORGANISM: Chlamydia trachomatis

<400> SEQUENCE: 170

Val Asp Ile Thr Thr Leu Asn Pro Thr
1               5
```

<210> SEQ ID NO 171
<211> LENGTH: 9
<212> TYPE: PRT
<213> ORGANISM: Chlamydia trachomatis

<400> SEQUENCE: 171

Asp Ile Thr Thr Leu Asn Pro Thr Ile
1               5

<210> SEQ ID NO 172
<211> LENGTH: 9
<212> TYPE: PRT
<213> ORGANISM: Chlamydia trachomatis

<400> SEQUENCE: 172

Ile Thr Thr Leu Asn Pro Thr Ile Ala
1               5

<210> SEQ ID NO 173
<211> LENGTH: 9
<212> TYPE: PRT
<213> ORGANISM: Chlamydia trachomatis

<400> SEQUENCE: 173

Thr Leu Asn Pro Thr Ile Ala Gly Cys
1               5

<210> SEQ ID NO 174
<211> LENGTH: 9
<212> TYPE: PRT
<213> ORGANISM: Chlamydia trachomatis

<400> SEQUENCE: 174

Leu Asn Pro Thr Ile Ala Gly Cys Gly
1               5

<210> SEQ ID NO 175
<211> LENGTH: 9
<212> TYPE: PRT
<213> ORGANISM: Chlamydia trachomatis

<400> SEQUENCE: 175

Asn Pro Thr Ile Ala Gly Cys Gly Ser
1               5

<210> SEQ ID NO 176
<211> LENGTH: 9
<212> TYPE: PRT
<213> ORGANISM: Chlamydia trachomatis

<400> SEQUENCE: 176

Pro Thr Ile Ala Gly Cys Gly Ser Val
1               5

<210> SEQ ID NO 177
<211> LENGTH: 9
<212> TYPE: PRT
<213> ORGANISM: Chlamydia trachomatis

<400> SEQUENCE: 177

Thr Ile Ala Gly Cys Gly Ser Val Ala
1               5

<210> SEQ ID NO 178
<211> LENGTH: 9

```
<212> TYPE: PRT
<213> ORGANISM: Chlamydia trachomatis

<400> SEQUENCE: 178

Ile Ala Gly Cys Gly Ser Val Ala Gly
1               5

<210> SEQ ID NO 179
<211> LENGTH: 9
<212> TYPE: PRT
<213> ORGANISM: Chlamydia trachomatis

<400> SEQUENCE: 179

Ala Gly Cys Gly Ser Val Ala Gly Ala
1               5

<210> SEQ ID NO 180
<211> LENGTH: 9
<212> TYPE: PRT
<213> ORGANISM: Chlamydia trachomatis

<400> SEQUENCE: 180

Gly Cys Gly Ser Val Ala Gly Ala Asn
1               5

<210> SEQ ID NO 181
<211> LENGTH: 9
<212> TYPE: PRT
<213> ORGANISM: Chlamydia trachomatis

<400> SEQUENCE: 181

Cys Gly Ser Val Ala Gly Ala Asn Thr
1               5

<210> SEQ ID NO 182
<211> LENGTH: 9
<212> TYPE: PRT
<213> ORGANISM: Chlamydia trachomatis

<400> SEQUENCE: 182

Gly Ser Val Ala Gly Ala Asn Thr Glu
1               5

<210> SEQ ID NO 183
<211> LENGTH: 9
<212> TYPE: PRT
<213> ORGANISM: Chlamydia trachomatis

<400> SEQUENCE: 183

Ser Val Ala Gly Ala Asn Thr Glu Gly
1               5

<210> SEQ ID NO 184
<211> LENGTH: 9
<212> TYPE: PRT
<213> ORGANISM: Chlamydia trachomatis

<400> SEQUENCE: 184

Val Ala Gly Ala Asn Thr Glu Gly Gln
1               5

<210> SEQ ID NO 185
<211> LENGTH: 9
<212> TYPE: PRT
<213> ORGANISM: Chlamydia trachomatis
```

<400> SEQUENCE: 185

Ala Gly Ala Asn Thr Glu Gly Gln Ile
1               5

<210> SEQ ID NO 186
<211> LENGTH: 9
<212> TYPE: PRT
<213> ORGANISM: Chlamydia trachomatis

<400> SEQUENCE: 186

Gly Ala Asn Thr Glu Gly Gln Ile Ser
1               5

<210> SEQ ID NO 187
<211> LENGTH: 9
<212> TYPE: PRT
<213> ORGANISM: Chlamydia trachomatis

<400> SEQUENCE: 187

Ala Asn Thr Glu Gly Gln Ile Ser Asp
1               5

<210> SEQ ID NO 188
<211> LENGTH: 9
<212> TYPE: PRT
<213> ORGANISM: Chlamydia trachomatis

<400> SEQUENCE: 188

Asn Thr Glu Gly Gln Ile Ser Asp Thr
1               5

<210> SEQ ID NO 189
<211> LENGTH: 9
<212> TYPE: PRT
<213> ORGANISM: Chlamydia trachomatis

<400> SEQUENCE: 189

Thr Glu Gly Gln Ile Ser Asp Thr Met
1               5

<210> SEQ ID NO 190
<211> LENGTH: 9
<212> TYPE: PRT
<213> ORGANISM: Chlamydia trachomatis

<400> SEQUENCE: 190

Glu Gly Gln Ile Ser Asp Thr Met Gln
1               5

<210> SEQ ID NO 191
<211> LENGTH: 9
<212> TYPE: PRT
<213> ORGANISM: Chlamydia trachomatis

<400> SEQUENCE: 191

Gly Gln Ile Ser Asp Thr Met Gln Ile
1               5

<210> SEQ ID NO 192
<211> LENGTH: 9
<212> TYPE: PRT
<213> ORGANISM: Chlamydia trachomatis

<400> SEQUENCE: 192

Gln Ile Ser Asp Thr Met Gln Ile Val
1               5

<210> SEQ ID NO 193
<211> LENGTH: 9
<212> TYPE: PRT
<213> ORGANISM: Chlamydia trachomatis

<400> SEQUENCE: 193

Ile Ser Asp Thr Met Gln Ile Val Ser
1               5

<210> SEQ ID NO 194
<211> LENGTH: 17
<212> TYPE: PRT
<213> ORGANISM: Chlamydia trachomatis

<400> SEQUENCE: 194

Phe Asp Thr Thr Thr Leu Asn Pro Thr Ile Ala Gly Ala Gly Asp Val
1               5                   10                  15

Lys

<210> SEQ ID NO 195
<211> LENGTH: 9
<212> TYPE: PRT
<213> ORGANISM: Chlamydia trachomatis

<400> SEQUENCE: 195

Asn Met Phe Thr Pro Tyr Ile Gly Val
1               5

<210> SEQ ID NO 196
<211> LENGTH: 9
<212> TYPE: PRT
<213> ORGANISM: Chlamydia trachomatis

<400> SEQUENCE: 196

Met Phe Thr Pro Tyr Ile Gly Val Lys
1               5

<210> SEQ ID NO 197
<211> LENGTH: 9
<212> TYPE: PRT
<213> ORGANISM: Chlamydia trachomatis

<400> SEQUENCE: 197

Phe Thr Pro Tyr Ile Gly Val Lys Trp
1               5

<210> SEQ ID NO 198
<211> LENGTH: 9
<212> TYPE: PRT
<213> ORGANISM: Chlamydia trachomatis

<400> SEQUENCE: 198

Thr Pro Tyr Ile Gly Val Lys Trp Ser
1               5

<210> SEQ ID NO 199
<211> LENGTH: 9
<212> TYPE: PRT
<213> ORGANISM: Chlamydia trachomatis

<400> SEQUENCE: 199

Pro Tyr Ile Gly Val Lys Trp Ser Arg
1               5

<210> SEQ ID NO 200
<211> LENGTH: 9
<212> TYPE: PRT
<213> ORGANISM: Chlamydia trachomatis

<400> SEQUENCE: 200

Tyr Ile Gly Val Lys Trp Ser Arg Ala
1               5

<210> SEQ ID NO 201
<211> LENGTH: 9
<212> TYPE: PRT
<213> ORGANISM: Chlamydia trachomatis

<400> SEQUENCE: 201

Ile Gly Val Lys Trp Ser Arg Ala Ser
1               5

<210> SEQ ID NO 202
<211> LENGTH: 9
<212> TYPE: PRT
<213> ORGANISM: Chlamydia trachomatis

<400> SEQUENCE: 202

Gly Val Lys Trp Ser Arg Ala Ser Phe
1               5

<210> SEQ ID NO 203
<211> LENGTH: 9
<212> TYPE: PRT
<213> ORGANISM: Chlamydia trachomatis

<400> SEQUENCE: 203

Val Lys Trp Ser Arg Ala Ser Phe Asp
1               5

<210> SEQ ID NO 204
<211> LENGTH: 9
<212> TYPE: PRT
<213> ORGANISM: Chlamydia trachomatis

<400> SEQUENCE: 204

Lys Trp Ser Arg Ala Ser Phe Asp Ala
1               5

<210> SEQ ID NO 205
<211> LENGTH: 9
<212> TYPE: PRT
<213> ORGANISM: Chlamydia trachomatis

<400> SEQUENCE: 205

Trp Ser Arg Ala Ser Phe Asp Ala Asp
1               5

<210> SEQ ID NO 206
<211> LENGTH: 9
<212> TYPE: PRT
<213> ORGANISM: Chlamydia trachomatis

<400> SEQUENCE: 206

Ser Arg Ala Ser Phe Asp Ala Asp Thr

```
1               5
```

<210> SEQ ID NO 207
<211> LENGTH: 9
<212> TYPE: PRT
<213> ORGANISM: Chlamydia trachomatis

<400> SEQUENCE: 207

```
Arg Ala Ser Phe Asp Ala Asp Thr Ile
1               5
```

<210> SEQ ID NO 208
<211> LENGTH: 9
<212> TYPE: PRT
<213> ORGANISM: Chlamydia trachomatis

<400> SEQUENCE: 208

```
Ala Ser Phe Asp Ala Asp Thr Ile Arg
1               5
```

<210> SEQ ID NO 209
<211> LENGTH: 9
<212> TYPE: PRT
<213> ORGANISM: Chlamydia trachomatis

<400> SEQUENCE: 209

```
Ser Phe Asp Ala Asp Thr Ile Arg Ile
1               5
```

<210> SEQ ID NO 210
<211> LENGTH: 9
<212> TYPE: PRT
<213> ORGANISM: Chlamydia trachomatis

<400> SEQUENCE: 210

```
Phe Asp Ala Asp Thr Ile Arg Ile Ala
1               5
```

<210> SEQ ID NO 211
<211> LENGTH: 9
<212> TYPE: PRT
<213> ORGANISM: Chlamydia trachomatis

<400> SEQUENCE: 211

```
Asp Ala Asp Thr Ile Arg Ile Ala Gln
1               5
```

<210> SEQ ID NO 212
<211> LENGTH: 9
<212> TYPE: PRT
<213> ORGANISM: Chlamydia trachomatis

<400> SEQUENCE: 212

```
Ala Asp Thr Ile Arg Ile Ala Gln Pro
1               5
```

<210> SEQ ID NO 213
<211> LENGTH: 9
<212> TYPE: PRT
<213> ORGANISM: Chlamydia trachomatis

<400> SEQUENCE: 213

```
Asp Thr Ile Arg Ile Ala Gln Pro Lys
1               5
```

<210> SEQ ID NO 214
<211> LENGTH: 9
<212> TYPE: PRT
<213> ORGANISM: Chlamydia trachomatis

<400> SEQUENCE: 214

Thr Ile Arg Ile Ala Gln Pro Lys Ser
1               5

<210> SEQ ID NO 215
<211> LENGTH: 9
<212> TYPE: PRT
<213> ORGANISM: Chlamydia trachomatis

<400> SEQUENCE: 215

Ile Arg Ile Ala Gln Pro Lys Ser Ala
1               5

<210> SEQ ID NO 216
<211> LENGTH: 9
<212> TYPE: PRT
<213> ORGANISM: Chlamydia trachomatis

<400> SEQUENCE: 216

Arg Ile Ala Gln Pro Lys Ser Ala Thr
1               5

<210> SEQ ID NO 217
<211> LENGTH: 9
<212> TYPE: PRT
<213> ORGANISM: Chlamydia trachomatis

<400> SEQUENCE: 217

Ile Ala Gln Pro Lys Ser Ala Thr Ala
1               5

<210> SEQ ID NO 218
<211> LENGTH: 9
<212> TYPE: PRT
<213> ORGANISM: Chlamydia trachomatis

<400> SEQUENCE: 218

Ala Gln Pro Lys Ser Ala Thr Ala Ile
1               5

<210> SEQ ID NO 219
<211> LENGTH: 9
<212> TYPE: PRT
<213> ORGANISM: Chlamydia trachomatis

<400> SEQUENCE: 219

Gln Pro Lys Ser Ala Thr Ala Ile Phe
1               5

<210> SEQ ID NO 220
<211> LENGTH: 9
<212> TYPE: PRT
<213> ORGANISM: Chlamydia trachomatis

<400> SEQUENCE: 220

Pro Lys Ser Ala Thr Ala Ile Phe Asp
1               5

<210> SEQ ID NO 221

```
<211> LENGTH: 9
<212> TYPE: PRT
<213> ORGANISM: Chlamydia trachomatis

<400> SEQUENCE: 221

Lys Ser Ala Thr Ala Ile Phe Asp Thr
1               5

<210> SEQ ID NO 222
<211> LENGTH: 9
<212> TYPE: PRT
<213> ORGANISM: Chlamydia trachomatis

<400> SEQUENCE: 222

Ser Ala Thr Ala Ile Phe Asp Thr Thr
1               5

<210> SEQ ID NO 223
<211> LENGTH: 9
<212> TYPE: PRT
<213> ORGANISM: Chlamydia trachomatis

<400> SEQUENCE: 223

Ala Thr Ala Ile Phe Asp Thr Thr Thr
1               5

<210> SEQ ID NO 224
<211> LENGTH: 9
<212> TYPE: PRT
<213> ORGANISM: Chlamydia trachomatis

<400> SEQUENCE: 224

Thr Ala Ile Phe Asp Thr Thr Thr Leu
1               5

<210> SEQ ID NO 225
<211> LENGTH: 9
<212> TYPE: PRT
<213> ORGANISM: Chlamydia trachomatis

<400> SEQUENCE: 225

Ala Ile Phe Asp Thr Thr Thr Leu Asn
1               5

<210> SEQ ID NO 226
<211> LENGTH: 9
<212> TYPE: PRT
<213> ORGANISM: Chlamydia trachomatis

<400> SEQUENCE: 226

Ile Phe Asp Thr Thr Thr Leu Asn Pro
1               5

<210> SEQ ID NO 227
<211> LENGTH: 9
<212> TYPE: PRT
<213> ORGANISM: Chlamydia trachomatis

<400> SEQUENCE: 227

Phe Asp Thr Thr Thr Leu Asn Pro Thr
1               5

<210> SEQ ID NO 228
<211> LENGTH: 9
<212> TYPE: PRT
```

<213> ORGANISM: Chlamydia trachomatis

<400> SEQUENCE: 228

Asp Thr Thr Thr Leu Asn Pro Thr Ile
1               5

<210> SEQ ID NO 229
<211> LENGTH: 9
<212> TYPE: PRT
<213> ORGANISM: Chlamydia trachomatis

<400> SEQUENCE: 229

Thr Thr Thr Leu Asn Pro Thr Ile Ala
1 5

<210> SEQ ID NO 230
<211> LENGTH: 9
<212> TYPE: PRT
<213> ORGANISM: Chlamydia trachomatis

<400> SEQUENCE: 230

Thr Thr Leu Asn Pro Thr Ile Ala Gly
1 5

<210> SEQ ID NO 231
<211> LENGTH: 9
<212> TYPE: PRT
<213> ORGANISM: Chlamydia trachomatis

<400> SEQUENCE: 231

Thr Leu Asn Pro Thr Ile Ala Gly Ala
1 5

<210> SEQ ID NO 232
<211> LENGTH: 9
<212> TYPE: PRT
<213> ORGANISM: Chlamydia trachomatis

<400> SEQUENCE: 232

Leu Asn Pro Thr Ile Ala Gly Ala Gly
1 5

<210> SEQ ID NO 233
<211> LENGTH: 9
<212> TYPE: PRT
<213> ORGANISM: Chlamydia trachomatis

<400> SEQUENCE: 233

Asn Pro Thr Ile Ala Gly Ala Gly Asp
1 5

<210> SEQ ID NO 234
<211> LENGTH: 9
<212> TYPE: PRT
<213> ORGANISM: Chlamydia trachomatis

<400> SEQUENCE: 234

Pro Thr Ile Ala Gly Ala Gly Asp Val
1 5

<210> SEQ ID NO 235
<211> LENGTH: 9
<212> TYPE: PRT
<213> ORGANISM: Chlamydia trachomatis

<400> SEQUENCE: 235

Thr Ile Ala Gly Ala Gly Asp Val Lys
1               5

<210> SEQ ID NO 236
<211> LENGTH: 9
<212> TYPE: PRT
<213> ORGANISM: Chlamydia trachomatis

<400> SEQUENCE: 236

Ile Ala Gly Ala Gly Asp Val Lys Thr
1               5

<210> SEQ ID NO 237
<211> LENGTH: 9
<212> TYPE: PRT
<213> ORGANISM: Chlamydia trachomatis

<400> SEQUENCE: 237

Ala Gly Ala Gly Asp Val Lys Thr Gly
1               5

<210> SEQ ID NO 238
<211> LENGTH: 9
<212> TYPE: PRT
<213> ORGANISM: Chlamydia trachomatis

<400> SEQUENCE: 238

Gly Ala Gly Asp Val Lys Thr Gly Ala
1               5

<210> SEQ ID NO 239
<211> LENGTH: 9
<212> TYPE: PRT
<213> ORGANISM: Chlamydia trachomatis

<400> SEQUENCE: 239

Ala Gly Asp Val Lys Thr Gly Ala Glu
1               5

<210> SEQ ID NO 240
<211> LENGTH: 9
<212> TYPE: PRT
<213> ORGANISM: Chlamydia trachomatis

<400> SEQUENCE: 240

Gly Asp Val Lys Thr Gly Ala Glu Gly
1               5

<210> SEQ ID NO 241
<211> LENGTH: 9
<212> TYPE: PRT
<213> ORGANISM: Chlamydia trachomatis

<400> SEQUENCE: 241

Asp Val Lys Thr Gly Ala Glu Gly Gln
1               5

<210> SEQ ID NO 242
<211> LENGTH: 9
<212> TYPE: PRT
<213> ORGANISM: Chlamydia trachomatis

<400> SEQUENCE: 242

```
Val Lys Thr Gly Ala Glu Gly Gln Leu
1               5

<210> SEQ ID NO 243
<211> LENGTH: 9
<212> TYPE: PRT
<213> ORGANISM: Chlamydia trachomatis

<400> SEQUENCE: 243

Lys Thr Gly Ala Glu Gly Gln Leu Gly
1               5

<210> SEQ ID NO 244
<211> LENGTH: 9
<212> TYPE: PRT
<213> ORGANISM: Chlamydia trachomatis

<400> SEQUENCE: 244

Thr Gly Ala Glu Gly Gln Leu Gly Asp
1               5

<210> SEQ ID NO 245
<211> LENGTH: 9
<212> TYPE: PRT
<213> ORGANISM: Chlamydia trachomatis

<400> SEQUENCE: 245

Gly Ala Glu Gly Gln Leu Gly Asp Thr
1               5

<210> SEQ ID NO 246
<211> LENGTH: 9
<212> TYPE: PRT
<213> ORGANISM: Chlamydia trachomatis

<400> SEQUENCE: 246

Ala Glu Gly Gln Leu Gly Asp Thr Met
1               5

<210> SEQ ID NO 247
<211> LENGTH: 9
<212> TYPE: PRT
<213> ORGANISM: Chlamydia trachomatis

<400> SEQUENCE: 247

Glu Gly Gln Leu Gly Asp Thr Met Gln
1               5

<210> SEQ ID NO 248
<211> LENGTH: 9
<212> TYPE: PRT
<213> ORGANISM: Chlamydia trachomatis

<400> SEQUENCE: 248

Gly Gln Leu Gly Asp Leu Met Gln Ile
1               5

<210> SEQ ID NO 249
<211> LENGTH: 9
<212> TYPE: PRT
<213> ORGANISM: Chlamydia trachomatis

<400> SEQUENCE: 249

Gln Leu Gly Asp Thr Met Gln Ile Val
1               5
```

```
<210> SEQ ID NO 250
<211> LENGTH: 9
<212> TYPE: PRT
<213> ORGANISM: Chlamydia trachomatis

<400> SEQUENCE: 250

Leu Gly Asp Thr Met Gln Ile Val Ser
1               5

<210> SEQ ID NO 251
<211> LENGTH: 9
<212> TYPE: PRT
<213> ORGANISM: Chlamydia trachomatis

<400> SEQUENCE: 251

Gly Asp Thr Met Gln Ile Val Ser Leu
1               5

<210> SEQ ID NO 252
<211> LENGTH: 9
<212> TYPE: PRT
<213> ORGANISM: Chlamydia trachomatis

<400> SEQUENCE: 252

Asp Thr Met Gln Ile Val Ser Leu Gln
1               5

<210> SEQ ID NO 253
<211> LENGTH: 9
<212> TYPE: PRT
<213> ORGANISM: Chlamydia trachomatis

<400> SEQUENCE: 253

Thr Met Gln Ile Val Ser Leu Gln Leu
1               5

<210> SEQ ID NO 254
<211> LENGTH: 9
<212> TYPE: PRT
<213> ORGANISM: Chlamydia trachomatis

<400> SEQUENCE: 254

Met Gln Ile Val Ser Leu Gln Leu Asn
1               5

<210> SEQ ID NO 255
<211> LENGTH: 80
<212> TYPE: PRT
<213> ORGANISM: Chlamydia trachomatis

<400> SEQUENCE: 255

Glu Trp Gln Ala Ser Leu Ala Leu Ser Tyr Arg Leu Asn Met Phe Thr
1               5                   10                  15

Pro Tyr Ile Gly Val Lys Trp Ser Arg Ala Ser Phe Asp Ala Asp Thr
            20                  25                  30

Ile Arg Ile Ala Gln Pro Lys Ser Ala Thr Ala Ile Phe Asp Thr Thr
        35                  40                  45

Thr Leu Asn Pro Thr Ile Ala Gly Ala Gly Asp Val Lys Thr Gly Ala
    50                  55                  60

Glu Gly Gln Leu Gly Asp Thr Met Gln Ile Val Ser Leu Gln Leu Asn
65                  70                  75                  80
```

The invention claimed is:

1. A polypeptide comprising 3 or more immuno-repeat units of surface exposed fragments of the major outer membrane protein (MOMP), wherein each immuno-repeat comprises an amino acid sequence which comprises the variable domain 4 (VD4) region of the MOMP chosen from any serotype of a Chlamydias species selected from the group consisting of *Chlamydia trachomatis, Chlamydia pneumoniae, Chlamydia muridarum, Chlamydia suis*, and *Chlamydiaphila abortus*, wherein the amino acid sequences are optionally linearized.

2. The polypeptide according to claim 1, wherein the immuno-repeats are homologous.

3. The polypeptide according to claim 1, wherein the amino acid sequences comprising the VD4 region of the MOMP are placed next to each other.

4. The polypeptide according to claim 1, wherein the immuno-repeats are heterologous.

5. The polypeptide according to claim 1, wherein the MOMP is from *Chlamydia pneumoniae* or serotype D, E, F, G, Ia or J of *Chlamydia trachomatis*.

6. The polypeptide according to claim 1, further comprising one or more of the variable domains selected from 1, 2, 3, and 4 of the MOMP from any Serotype of a *chlamydia* species selected from, the group consisting of *Chlamydia trachomatis, Chlamydia pneumoniae, Chlamydia muridarum, Chlamydia suis*, and *Chlamydiaphila abortus*.

7. The polypeptide according to claim 1, wherein the amino acid sequences are linearized.

8. The polypeptide according to claim 1, wherein the amino acid sequences comprising the VD4 region of the MOMP are spaced with a linker.

9. The polypeptide according to claim 1, comprising an amino acid sequence defined in formula I:

$$xx_1\text{-VD4-}xx_2 \quad \text{(Formula I)}$$

wherein

VD4 is independently selected from SEQ ID NO: 15-20 or an amino acid sequence which has at least 80% sequence identity with SEQ ID NO: 15-20, and $xx_1$ consists of
i) the amino acid sequence EWQASLAL-SYRLNMFTPYIGVKWSRASFDADTIRIAQPK (SEQ ID NO: 21) or
ii) a subsequence of the amino acid sequence in i) said subsequence comprising 1-38 amino acid residues, starting with the C-terminal K in the amino acid sequence in i)

and $xx_2$ consists of
iii) the amino acid sequence DTMQI-VSLQLNKMKSRKSCGIAVGTTIVDA (SEQ ID NO: 22) or
iv) a subsequence of the amino acid sequence in iii) said subsequence comprising 1-29 amino acid residues, starting with the N-terminal D in the amino acid sequence in iii).

10. The polypeptide according to claim 1, comprising the amino acid sequence selected from the group consisting of SEQ ID NO: 23-28 and 49-59.

11. Me polypeptide according to claim 1, comprising 4 or more immuno-repeat units of surface exposed fragments of the major outer membrane protein (MOMP), wherein each immuno-repeat comprises an amino acid sequence which comprises the variable domain 4 (VD4) region of the MOMP chosen from any serotype of a *Chlamydia* species selected from *Chlamydia trachomatis, Chlamydia pneumoniae, Chlamydia muridarum, Chlamydia suis*, and *Chlamydiaphila abortus*.

12. The polypeptide according to claim 1, further comprising a moiety that facilitates export of the polypeptide when produced recombinantly, a moiety that facilitates purification of the fusion protein, or a moiety which enhances immunogenicity.

13. The polypeptide according to claim 12, wherein the enhancer of immunogenicity is an additional T-cell target which is chosen from a *Chlamydia trachomatis* (Ct) antigen selected from the group consisting of CT043, CT004, CT414 and CT681.

14. The polypeptide according to claim 13, comprising the amino acid sequence selected from the group consisting of SEQ ID NO: 60-68.

15. The polypeptide according to claim 14, comprising the amino acid sequence SEQ ID NO: 64.

* * * * *

UNITED STATES PATENT AND TRADEMARK OFFICE
CERTIFICATE OF CORRECTION

PATENT NO. : 10,925,954 B2  
APPLICATION NO. : 15/956731  
DATED : February 23, 2021  
INVENTOR(S) : Frank Follmann et al.

Page 1 of 1

It is certified that error appears in the above-identified patent and that said Letters Patent is hereby corrected as shown below:

In the Claims

Claim 11, first line (Column 182, Line 21), replace "Me polypeptide" with --The polypeptide--.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*